United States Patent
Aradottir et al.

(10) Patent No.: US 11,298,461 B2
(45) Date of Patent: Apr. 12, 2022

(54) BASAL TITRATION WITH ADAPTIVE TARGET GLUCOSE LEVEL

(71) Applicant: Novo Nordisk A/S, Bagsvaerd (DK)

(72) Inventors: Tinna Bjoerk Aradottir, Copenhagen (DK); Henrik Bengtsson, Taastrup (DK); Morten Lind Jensen, Copenhagen OE (DK); Pete Brockmeier, Copenhagen V (DK)

(73) Assignee: Novo Nordisk A/S, Bagsvaerd (DK)

( * ) Notice: Subject to any disclaimer, the term of this patent is extended or adjusted under 35 U.S.C. 154(b) by 254 days.

(21) Appl. No.: 16/622,326

(22) PCT Filed: Jun. 8, 2018

(86) PCT No.: PCT/EP2018/065126
§ 371 (c)(1),
(2) Date: Dec. 13, 2019

(87) PCT Pub. No.: WO2018/228932
PCT Pub. Date: Dec. 20, 2018

(65) Prior Publication Data
US 2021/0146046 A1  May 20, 2021

Related U.S. Application Data

(60) Provisional application No. 62/522,811, filed on Jun. 21, 2017, provisional application No. 62/520,139, filed on Jun. 15, 2017.

(30) Foreign Application Priority Data

Jun. 29, 2017 (EP) .................................... 17178877
Sep. 8, 2017 (EP) .................................... 17190146

(51) Int. Cl.
A61M 5/172 (2006.01)
G16H 20/17 (2018.01)
A61M 5/142 (2006.01)

(52) U.S. Cl.
CPC .......... *A61M 5/1723* (2013.01); *G16H 20/17* (2018.01); *A61M 2005/14208* (2013.01); *A61M 2005/1726* (2013.01); *A61M 2205/52* (2013.01)

(58) Field of Classification Search
CPC .. A61B 5/14532; A61B 5/4839; G16H 20/17; G16H 20/10; A61M 5/1723; A61K 38/28
See application file for complete search history.

(56) References Cited

U.S. PATENT DOCUMENTS 6,923,763 B1  8/2005  Kovatchev et al.
8,370,077 B2  2/2013  Bashan et al.
(Continued)

FOREIGN PATENT DOCUMENTS

WO  2011157402 A1  12/2011

OTHER PUBLICATIONS

S. Wolfe, "Contribution of the dawn phenomenon to the fasting and postbreakfast hyperglycaemia in type 1 diabetes treated with once-nightly insulin glargine", Endocr Pract., 2012, vol. 18, pp. 558-562.
(Continued)

*Primary Examiner* — Manuel A Mendez
(74) *Attorney, Agent, or Firm* — Wesley Nicolas

(57) ABSTRACT

Systems and methods are provided for adjusting long acting insulin medicament dosages for a subject. A plurality of timestamped glucose measurements of the subject is obtained. A titration glucose level (246) is computed as a measure of central tendency (244, 268, 274) of a titration subset of small glucose measurements (240, 269, 273) identified within the timestamped glucose measurements,
(Continued)

wherein the measure of central tendency represents a measure of small glucose measurements for the primary time window. A long acting insulin medicament dosage (216) is adjusted or maintained based upon the obtained titration glucose level (246).

15 Claims, 24 Drawing Sheets

(56) References Cited

U.S. PATENT DOCUMENTS

| | | | |
|---|---|---|---|
| 8,562,587 | B2 | 10/2013 | Kovatchev et al. |
| 8,688,386 | B2 | 4/2014 | Shadforth et al. |
| 2009/0304665 | A1* | 12/2009 | Frost .................... A61K 38/28 424/94.5 |
| 2010/0075353 | A1 | 3/2010 | Heaton |
| 2011/0313674 | A1 | 12/2011 | Duke et al. |
| 2011/0319322 | A1 | 12/2011 | Bashan et al. |
| 2012/0232520 | A1 | 9/2012 | Sloan et al. |
| 2014/0350369 | A1 | 11/2014 | Budiman et al. |
| 2015/0190098 | A1 | 7/2015 | Patek et al. |
| 2017/0068790 | A1 | 3/2017 | Fuerst |

OTHER PUBLICATIONS

T. Walker, "The Rationale for Continous Glucose Monitoring-based Diabetes Treatment Decisions and Non-adjungtive Continous Glucose Monitoring Use", European Endo-crinology, 2016, vol. 12, No. 1, pp. 24-30.

Howard Zisser et al., "Bolus Calculator: A Review of Four "Smart" Insulin Pumps," Diabetes Technology & Therapeutics. 2008, vol. 10, No. 6, pp. 441-444.

Sabine Arnolds, M.D. et al., "Common Standards of Basal Insulin Titration in T2DM," J Diabetes Sci Technol, 2013, vol. 7, No. 3, pp. 771-788.

* cited by examiner

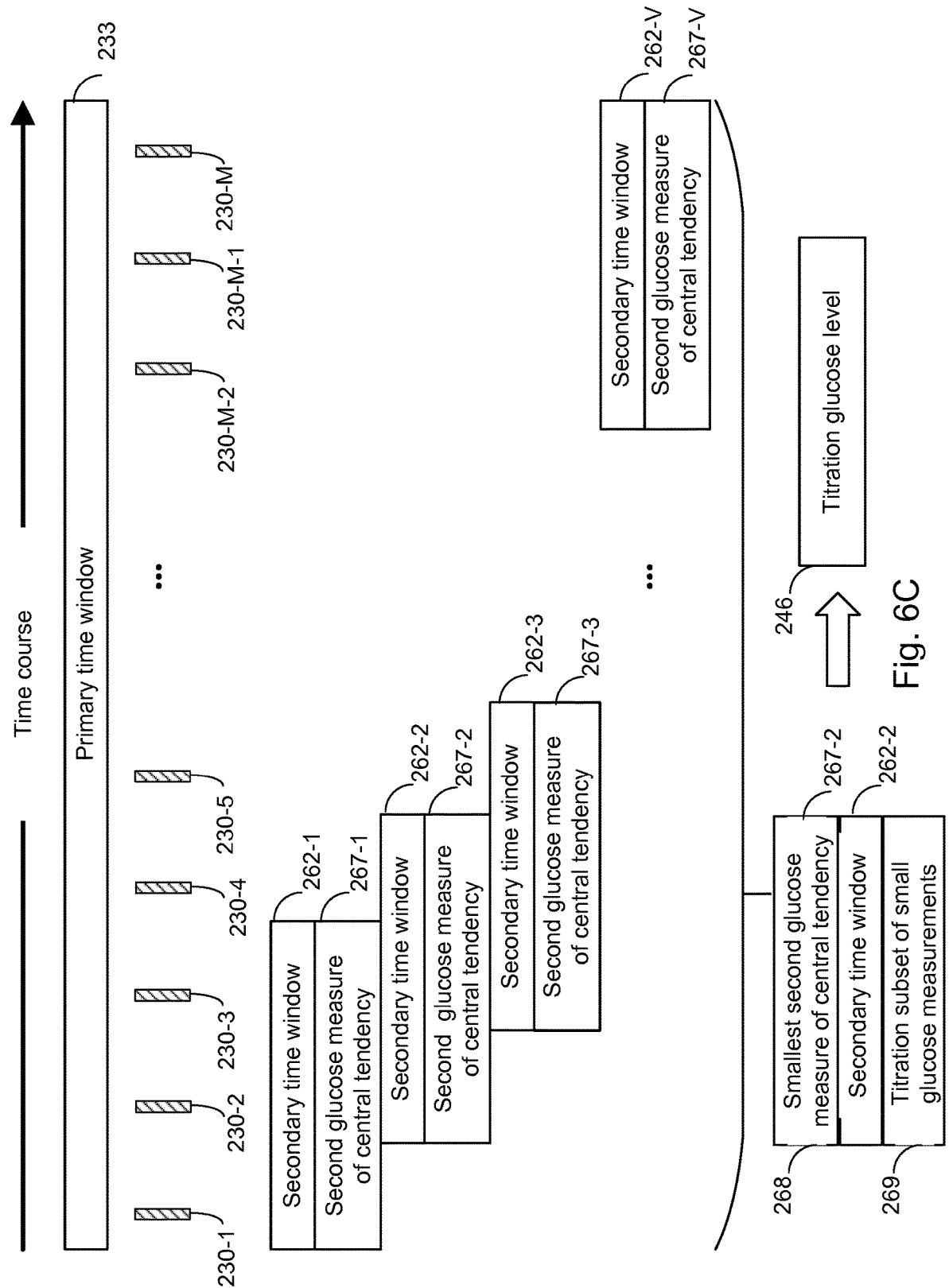

BASAL TITRATION WITH ADAPTIVE TARGET GLUCOSE LEVEL

CROSS-REFERENCE TO RELATED APPLICATIONS

This application is a 35 U.S.C. § 371 National Stage application of International Application PCT/EP2018/065126 (published as WO 2018/228932), filed Jun. 8, 2018, which claims priority to European Patent Applications 17178877.1, filed Jun. 29, 2017 and 17190146.5, filed Sep. 8, 2017, this application further claims priority under 35 U.S.C. § 119 of U.S. Provisional Applications 62/520,139, filed Jun. 15, 2017 and 62/522,811, filed Jun. 21, 2017, the contents of all above-named applications are incorporated herein by reference.

TECHNICAL FIELD

The present disclosure relates generally to systems, computer programs and computer-readable data carriers storing a computer program and methods for adjusting or maintaining a long acting insulin medicament dosage in a prescribed insulin regimen for a subject based on a titration subset of small glucose measurements identified as a subset of small glucose measurements within a plurality of glucose measurements of the subject taken over a time course.

BACKGROUND

Type 2 diabetes mellitus is characterized by progressive disruption of normal physiologic insulin secretion. In healthy individuals, basal insulin secretion by pancreatic β cells occurs continuously to maintain steady glucose levels for extended periods between meals. Also in healthy individuals, there is prandial secretion in which insulin is rapidly released in an initial first-phase spike in response to a meal, followed by prolonged insulin secretion that returns to basal levels after 2-3 hours.

Insulin is a hormone that binds to insulin receptors to lower blood glucose by facilitating cellular uptake of glucose, amino acids, and fatty acids into skeletal muscle and fat and by inhibiting the output of glucose from the liver. In normal healthy individuals, physiologic basal and prandial insulin secretions maintain euglycemia, which affects fasting plasma glucose and postprandial plasma glucose concentrations. Basal and prandial insulin secretion is impaired in Type 2 diabetes and early post-meal response is absent. To address these adverse events, patients with Type 2 diabetes are provided with insulin medicament treatment regimens. Patients with Type 1 diabetes are also provided with insulin medicament treatment regimens. The goal of these insulin medicament treatment regimens is to maintain a desired fasting blood glucose target level that will minimize estimated risk of hypo- and hyperglycaemia.

Smart titrators with adjustable step size and physiological parameter estimation and predefined fasting blood glucose target values have been developed to administer insulin medicament treatment regimens.

A Continuous Glucose Monitor (CGM) is a small wearable device that tracks glucose levels during the day and night, and which can notify when glucose levels are too high or too low, enabling the patient to take action.

The current standard of care is that patients self-monitor the blood glucose by repeated finger sticks and SMBG. However, due to the discrete nature of this practice, high or low blood glucose events may be missed, and the actual measurement time point may differ from the recommended (i.e. fasting blood glucose measured in a non-fasting state) and there may be barriers to adhere to the recommend number of measurements, see T. Walker, "The Rationale for Continuous Glucose Monitoring-based Diabetes Treatment Decisions and Non-adjunctive Continuous Glucose Monitoring Use", European Endocrinology, 2016; 12(1): 24-30. In general, the point estimate accuracy of blood glucose meters is likely to be better compared to point estimates from CGM.

Under normal circumstances, diabetes patients use SMBG to measure the fasting glucose level when they are still fasting before breakfast. However, sometimes the measurement is forgotten and either not done, or done after breakfast has been initiated, which reduces the precision of the fasting glucose level used for basal insulin titration. Automatic detection of the glucose level from CGM data to base basal insulin titration on is anticipated to reduce the risk of this use error, as CGM data are time stamped. In addition, basal insulin titration based on the morning fasting glucose level may lead to excessive insulin dosing due to the raising glucose levels in the morning due to the dawn phenomenon, see S. Wolfe, "Contribution of the dawn phenomenon to the fasting and postbreakfast hyperglycaemia in type 1 diabetes treated with once-nightly insulin glargine", Endocr. Pract., year, 18, pp. 558-562, 2012.

U.S. Pat. No. 8,370,077 B2 entitled "System for Optimizing A Patient's Inulin Dosage Regimen" to Hygieia, Inc. discloses a system for optimizing a patient's insulin dosage regimen over time in which inputs corresponding at least to one or more components in a patient's present insulin dosage regimen, and data inputs corresponding at least to the patient's blood-glucose-level measurements determined at a plurality of times. From the data inputs corresponding to the patient's blood-glucose-level measurements, determined at a plurality of times, a determination is made as to whether and by how much to vary at least one of the one or more components in the patient's present insulin dosage regimen in order to maintain the patient's future blood-glucose-level measurements within a predefined range. The blood-glucose-level measurements are tagged with an identifier reflective of when the reading was input; specifically, whether it is a morning measurement, a pre-lunch measurement, a pre-dinner measurement, a bedtime measurement, or a nighttime measurement.

United States Publication No. 2011/313674 A entitled "Insulin Optimization Systems and Testing Methods with Adjusted Exit Criterion Accounting for System Noise Associated with Biomarkers" to Roche Diagnostics Operations, Inc., discloses a method for optimizing a therapy to a diabetic patient comprising collecting at least one sampling set of biomarker data. The diabetic patient may begin collection of one or more sampling sets of biomarker data, wherein each sampling set comprises one or more sampling instances recorded over a collection period. Each sampling instance comprises one or more biomarker readings. The collection period for the sampling set may be defined as multiple sampling instances within a day, multiple sampling instances within a week, multiple sampling instances within consecutive weeks, or multiple sampling instances on consecutive days within a week. The biomarker may relate to the levels of glucose, triglycerides, low density lipids, and high density lipids. In one exemplary embodiment, the biomarker reading is a blood glucose reading, specifically a fasting blood glucose reading. In addition to the biomarker reading, each sampling instance may comprise the biomarker reading and other contextual data associated with the biomarker reading, wherein the contextual data is selected from the group consisting of the time of collection, the date of collection, the time when the last meal was consumed, the recommended dose of insulin, and combinations thereof.

United States Publication No. 2011/0319322 entitled "Systems, Methods and Devices for Achieving Glycemic Balance" to Hygieia, discloses a system for optimizing a patient's insulin dosage regimen over time, comprising at least a first memory for storing data inputs corresponding at least to one or more components in a patient's present insulin dosage regimen, and data inputs corresponding at least to the patient's blood-glucose-level measurements determined at a plurality of times, and a processor operatively connected to the at least first memory. The processor is programmed at least to determine from the data inputs corresponding to the patient's blood-glucose-level measurements determined at a plurality of times whether and by how much to vary at least one of the one or more components in the patient's present insulin dosage regimen in order to maintain the patient's future blood-glucose-level measurements within a predefined range.

United States Publication No. 2012/0232520 entitled "Multi-Function Analyte Monitor Device and Methods of use" to Abbott Diabetes Care, Inc, discloses methods, systems and devices for detecting an analyte sample, determining an analyte concentration associated with the detected analyte sample, storing the determined analyte concentration and a time associated with the determined analyte concentration, retrieving two or more stored analyte concentrations, and determining an adjusted dose level based at least in part on a current dose level and data associated with the two or more retrieved analyte concentrations are provided. For example, adjustments to dosage levels of long-acting insulin may be provided to assist in the management of diabetes and related conditions In basal insulin therapy, robust and reliable insulin titration algorithms are important, and the glucose levels used to calculate the new dose is important, and given the above background, what is needed in the art are systems and methods that provide improved insulin medicament titration.

SUMMARY

The present disclosure addresses the need in the art for systems and methods for providing improved insulin medicament titration. The input glucose level used for adjusting the amount of medicament should reflect the critical glucose levels, important for determining the optimal daily basal dose or amount of medicament. Since low glucose values are critical, they are also critical in finding the optimal daily basal dose. In this description, we refer to the glucose level used as input to a titration algorithm as the titration glucose level (TGL). A problem to be solved by the present disclosure is therefore to safely and automatically detect TGL based on data from a continuous glucose monitor (CGM). The continuous or near continuous character of CGM data or autonomously generated time stamped glucose data gives an opportunity for a more refined and dynamic detection of the glucose level to base the basal insulin titration on. In a further aspect TGL is also based on an indication of whether or not an exogenous short acting insulin medicament has been injected and influences the blood glucose level on a short term. A further aspect of the present invention is the provision of systems and methods for safe and automatic detection of a titration glucose level based on continuous or near continuous glucose data.

With continuous glucose monitors becoming cheaper and more accurate, it is estimated that the technology will become more widely used, by T1 and T2 diabetes patients. The invention allows determining TGL based on CGM data, which is useful in e.g. basal insulin titration for T2D patients. In one aspect, using the lowest average glucose of CGM data over a period of e.g. 24 hours provides a number of benefits in safety, the lowest glucose readings are the critical values in insulin treatment with a long acting insulin, as opposed to using fasting SMPG measurements, where SMPG measurements only reflect one point in time, and therefore do not ensure capture the lowest fasting glucose. An example is the dawn-effect which causes fasting glucose to rise before waking up, and hence the morning fasting SMPG measurement is higher than the fasting glucose values during the night. As opposed to predefined fasting periods fasting periods vary in real-life and therefore predefining a period as fasting is not robust. In an aspect of the present invention, CGM data is analyzed using a set of rules, enabling a fasting-glucose-equivalent to be determined automatically from the data stream. The value, coined "Titration Glucose Level," is determined by filtering out data that is of inadequate quality, that is affected by prandial artifacts, and that is influenced by insulin on board.

Accordingly, one aspect of the present disclosure provides a device for autonomously adjusting a long acting insulin medicament dosage in a prescribed insulin regimen for a subject, wherein the device comprises one or more processors and a memory, the memory comprising:

a first data structure that includes the prescribed insulin regimen including a basal insulin medicament dosage regimen, wherein the basal insulin medicament dosage regimen specifies the amount of long acting insulin medicament dosage, an insulin state indicator, wherein the insulin state indicator can indicate a short-acting-insulin-influence state, wherein the glucose measurements within the primary time window may be influenced by a short acting insulin medicament, and an only-long-acting-insulin-influence state, wherein the glucose measurements within the primary time window can be influenced by a long acting insulin medicament, but the measurements cannot be influenced by a short acting insulin medicament, and instructions that, when executed by the one or more processors, perform a method of:

(A) obtaining, a first data set, the first data set comprising a plurality of glucose measurements of the subject taken over a time course and, for each respective glucose measurement in the plurality of glucose measurements, a corresponding timestamp representing when in the time course the respective glucose measurement was made;

(B) obtaining a titration glucose level based on small glucose measurements and the state of the insulin state indicator by:

(i) obtaining a primary time window within the time course defining the period of time comprising the glucose measurements in the first data set to be used for identifying the titration glucose level, (ii) identifying a titration subset of small glucose measurements, identified as a subset of small glucose measurements within the primary time window, (iii) obtaining the titration glucose level computed as a measure of central tendency of the titration subset of small glucose measurements, wherein the measure of central tendency represents a measure of small glucose measurements for the primary time window, and
(iv) associating the titration glucose level with the measure of central tendency;
(C) adjusting or maintaining the long acting insulin medicament dosage based upon the obtained titration glucose level.

Hereby is provided a device that automatically obtains a glucose titration level which can be used as input in an algorithm for adjusting a long acting insulin dose based on the obtained glucose titration level, and wherein the evaluation of the glucose titration level is optimized with respect to characteristics of the blood glucose profile, i.e., whether the blood glucose profile indicates influence of exogenous short acting insulin or not. In other words the evaluation of the titration glucose level is automatic and it adapts to the medical regimen that the subject is following or supposed to follow. The provided device analyzes CGM data by using a set of rules, and thereby enables an automatic determination of a titration glucose level from the data stream. The value of the titration glucose level, is determined by filtering out data that is of inadequate quality, that is affected by prandial artifacts, and that is influenced by insulin on board. In this way the titration subset of small glucose measurements, wherein the small glucose measurements are small, primarily due to the influence of the long-acting insulin medicament, can be identified based on the insulin state indicator. If the insulin state indicator identifies influence by a short acting insulin the small glucose measurements, will be found in a period spaced in time from intake of carbohydrates and bolus insulin, i.e., a fasting period.

In a further aspect the obtaining the titration glucose level, in step B, further comprises:
based on the status of the insulin state indicator, selecting one of the following evaluation modes:
(B1) for the primary time window in a first evaluation mode, (i) obtaining an integer defining the number of glucose measurements to be selected for the titration subset of small glucose measurements, (ii) identifying and selecting the titration subset of small glucose measurements as a subset of smallest glucose measurements, by identifying and selecting the smallest glucose measurements within the primary time window, and ensuring that the number of measurements within the titration subset of small glucose measurements equals the obtained integer, (iii) obtaining the measure of central tendency as a first glucose measure of central tendency, and computed as a measure of central tendency of the glucose measurements within the subset of small glucose measurements, and associating the titration glucose level with the first glucose measure of central tendency,
(B2) for the primary time window in a second evaluation mode, obtaining a plurality of contemporaneously overlapping secondary time windows within the primary time window, wherein each secondary time window comprises a subset of overlapping glucose measurements being a subset of the glucose measurements in the primary time window,
for each secondary time window within the plurality of secondary time windows, computing a corresponding second glucose measure of central tendency, and thereby obtaining a plurality of second glucose measures of central tendency, wherein each respective second glucose measure of central tendency is computed as a measure of central tendency of the glucose measurements within the corresponding secondary time window, and thereby obtaining a moving or running period of a measure of central tendency across the glucose measurements in the primary time window,
for the plurality of second glucose measures of central tendency, identifying a smallest second glucose measure of central tendency as the smallest second glucose measure of central tendency within the plurality of second glucose measures of central tendency, whereby the titration subset of small glucose measurements is identified as the subset comprising the glucose measurements within the secondary time window corresponding to the smallest second glucose measure of central tendency, and
associating the titration glucose level with the smallest second glucose measure of central tendency, or
(B3) for the primary time window in a third evaluation mode, obtaining a plurality of contemporaneously overlapping secondary time windows within the primary time window, wherein each secondary time window comprises a subset of overlapping glucose measurements being a subset of the glucose measurements in the primary time window,
for each secondary time window within the plurality of secondary time windows, computing a corresponding glucose measure of variability, and thereby obtaining a plurality of glucose measures of variability, wherein each respective glucose measure of variability is computed as a measure of variability of the glucose measurements within the corresponding secondary time window, and thereby obtaining a moving period of a measure of variability across the glucose measurements in the primary time window,
for the plurality of glucose measures of variability, identifying a smallest glucose measure of variability as the smallest glucose measure of variability within the plurality of glucose measures of variability, whereby the titration subset of small glucose measurements is identified as the subset comprising the glucose measurements within the secondary time window corresponding to the smallest glucose measure of variability, and
computing a smallest third glucose measure of central tendency as a measure of central tendency of the titration subset of small glucose measurements, and
associating the titration glucose level with the smallest third glucose measure of central tendency.

In a further aspect the method further comprises:
in response to identifying the state of the insulin state indicator, selecting the first or the second evaluation mode, upon the occurrence that the state of the insulin state indicator is identified as the only-long-acting-insulin-influence state, and thereby using a preferred method for obtaining the titration glucose level, which is preferred for titration with a long acting insulin medicament, when it is ensured that no short acting insulin medicament influences the glucose measurements.

In a further aspect the method further comprises:
in response to identifying the state of the insulin state indicator,
selecting the third evaluation mode, upon the occurrence that the state of the insulin state indicator is identified as the a short-acting-insulin-influence state, and thereby using a preferred method for obtaining the titration glucose level, which is preferred for titration with a long acting insulin medicament, when it is identified that short acting insulin medicament may influence the glucose measurements.

In a further aspect, the measure of variability is the variance, and in a further aspect, the measure of central tendency is the mean value. In a further aspect, the method is repeated on a recurring basis.

In a further aspect, the method further comprises:

obtaining a second data set from one or more insulin pens used by the subject to apply the prescribed insulin regimen, the second data set comprising a plurality of insulin medicament records over the time course, each insulin medicament record in the plurality of medicament records comprising: (i) a respective insulin medicament injection event representing an insulin medicament injection into the subject using a respective insulin pen in the one or more insulin pens and (ii) a corresponding electronic timestamp that is automatically generated by the respective insulin pen upon occurrence of the respective insulin medicament injection event;

for the first glucose measures of central tendency in the first evaluation mode, associating the first glucose measure of central tendency with a tertiary time window representing an evaluation period, wherein a most recent end point of the tertiary time window is synchronized with a most recent end point of the primary time window, and wherein the primary and the tertiary windows are of the same length, for the plurality of second glucose measures of central tendency in the second evaluation mode, associating each respective second glucose measure of central tendency with a time indicator representing the time of evaluation of the respective second glucose measure of central tendency, and thereby obtaining a plurality of time indicators defining a tertiary time window representing an evaluation period, wherein a most recent end point of the tertiary time window is synchronized with a most recent end point of the primary time window, and wherein the length of the tertiary time window is smaller than the length of the primary time window, or for the plurality of glucose measures of variability in the third evaluation mode, associating each respective glucose measure of variability with a time indicator representing the time of evaluation of the respective glucose measure of variability, and thereby obtaining a plurality of time indicators defining a tertiary time window representing an evaluation period, wherein a most recent end point of the tertiary time window is synchronized with a most recent end point of the primary time window, and wherein the length of the tertiary time window is smaller than the length of the primary time window; and associating the titration glucose level with the tertiary time window;

applying a first characterization to the tertiary time window, wherein
the first characterization is one of basal regimen adherent and basal regimen nonadherent,
the tertiary time window is deemed basal regimen adherent when the second data set includes one or more medicament records that establish, on a temporal and quantitative basis, adherence with the prescribed basal insulin medicament dosage regimen during the respective tertiary time window, and
the tertiary time window is deemed basal regimen nonadherent when the second data set fails to include one or more medicament records that establish, on a temporal and quantitative basis, adherence with the prescribed basal insulin medicament dosage regimen during the tertiary time window; and wherein the adjusting the long acting insulin medicament dosage in the basal insulin medicament dosage regimen for the subject is based upon a titration glucose level that is represented by a tertiary time window that is deemed basal regimen adherent and by excluding a titration glucose level that is represented by a tertiary time window that is deemed basal regimen nonadherent.

In a further aspect, the first data structure comprises, a plurality of consecutive epochs, wherein each respective epoch is associated with a basal insulin medicament dosage, indicating when the basal insulin medicament is to be injected within the respective epoch, and how much of the basal insulin medicament is to be injected, and thereby providing a temporal and quantitative basis for the first characterization.

In a further aspect the length of the tertiary window is longer than or the same as the length of each of the epochs.

In a further aspect, the end point of the tertiary time window is synchronized with an end point of a current epoch, wherein the current epoch is the most recent completed epoch within the plurality of epochs.

In a further aspect, each respective epoch of the plurality of epochs is associated with a tertiary time window, and thereby obtaining a plurality of tertiary time windows, wherein each tertiary time window represents an evaluation period, wherein each tertiary window is aligned with the respective epoch on a temporal bases, and wherein each tertiary time window is associated with a titration glucose level.

In a further aspect, the first data structure comprises a specification of temporal and quantitative basis for administration of the long acting insulin medicament, for each of the epochs within the plurality of epochs.

In a further aspect, the quantitative basis for the long acting insulin medicament is a function of the titration glucose level.

In a further aspect, the temporal basis is specified as one injection for each epoch within the plurality of epochs.

In a further aspect each epoch in the plurality of epochs is a calendar day or a calendar week.

In a further aspect successive measurements in the plurality of glucose measurements are autonomously taken from the subject at an interval rate of 5 minutes or less, 3 minutes or less, or 1 minute or less.

In a further aspect, the device further comprises a wireless receiver, and wherein the first data set is obtained wirelessly from a glucose sensor affixed to the subject and/or the second data set is obtained wirelessly from the one or more insulin pens.

In a further aspect, the first data structure further comprises a hypoglycemic risk state indicator, wherein the hypoglycemic risk state indicator can indicate a high hypoglycemic risk state, wherein the subject may have a high hypoglycemic risk or wherein a high variability across the plurality of glucose measurements can be observed, and a non-high hypoglycemic risk state, wherein the subject may have a non-high hypoglycemic risk or wherein a low variability across the plurality of glucose measurements can be observed, and wherein the method further comprises:
in response to identifying the state of the hypoglycemic risk state indicator, selecting the first evaluation mode, upon the occurrence that the state of the hypoglycemic risk state indicator is identified as the high hypoglycemic risk state, and thereby using a method for obtaining the titration glucose level (246) which is more sensitive to low glucose values and noise.

In a further aspect, the secondary time window is 50 minutes to 70 minutes, 60 minutes to 120 minutes, 120 minutes to 180 minutes or 180 minutes to 300 minutes.

In a further aspect, successive measurements in the plurality of glucose measurements are autonomously taken from the subject at an interval rate of 4 minutes to 6 minutes, and wherein the secondary time window is 50 minutes to 70 minutes.

In a further aspect, successive measurements in the plurality of glucose measurements are autonomously taken from the subject at an interval rate of 40 minutes to 80 minutes, and wherein the secondary time window is 180 minutes to 310 minutes.

In another aspect is provided, a method for autonomously adjusting a long acting insulin medicament dosage in a prescribed insulin regimen for a subject, at a computer comprising one or more processors and a memory:
the memory storing:
a first data structure that includes the prescribed insulin regimen including a basal insulin medicament dosage regimen, wherein the basal insulin medicament dosage regimen specifies the amount of long acting insulin medicament dosage, an insulin state indicator, wherein the insulin state indicator can indicate a short-acting-insulin-influence state, wherein the glucose measurements within the primary time window may be influenced by a short acting insulin medicament, and an only-long-acting-insulin-influence state, wherein the glucose measurements within the primary time window can be influenced by a long acting insulin medicament, but the measurements cannot be influenced by a short acting insulin medicament, and the memory further storing instructions that, when executed by the one or more processors, perform a method of:
(A) obtaining, a first data set, the first data set comprising a plurality of glucose measurements of the subject taken over a time course and, for each respective glucose measurement in the plurality of glucose measurements, a corresponding timestamp representing when in the time course the respective glucose measurement was made;
(B) obtaining a titration glucose level based on small glucose measurements and the state of the insulin state indicator by:
(i) obtaining a primary time window within the time course defining the period of time comprising the glucose measurements in the first data set to be used for identifying the titration glucose level,
(ii) identifying a titration subset of small glucose measurements, identified as a subset of small glucose measurements within the primary time window,
(iii) obtaining the titration glucose level computed as a measure of central tendency of the titration subset of small glucose measurements, wherein the measure of central tendency represents a measure of small glucose measurements for the primary time window, and
(iv) associating the titration glucose level with the measure of central tendency;
(C) adjusting or maintaining the long acting insulin medicament dosage based upon the obtained titration glucose level.

In another aspect is provided a computer program comprising instructions that, when executed by a computer having one or more processors and a memory, perform the method described above.

In another aspect is provided a computer-readable data carrier having stored thereon the computer program as described above.

In another aspect is provided a device for autonomously adjusting a long acting insulin medicament dosage in a prescribed insulin regimen for a subject, wherein the device comprises one or more processors and a memory, the memory comprising:
a first data structure that includes the prescribed insulin regimen including a basal insulin medicament dosage regimen, wherein the basal insulin medicament dosage regimen specifies the amount of long acting insulin medicament dosage, and instructions that, when executed by the one or more processors, perform a method of:
(A) obtaining, a first data set, the first data set comprising a plurality of glucose measurements of the subject taken over a time course and, for each respective glucose measurement in the plurality of glucose measurements, a corresponding timestamp representing when in the time course the respective glucose measurement was made;
(B) obtaining a titration glucose level by:
(i) obtaining a primary time window within the time course defining the period of time comprising the glucose measurements in the first data set to be used for identifying the titration glucose level,
(ii) identifying a titration subset of small glucose measurements, identified as a subset of small glucose measurements within the primary time window,
(iii) obtaining the titration glucose level computed as a measure of central tendency of the titration subset of small glucose measurements, wherein the measure of central tendency represents a measure of small glucose measurements for the primary time window, and
(iv) associating the titration glucose level with the measure of central tendency;
(C) adjusting or maintaining the long acting insulin medicament dosage based upon the obtained titration glucose level.

In a further aspect of the device, the obtaining the titration glucose level, in step B, further comprises:
selecting one of the following evaluation modes:
(B1) for the primary time window in a first evaluation mode, (i) obtaining an integer defining the number of glucose measurements to be selected for the subset of glucose measurements, (ii) identifying and selecting the titration subset of small glucose measurements as a subset of smallest glucose measurements, by identifying and selecting the smallest glucose measurements within the primary time window, and ensuring that the number of measurements within the titration subset of small glucose measurements equals the obtained integer, (iii) obtaining the measure of central tendency as a first glucose measure of central tendency, and computed as a measure of central tendency of the glucose measurements within the subset of small glucose measurements, and associating the titration glucose level with the first glucose measure of central tendency, (B2) for the primary time window in a second evaluation mode, obtaining a plurality of contemporaneously overlapping secondary time windows within the primary time window, wherein each secondary time window comprises a subset of overlapping glucose measurements being a subset of the glucose measurements in the primary time window, for each secondary time window within the plurality of secondary time windows, computing a corresponding second glucose measure of central tendency, and thereby obtaining a plurality of second glucose measures of central tendency, wherein each respective second glucose measure of central tendency is computed as a measure of central tendency of the glucose measurements within the corresponding secondary time window, and thereby obtaining a moving period of a measure of central tendency across the glucose measurements in the primary time window, for the plurality of second glucose measures of central tendency, identifying a smallest second glucose measure of central tendency as the smallest second glucose measure of central tendency within the plurality of second glucose measures of central tendency, whereby the titration subset of small glucose measurements is identified as the subset comprising the glucose measurements within the secondary time window corresponding to the smallest second glucose measure of central tendency, and associating the titration glucose level with the smallest second glucose measure of central tendency, or (B3) for the primary time window in a third evaluation mode, obtaining a plurality of contemporaneously overlapping secondary time windows within the primary time window, wherein each secondary time window comprises a subset of overlapping glucose measurements being a subset of the glucose measurements in the primary time window, for each secondary time window within the plurality of secondary time windows, computing a corresponding glucose measure of variability, and thereby obtaining a plurality of glucose measures of variability, wherein each respective glucose measure of variability is computed as a measure of variability of the glucose measurements within the corresponding secondary time window, and thereby obtaining a moving period of a measure of variability across the glucose measurements in the primary time window, for the plurality of glucose measures of variability, identifying a smallest glucose measure of variability as the smallest glucose measure of variability within the plurality of glucose measures of variability, whereby the titration subset of small glucose measurements is identified as the subset comprising the glucose measurements within the secondary time window corresponding to the smallest glucose measure of variability, and computing a smallest third glucose measure of central tendency as a measure of central tendency of the titration subset of small glucose measurements, and associating the titration glucose level with the smallest third glucose measure of central tendency.

Hereby is provided a device that automatically obtain a glucose titration level which can be used as input in an algorithm for adjusting a long acting insulin dose based on the obtained glucose titration level, and wherein the evaluation of the glucose titration level can be optimized with respect characteristics of the blood glucose profile, i.e., the evaluation can be optimized if the blood glucose profile indicates influence of exogenous short acting insulin or not. In other words the evaluation of the titration glucose level is automatic and the evaluation can be made dependent on the medical regimen that the subject is following or supposed to follow.

In a further aspect the glucose measurements comprised in the titration subset of small glucose measurements have values smaller than a lower percentile of the glucose measurements, wherein the lower percentile ranges from the $0.1^{th}$ percentile to the $50^{th}$ percentile, wherein a $P^{th}$ percentile is defined as the lowest glucose measurement that is greater than P % of the glucose measurements in the first data set to be used for identifying the titration subset within the primary time window In a further aspect is provided, a basal titration adjustment device for autonomously adjusting a long acting insulin medicament dosage in a prescribed basal insulin regimen for a subject, wherein the device comprises one or more processors and a memory, the memory comprising:

a prescribed insulin regimen including a basal insulin medicament dosage regimen, wherein the basal insulin medicament dosage regimen specifies the amount of long acting insulin medicament dosage, and instructions that, when executed by the one or more processors, perform a method of:

(A) obtaining, a first data set, the first data set comprising a plurality of glucose measurements of the subject taken over a time course and, for each respective glucose measurement in the plurality of glucose measurements, a corresponding timestamp representing when in the time course the respective glucose measurement was made;

(B) obtaining a titration glucose level being the glucose level used as input to an algorithm for maintaining or adjusting the long acting insulin medicament dosage, wherein the titration glucose level is based on a titration subset of small glucose measurements, by:
(i) obtaining a primary time window within the time course defining the period of time comprising the glucose measurements in the first data set to be used for identifying the titration subset of small glucose measurements and for obtaining the titration glucose level for the primary time window, wherein each of the glucose measurements has a timestamp 232 within the primary time window,
(ii) identifying the titration subset of small glucose measurements identified as a subset of small glucose measurements within the primary time window,
(iii) obtaining the titration glucose level 246, computed as a measure of central tendency of the titration subset of small glucose measurements wherein the measure of central tendency represents a measure of small glucose measurements for the primary time window, and
(iv) associating the titration glucose level 246 with the measure of central tendency by assigning the value of measure of central tendency to the titration glucose level;

(C) adjusting or maintaining the long acting insulin medicament dosage based upon the obtained titration glucose level.

Hereby is provided a device adapted for adjusting or maintaining the long actin insulin medicament dosage based upon the obtained titration glucose level for a prescribed basal insulin regimen, i.e., the subject is treated with long acting insulin only, and we hereby know that the lowest glucose levels arise from the influence of the long acting insulin medicament.

In a further aspect, the obtaining the titration glucose level, in step B, further comprises:

selecting one of the following evaluation modes:
(B1) for the primary time window in a first evaluation mode, (i) obtaining an integer defining the number of glucose measurements to be selected for the subset of glucose measurements, (ii) identifying and selecting the titration subset of small glucose measurements as a subset of smallest glucose measurements, by identifying and selecting the smallest glucose measurements within the primary time window, and ensuring that the number of measurements within the titration subset of small glucose measurements equals the obtained integer, (iii) obtaining the measure of central tendency as a first glucose measure of central tendency, and computed as a measure of central tendency of the glucose measurements within the subset of small glucose measurements, and
associating the titration glucose level with the first glucose measure of central tendency.

In a further aspect, the obtaining the titration glucose level, in step B, further comprises:
(B2) for the primary time window in a second evaluation mode, obtaining a plurality of contemporaneously overlapping secondary time windows within the primary time window, wherein each secondary time window comprises a subset of overlapping glucose measurements being a subset of the glucose measurements in the primary time window,
for each secondary time window within the plurality of secondary time windows, computing a corresponding second glucose measure of central tendency, and thereby obtaining a plurality of second glucose measures of central tendency, wherein each respective second glucose measure of central tendency is computed as a measure of central tendency of the glucose measurements within the corresponding secondary time window, and thereby obtaining a moving period of a measure of central tendency across the glucose measurements in the primary time window,
for the plurality of second glucose measures of central tendency, identifying a smallest second glucose measure of central tendency as the smallest second glucose measure of central tendency within the plurality of second glucose measures of central tendency, whereby the titration subset of small glucose measurements is identified as the subset comprising the glucose measurements within the secondary time window corresponding to the smallest second glucose measure of central tendency, and
associating the titration glucose level with the smallest second glucose measure of central tendency.

In a further aspect, the obtaining the titration glucose level, in step B, further comprises:
obtaining a percentage defining a titration percentile defining the number of glucose measurements to be selected for the titration subset of small glucose measurements, (ii) identifying and selecting the titration subset of small glucose measurements as a subset of smallest glucose measurements, by identifying and selecting the glucose measurements defined by the titration percentile of the glucose measurements, wherein the titration percentile ranges from the $0.1^{th}$ percentile to the $50^{th}$ percentile, and is smaller than or equal to the lower percentile, and wherein a $P^{th}$ percentile is defined as the lowest glucose measurement that is greater than P % of the glucose measurements in the first data set to be used for identifying the titration subset within the primary time window, (iii) obtaining the measure of central tendency as a fourth glucose measure of central tendency, and computed as a measure of central tendency of the glucose measurements within the subset of small glucose measurements, and
associating the titration glucose level with the fourth glucose measure of central tendency, by assigning the value of the fourth measure of central tendency to the titration glucose level.

In a further aspect is provided, a basal titration adjustment device for autonomously adjusting a long acting insulin medicament dosage in a prescribed insulin regimen for a subject, wherein the device comprises one or more processors and a memory, the memory comprising:

a prescribed insulin regimen including a basal insulin medicament dosage regimen, wherein the basal insulin medicament dosage regimen specifies the amount of long acting insulin medicament dosage, and instructions that, when executed by the one or more processors, perform a method of:
(A) obtaining, a first data set, the first data set comprising a plurality of glucose measurements of the subject taken over a time course and, for each respective glucose measurement in the plurality of glucose measurements, a corresponding timestamp representing when in the time course the respective glucose measurement was made;
(B) obtaining a titration glucose level being the glucose level used as input to an algorithm for maintaining or adjusting the long acting insulin medicament dosage, wherein the titration glucose level is based on a titration subset of small glucose measurements, by:
(i) obtaining a primary time window within the time course defining the period of time comprising the glucose measurements in the first data set to be used for identifying the titration subset of small glucose measurements and for obtaining the titration glucose level for the primary time window, wherein each of the glucose measurements has a timestamp within the primary time window,
(ii) identifying the titration subset of small glucose measurements identified as a subset of small glucose measurements within the primary time window
(iii) obtaining the titration glucose level, computed as a measure of central tendency of the titration subset of small glucose measurements, wherein the measure of central tendency represents a measure of small glucose measurements for the primary time window, and
(iv) associating the titration glucose level with the measure of central tendency, by assigning the value of measure of central tendency to the titration glucose level;
(C) adjusting or maintaining the long acting insulin medicament dosage based upon the obtained titration glucose level.

BRIEF DESCRIPTION OF THE DRAWINGS

FIG. 6C illustrates the steps of identifying a titration subset of small glucose measurements within a primary time window, and the step of obtaining the corresponding glucose titration level in accordance with another embodiment of the present disclosure. The illustrated method is particularly suitable, when glucose levels are not influenced by short acting insulin.

FIGS. 7A and 7B illustrate an embodiment wherein the titration subset is identified as the lowest glucose measurements are identified within the primary window. FIGS. 7C and 7D illustrate an embodiment wherein a running average, for three different time windows (length of secondary time window), of the glucose measurements is calculated within the primary time window. A titration subset can be identified as the subset corresponding to the lowest running average, for a given time window. The identified lowest running average corresponds to the titration glucose level. FIGS. 7E and 7F illustrate an embodiment wherein a running evaluation of the variance, for three different time windows (length of secondary time window), of the glucose measurements is calculated within the primary time window. A titration subset can be identified as the subset corresponding to the lowest value of the running evaluation of the variance, for a given time window. The titration glucose level is obtained as the average glucose value of the titration subset. FIGS. 7A, 7C and 7E illustrate examples where the blood glucose in the primary window is influenced by long acting insulin only. FIGS. 7B, 7D and 7F illustrate examples where the blood glucose in the primary time window is influenced by a short acting insulin. The methods illustrated in FIGS. 7A to 7D are most suitable when the blood glucose in influenced by long acting insulin only, whereas the methods illustrated in FIG. 7E-7F is suitable when the blood glucose is influenced by short acting insulin or in similar situations wherein the variance of the blood glucose has effected to increase.

Like reference numerals refer to corresponding parts throughout the several views of the drawings.

DETAILED DESCRIPTION

Figure 1:
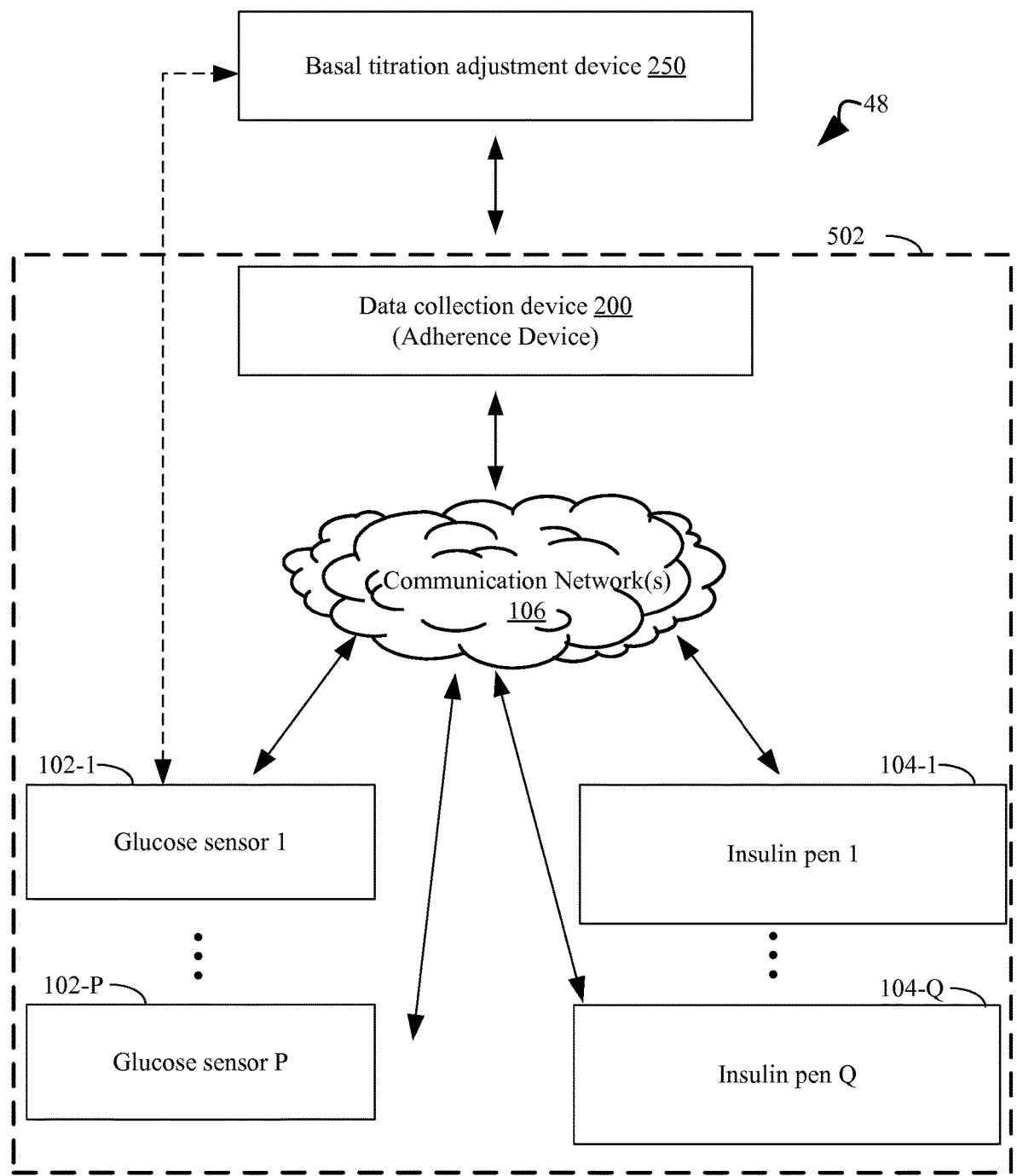
FIG. 1 illustrates an exemplary system topology that includes a basal titration adjustment device for automatically adjusting, maintaining or optimizing a long acting insulin medicament dosage in a prescribed insulin regimen for a subject, a data collection device for collecting patient data, one or more glucose sensors that measure glucose data from the subject, and one or more insulin pens that are used by the subject to inject insulin medicaments in accordance with the prescribed insulin medicament regimen, where the above-identified components are interconnected, optionally through a communications network, in accordance with an embodiment of the present disclosure.
Figure 5:
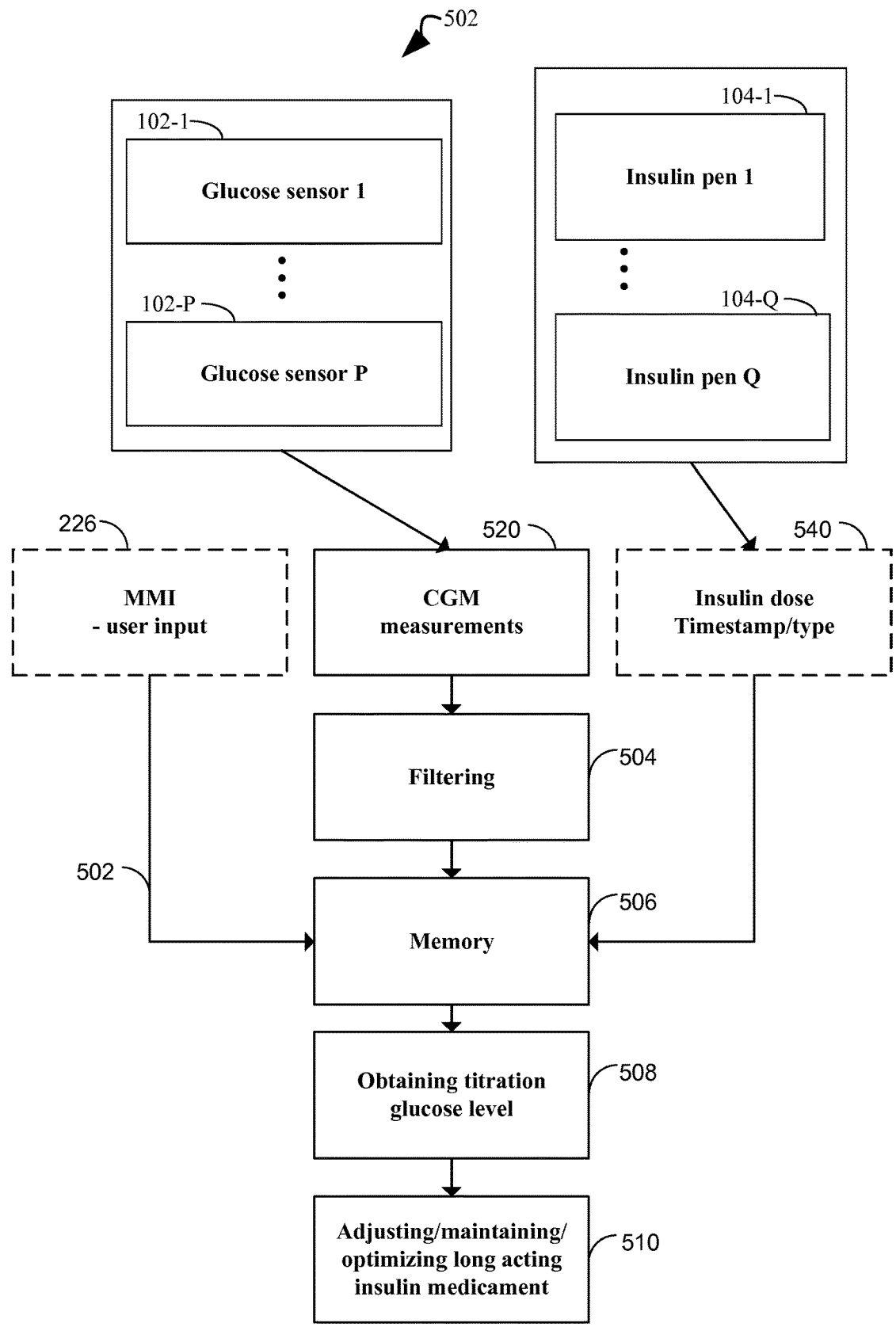
FIG. 5 illustrates an example integrated system of connected insulin pen(s), continuous glucose monitor(s), memory and a processor for autonomously adjusting a long acting insulin medicament dosage in a prescribed insulin regimen in accordance with an embodiment of the present disclosure.

The present disclosure provides robust systems and methods for autonomously adjusting a long acting insulin medicament dosage in a prescribed insulin regimen for a subject. The present disclosure relies upon the acquisition of data regarding a data set comprising a plurality of glucose measurements of a subject taken over a time course and, for each respective glucose measurement in the plurality of glucose measurements, a corresponding timestamp representing when in the time course the respective glucose measurement was made. FIG. 1 illustrates an example of an integrated system 502 for the acquisition of such data, and FIG. 5 provides more details of such a system 502. The integrated system 502 includes one or more connected insulin pens 104, one or more glucose monitors or glucose sensors 102, memory 506, and a processor (not shown) for performing algorithmic categorization of autonomous glucose data of a subject. In some embodiments, a glucose monitor 102 is a continuous glucose monitor.

With the integrated system 502, autonomous timestamped glucose measurements of the subject are obtained 520. Also, in some embodiments, data from the one or more insulin pens 104 used to apply a prescribed insulin regimen to the subject is obtained 540 as a plurality of records. Each record comprises a timestamped event specifying an amount of injected insulin medicament that the subject received as part of the prescribed insulin medicament dosage regimen. The glucose measurements are filtered 504 and stored in non-transitory memory 506. The plurality of glucose measurements of the subject taken over a time are used to determine a titration glucose level of the subject 508. In this way, the glucose data is analyzed to adjust the long acting insulin medicament dosage based upon a the titration glucose level in accordance with the methods of the present disclosure 510.

Reference will now be made in detail to embodiments, examples of which are illustrated in the accompanying drawings. In the following detailed description, numerous specific details are set forth in order to provide a thorough understanding of the present disclosure. However, it will be apparent to one of ordinary skill in the art that the present disclosure may be practiced without these specific details. In other instances, well-known methods, procedures, components, circuits, and networks have not been described in detail so as not to unnecessarily obscure aspects of the embodiments.

It will also be understood that, although the terms first, second, etc. may be used herein to describe various elements, these elements should not be limited by these terms. These terms are only used to distinguish one element from another. For example, a first subject could be termed a second subject, and, similarly, a second subject could be termed a first subject, without departing from the scope of the present disclosure. The first subject and the second subject are both subjects, but they are not the same subject. Furthermore, the terms "subject" and "user" are used interchangeably herein. By the term insulin pen is meant an injection device suitable for applying discrete doses of insulin, and wherein the injection device is adapted for logging and communicating dose related data.

The terminology used in the present disclosure is for the purpose of describing particular embodiments only and is not intended to be limiting of the invention. As used in the description of the invention and the appended claims, the singular forms "a", "an" and "the" are intended to include the plural forms as well, unless the context clearly indicates otherwise. It will also be understood that the term "and/or" as used herein refers to and encompasses any and all possible combinations of one or more of the associated listed items. It will be further understood that the terms "comprises" and/or "comprising," when used in this specification, specify the presence of stated features, integers, steps, operations, elements, and/or components, but do not preclude the presence or addition of one or more other features, integers, steps, operations, elements, components, and/or groups thereof.

As used herein, the term "if" may be construed to mean "when" or "upon" or "in response to determining" or "in response to detecting," depending on the context. Similarly, the phrase "if it is determined" or "if [a stated condition or event] is detected" may be construed to mean "upon determining" or "in response to determining" or "upon detecting [the stated condition or event]" or "in response to detecting [the stated condition or event]," depending on the context.

A detailed description of a system 48 for adjusting a long acting insulin medicament dosage 216 in a prescribed insulin regimen for a subject in accordance with the present disclosure is described in conjunction with FIGS. 1 through 3. As such, FIGS. 1 through 3 collectively illustrate the topology of the system in accordance with the present disclosure. In the topology, there is a basal titration adjustment device for autonomously adjusting a long acting insulin medicament dosage in a prescribed insulin regimen for a subject ("basal titration adjustment device 250") (FIGS. 1, 2, and 3), a device for data collection ("data collection device 200"), one or more glucose sensors 102 associated with the subject (FIGS. 1 and 5), and one or more insulin pens 104 for injecting insulin medicaments into the subject (FIGS. 1 and 5). Throughout the present disclosure, the data collection device 200 and the basal titration adjustment device 250 will be referenced as separate devices solely for purposes of clarity. That is, the disclosed functionality of the data collection device 200 and the disclosed functionality of the basal titration adjustment device 250 are contained in separate devices as illustrated in FIG. 1. However, it will be appreciated that, in fact, in some embodiments, the disclosed functionality of the data collection device 200 and the disclosed functionality of the basal titration adjustment device 250 are contained in a single device. In some embodiments, the disclosed functionality of the data collection device 200 and/or the disclosed functionality of the basal titration adjustment device 250 are contained in a single device and this single device is a glucose monitor 102 or the insulin pen 104.

Referring to FIG. 1, the basal titration adjustment device 250 autonomously adjusts a long acting insulin medicament dosage in a prescribed insulin regimen for a subject. To do this, the data collection device 200, which is in electrical communication with the basal titration adjustment device 250, receives autonomous glucose measurements originating from one or more glucose sensors 102 attached to a subject on an ongoing basis. In some embodiments, the data collection device 200 also receives insulin medicament injection data from one or more insulin pens 104 used by the subject to inject insulin medicaments. In some embodiments, the data collection device 200 receives such data directly from the glucose sensor(s) 102 and insulin pens 104 used by the subject. For instance, in some embodiments the data collection device 200 receives this data wirelessly through radio-frequency signals. In some embodiments such signals are in accordance with an 802.11 (WiFi), Bluetooth, or ZigBee standard. In some embodiments, the data collection device 200 receives such data directly, analyzes the data, and passes the analyzed data to the basal titration adjustment device 250. In some embodiments, a glucose sensor 102 and/or insulin pen 104 includes an RFID tag and communicates to the data collection device 200 and/or the basal titration adjustment device 250 using RFID communication. In some embodiments, the data collection device 200 also obtains or receives physiological measurements 247 of the subject (e.g., from wearable physiological measurement devices, from measurement devices within the data collection device 200 such as a magnetometer or thermostat, etc).

In some embodiments, the data collection device 200 and/or the basal titration adjustment device 250 is not proximate to the subject and/or does not have wireless capabilities or such wireless capabilities are not used for the purpose of acquiring glucose data, insulin medicament injection data, and/or physiological measurement data. In such embodiments, a communication network 106 may be used to communicate glucose measurements from the glucose sensor 102 to the data collection device 200 and/or the basal titration adjustment device 250, insulin medicament injection data from the one or more insulin pens 104 to the data collection device 200 and/or the basal titration adjustment device 250, and/or physiological measurement data from one or more physiological measurement devices (not shown) to the data collection device 200 and/or the basal titration adjustment device 250.

Examples of networks 106 include, are, but not limited to, the World Wide Web (WWW), an intranet and/or a wireless network, such as a cellular telephone network, a wireless local area network (LAN) and/or a metropolitan area network (MAN), and other devices by wireless communication. The wireless communication optionally uses any of a plurality of communications standards, protocols and technologies, including but not limited to Global System for Mobile Communications (GSM), Enhanced Data GSM Environment (EDGE), high-speed downlink packet access (HSDPA), high-speed uplink packet access (HSUPA), Evolution, Data-Only (EV-DO), HSPA, HSPA+, Dual-Cell HSPA (DC-HSPDA), long term evolution (LTE), near field communication (NFC), wideband code division multiple access (W-CDMA), code division multiple access (CDMA), time division multiple access (TDMA), Bluetooth, Wireless Fidelity (Wi-Fi) (e.g., IEEE 802.11a, IEEE 802.11ac, IEEE 802.11ax, IEEE 802.11b, IEEE 802.11g and/or IEEE 802.11n), voice over Internet Protocol (VoIP), Wi-MAX, a protocol for e-mail (e.g., Internet message access protocol (IMAP) and/or post office protocol (POP)), instant messaging (e.g., extensible messaging and presence protocol (XMPP), Session Initiation Protocol for Instant Messaging and Presence Leveraging Extensions (SIMPLE), Instant Messaging and Presence Service (IMPS)), and/or Short Message Service (SMS), or any other suitable communication protocol, including communication protocols not yet developed as of the filing date of the present disclosure.

In some embodiments, there is a single glucose sensor 102 attached to the subject and the data collection device 200 and/or the basal titration adjustment device 250 is part of the glucose sensor 102. That is, in some embodiments, the data collection device 200 and/or the basal titration adjustment device 250 and the glucose sensor 102 are a single device.

In some embodiments, the data collection device 200 and/or the basal titration adjustment device 250 is part of an insulin pen. That is, in some embodiments, the data collection device 200 and/or the basal titration adjustment device 250 and an insulin pen 104 are a single device.

Of course, other topologies of the system 48 are possible. For instance, rather than relying on a communications network 106, the one or more glucose sensors 102 and the one or more insulin pens 104 may wirelessly transmit information directly to the data collection device 200 and/or basal titration adjustment device 250. Further, the data collection device 200 and/or the basal titration adjustment device 250 may constitute a portable electronic device, a server computer, or in fact constitute several computers that are linked together in a network or be a virtual machine in a cloud computing context. As such, the exemplary topology shown in FIG. 1 merely serves to describe the features of an embodiment of the present disclosure in a manner that will be readily understood to one of skill in the art.

Referring to FIGS. 2A, 2B, 2C and 2D, in typical embodiments, the basal titration adjustment device 250 comprises one or more computers. For purposes of illustration in FIG. 2A, the basal titration adjustment device 250 is represented as a single computer that includes all of the functionality for autonomously adjusting a long acting insulin medicament dosage in a prescribed insulin regimen for a subject. However, the disclosure is not so limited. In some embodiments, the functionality for autonomously adjusting a long acting insulin medicament dosage in a prescribed insulin regimen for a subject is spread across any number of networked computers and/or resides on each of several networked computers and/or is hosted on one or more virtual machines at a remote location accessible across the communications network 106. One of skill in the art will appreciate that any of a wide array of different computer topologies are used for the application and all such topologies are within the scope of the present disclosure.

Turning to FIG. 2 with the foregoing in mind, an exemplary basal titration adjustment device 250 for autonomously adjusting a long acting insulin medicament dosage in a prescribed insulin regimen for a subject comprises one or more processing units (CPU's) 274, a network or other communications network interface 284, a memory 192 (e.g., random access memory), one or more magnetic disk storage and/or persistent devices 290 optionally accessed by one or more controllers 288, one or more communication busses 213 for interconnecting the aforementioned components, and a power supply 276 for powering the aforementioned components. In some embodiments, data in memory 192 is seamlessly shared with non-volatile memory 290 using known computing techniques such as caching. In some embodiments, memory 192 and/or memory 290 includes mass storage that is remotely located with respect to the central processing unit(s) 274. In other words, some data stored in memory 192 and/or memory 290 may in fact be hosted on computers that are external to the basal titration adjustment device 250 but that can be electronically accessed by the basal titration adjustment device 250 over an Internet, intranet, or other form of network or electronic cable (illustrated as element 106 in FIG. 2) using network interface 284.

In some embodiments, the memory 192 of the basal titration adjustment device 250 for autonomously adjusting a long acting insulin medicament dosage in a prescribed insulin regimen for a subject stores:

an operating system 202 that includes procedures for handling various basic system services;
a basal titration adjustment module 204;
a first data structure 210, the first data structure comprising a prescribed insulin regimen 212 for the subject comprising a basal insulin medicament dosage regimen 214. Optionally, the basal insulin medicament dosage regimen 214 comprises a long acting insulin medicament dosage indicator 2116 and an associated epoch 218. The indicator 216 indicates, when the basal insulin medicament is to be injected within the associated epoch 218. Also optionally, the prescribed insulin regimen comprises an insulin state indicator 211, wherein the insulin state indicator 211 can indicate a short-acting-insulin-influence state, wherein the glucose measurements may be influenced by a short acting insulin medicament, and an only-long-acting-insulin-influence state, wherein the glucose measurements can be influenced by a long acting insulin medicament only, and the glucose measurements cannot be influenced by a short acting insulin medicament;
a first data set 220, the first data set representing a time course and comprising a plurality of glucose measurements of the subject over the time course, and for each respective glucose measurement 230 in the plurality of glucose measurements, a timestamp 232 representing when the respective glucose measurement was made;
a primary time window 233 defined within the time course, and thereby comprising a glucose measurements 236 from the first data set 220, the primary time window further comprises a submodule SM1 247, SM2 248 or SM3 275 defining further data structures used to identify a titration subset of small glucose measurements (240, 269, 273), and to obtain a glucose titration level 246 associated with the primary time window 233;
submodule SM1 247 comprises an integer 234 defining the number of glucose measurements to be selected for a titration subset of small glucose measurements 240, the titration subset of small glucose measurements 240 being a subset of smallest glucose measurements within the primary time window 233. The submodule further comprises a first glucose measure of central tendency 244 being a measure of central tendency of the titration subset of small glucose measurements 240. The titration glucose level 246 is to be associated with the first glucose measure of central tendency;

submodule SM2 248 defines a plurality of contemporaneously overlapping secondary time windows 260, wherein each secondary time window 262 comprises glucose measurements 266 defining a subset of overlapping glucose measurements 264 within the primary time window and a second glucose measure of central tendency being the measure of central tendency of the corresponding subset of overlapping glucose measurements, whereby the submodule defines a plurality of second glucose measures of central tendency. The submodule further defines a smallest second glucose measure of central tendency 268 being the smallest second glucose measure of central tendency within the plurality of second glucose measures of central tendency. The titration glucose level 246 is to be associated with smallest second glucose measure of central tendency 268;

submodule SM3 275 comprises a plurality of contemporaneously overlapping secondary time windows 260 within the primary time window 233, wherein each secondary time window 262 comprises a subset of overlapping glucose measurements 264 defining a subset of the glucose measurements 236 within the primary time window 233 and a glucose measure of variability 271 being a measure of variability of the corresponding subset of overlapping glucose measurements 264, and thereby obtaining a plurality of glucose measures of variability, whereby the submodule defines a plurality of glucose measure of variability. The submodule 275 further comprises a smallest glucose measure of variability 272 being the smallest glucose measure of variability within the plurality of glucose measures of variability, and a titration subset of small glucose measurements 273 being the subset comprising the glucose measurements within the secondary time window 262 corresponding to the smallest glucose measure of variability 272. The submodule further comprises a smallest third glucose measure of central tendency 274 being a measure of central tendency of the titration subset of small glucose measurements 273. The titration glucose level 246 is to be associated with the smallest third glucose measure of central tendency 274.

In some embodiments, the basal titration adjustment module 204 is accessible within any browser (phone, tablet, laptop/desktop). In some embodiments the basal titration adjustment module 204 runs on native device frameworks, and is available for download onto the basal titration adjustment device 250 running an operating system 202 such as Android or iOS.

In some implementations, one or more of the above identified data elements or modules of the basal titration adjustment device 250 for autonomously adjusting a long acting insulin medicament dosage in a prescribed insulin regimen for a subject are stored in one or more of the previously described memory devices, and correspond to a set of instructions for performing a function described above. The above-identified data, modules or programs (e.g., sets of instructions) need not be implemented as separate software programs, procedures or modules, and thus various subsets of these modules may be combined or otherwise re-arranged in various implementations. In some implementations, the memory 192 and/or 290 optionally stores a subset of the modules and data structures identified above. Furthermore, in some embodiments the memory 192 and/or 290 stores additional modules and data structures not described above.

In some embodiments, a basal titration adjustment device 250 for autonomously adjusting a long acting insulin medicament dosage 216 in a prescribed insulin regimen 212 for a subject is a smart phone (e.g., an iPHONE), laptop, tablet computer, desktop computer, or other form of electronic device (e.g., a gaming console). In some embodiments, the basal titration adjustment device 250 is not mobile. In some embodiments, the basal titration adjustment device 250 is mobile.

FIGS. 3A, 3B, 3C and 3D provides a further description of a specific embodiment of a basal titration adjustment device 250 that can be used with the instant disclosure. The basal titration adjustment device 250 illustrated in FIG. 3A through 3D has one or more processing units (CPU's) 274, peripherals interface 370, memory controller 368, a network or other communications interface 284, a memory 192 (e.g., random access memory), a user interface 278, the user interface 278 including a display 282 and input 280 (e.g., keyboard, keypad, touch screen), an optional accelerometer 317, an optional GPS 319, optional audio circuitry 372, an optional speaker 360, an optional microphone 362, one or more optional intensity sensors 364 for detecting intensity of contacts on the basal titration adjustment device 250 (e.g., a touch-sensitive surface such as a touch-sensitive display system 282 of the basal titration adjustment device 250), an optional input/output (I/O) subsystem 366, one or more optional optical sensors 373, one or more communication busses 213 for interconnecting the aforementioned components, and a power supply 276 for powering the aforementioned components.

In some embodiments, the input 280 is a touch-sensitive display, such as a touch-sensitive surface. In some embodiments, the user interface 278 includes one or more soft keyboard embodiments. The soft keyboard embodiments may include standard (QWERTY) and/or non-standard configurations of symbols on the displayed icons.

The basal titration adjustment device 250 illustrated in FIG. 3 optionally includes, in addition to accelerometer(s) 317, a magnetometer (not shown) and a GPS 319 (or GLONASS or other global navigation system) receiver for obtaining information concerning the location and orientation (e.g., portrait or landscape) of the basal titration adjustment device 250 and/or for determining an amount of physical exertion by the subject.

It should be appreciated that the basal titration adjustment device 250 illustrated in FIG. 3 is only one example of a multifunction device that may be used for autonomously adjusting a long acting insulin medicament dosage (216) in a prescribed insulin regimen for a subject, and that the basal titration adjustment device 250 optionally has more or fewer components than shown, optionally combines two or more components, or optionally has a different configuration or arrangement of the components. The various components shown in FIG. 3 are implemented in hardware, software, firmware, or a combination thereof, including one or more signal processing and/or application specific integrated circuits.

Memory 192 of the basal titration adjustment device 250 illustrated in FIG. 3 optionally includes high-speed random access memory and optionally also includes non-volatile memory, such as one or more magnetic disk storage devices, flash memory devices, or other non-volatile solid-state memory devices. Access to memory 192 by other components of the basal titration adjustment device 250, such as CPU(s) 274 is, optionally, controlled by the memory controller 368.

In some embodiments, the memory 192 of the basal titration adjustment device 250 illustrated in FIG. 3 optionally includes a third data set 246 comprising a plurality of physiological measurements, and each such physiological measurement 247 includes a measurement value 248. In some embodiments, the physiological measurement 247 is body temperature of the subject. In some embodiments, the physiological measurement 247 is a measurement of activity of the subject. In some embodiments, these physiological measurements serve as an additional glycaemic risk measure. In some embodiments, the optional accelerometer 317, optional GPS 319, and/or magnetometer (not shown) of the basal titration adjustment device 250 or such components optionally within the one or more glucose monitors 102 and/or the one or more pens 104 is used to acquire such physiological measurements 247.

The peripherals interface 370 can be used to couple input and output peripherals of the device to CPU(s) 274 and memory 192. The one or more processors 274 run or execute various software programs and/or sets of instructions stored in memory 192, such as the insulin regimen monitoring module 204, to perform various functions for the basal titration adjustment device 250 and to process data.

In some embodiments, the peripherals interface 370, CPU(s) 274, and memory controller 368 are, optionally, implemented on a single chip. In some other embodiments, they are, optionally, implemented on separate chips.

RF (radio frequency) circuitry of network interface 284 receives and sends RF signals, also called electromagnetic signals. In some embodiments, the first data structure 210, the first data set 228, the optional second data set 320 is received using this RF circuitry from one or more devices such as a glucose sensor 102 associated with a subject, an insulin pen 104 associated with the subject and/or the data collection device 200. In some embodiments, the RF circuitry 108 converts electrical signals to/from electromagnetic signals and communicates with communications networks and other communications devices, glucose sensors 102, and insulin pens 104 and/or the data collection device 200 via the electromagnetic signals. The RF circuitry 284 optionally includes well-known circuitry for performing these functions, including but not limited to an antenna system, an RF transceiver, one or more amplifiers, a tuner, one or more oscillators, a digital signal processor, a CODEC chipset, a subscriber identity module (SIM) card, memory, and so forth. RF circuitry 284 optionally communicates with the communication network 106. In some embodiments, the circuitry 284 does not include RF circuitry and, in fact, is connected to the network 106 through one or more hard wires (e.g., an optical cable, a coaxial cable, or the like).

In some embodiments, the audio circuitry 372, the optional speaker 360, and the optional microphone 362 provide an audio interface between the subject and the basal titration adjustment device 250. The audio circuitry 372 receives audio data from peripherals interface 370, converts the audio data to electrical signals, and transmits the electrical signals to speaker 360. The speaker 360 converts the electrical signals to human-audible sound waves. The audio circuitry 372 also receives electrical signals converted by the microphone 362 from sound waves. The audio circuitry 372 converts the electrical signal to audio data and transmits the audio data to peripherals interface 370 for processing. Audio data is, optionally, retrieved from and/or transmitted to the memory 192 and/or the RF circuitry 284 by the peripherals interface 370.

In some embodiments, the power supply 276 optionally includes a power management system, one or more power sources (e.g., battery, alternating current (AC)), a recharging system, a power failure detection circuit, a power converter or inverter, a power status indicator (e.g., a light-emitting diode (LED)) and any other components associated with the generation, management and distribution of power in portable devices.

In some embodiments, the basal titration adjustment device 250 optionally also includes one or more optical sensors 373. The optical sensor(s) 373 optionally include charge-coupled device (CCD) or complementary metal-oxide semiconductor (CMOS) phototransistors. The optical sensor(s) 373 receive light from the environment, projected through one or more lens, and converts the light to data representing an image. The optical sensor(s) 373 optionally capture still images and/or video. In some embodiments, an optical sensor is located on the back of the basal titration adjustment device 250, opposite the display 282 on the front of the basal titration adjustment device 250, so that the input 280 is enabled for use as a viewfinder for still and/or video image acquisition. In some embodiments, another optical sensor 373 is located on the front of the basal titration adjustment device 250 so that the subject's image is obtained (e.g., to verify the health or condition of the subject, to determine the physical activity level of the subject, or to help diagnose a subject's condition remotely, to acquire visual physiological measurements 247 of the subject, etc.).

As illustrated in FIG. 3, a basal titration adjustment device 250 preferably comprises an operating system 202 that includes procedures for handling various basic system services. The operating system 202 (e.g., iOS, DARWIN, RTXC, LINUX, UNIX, OS X, WINDOWS, or an embedded operating system such as VxWorks) includes various software components and/or drivers for controlling and managing general system tasks (e.g., memory management, storage device control, power management, etc.) and facilitates communication between various hardware and software components.

In some embodiments the basal titration adjustment device 250 is a smart phone. In other embodiments, the basal titration adjustment device 250 is not a smart phone but rather is a tablet computer, desktop computer, emergency vehicle computer, or other form or wired or wireless networked device. In some embodiments, the basal titration adjustment device 250 has any or all of the circuitry, hardware components, and software components found in the basal titration adjustment device 250 depicted in FIG. 2 or 3. In the interest of brevity and clarity, only a few of the possible components of the basal titration adjustment device 250 are shown in order to better emphasize the additional software modules that are installed on the basal titration adjustment device 250.

In some embodiments, and as illustrated in FIG. 3A through 3D, the memory 192 of the basal titration adjustment device 250 for autonomously adjusting a long acting insulin medicament dosage in a prescribed insulin regimen for a subject further stores:

a second data set 320 obtained from one or more insulin pens 104 used by the subject to apply the prescribed insulin regimen, the second data set comprising a plurality of insulin medicament records over the time course, each insulin medicament record 321 in the plurality of medicament records comprising: (i) a respective insulin medicament injection event 322 representing an insulin medicament injection into the subject using a respective insulin pen in the one or more insulin pens 104 and (ii) a corresponding electronic timestamp 323 that is automatically generated by the respective insulin pen upon occurrence of the respective insulin medicament injection event; and for each first glucose measures of central tendency 244 is associated a tertiary time window 330 representing an evaluation period, for the plurality of second glucose measures of central tendency, each respective second glucose measure of central tendency 267 is associated with a time indicator 331 representing the time of evaluation of the respective second glucose measure of central tendency, and thereby obtaining a plurality of time indicators defining a tertiary time window 330 representing an evaluation period, or for the plurality of glucose measures of variability in the third evaluation mode, each respective glucose measure of variability 267 is associated with a time indicator 331 representing the time of evaluation of the respective glucose measure of variability, and thereby obtaining a plurality of time indicators defining a tertiary time window 330 representing an evaluation period; and the titration glucose level 246 is associated with the tertiary time window 330;

a first characterization 335 applied to the tertiary time window 330, wherein the first characterization 335 is one of basal regimen adherent and basal regimen nonadherent, the tertiary time window 330 is deemed basal regimen adherent when the second data set 320 includes one or more medicament records that establish, on a temporal and quantitative basis, adherence with the prescribed basal insulin medicament dosage regimen 212 during the respective tertiary time window 330, and the tertiary time window is deemed basal regimen nonadherent when the second data set 320 fails to include one or more medicament records that establish, on a temporal and quantitative basis, adherence with the prescribed basal insulin medicament dosage regimen 212 during the tertiary time window 330.

While the system 48 disclosed in FIG. 1 can work standalone, in some embodiments it can also be linked with electronic medical records to exchange information in any way.

Now that details of a system 48 for autonomously adjusting a long acting insulin medicament dosage in a prescribed insulin regimen for a subject have been disclosed, details regarding a flow chart of processes and features of the system, in accordance with an embodiment of the present disclosure, are disclosed with reference to FIGS. 4A through 4E. In some embodiments, such processes and features of the system are carried out by the basal titration adjustment module 204 illustrated in FIGS. 2 and 3.

Block 402. Block 402 illustrates the beginning of the process.

Block 410. With reference to block 410 of FIG. 4A, the goal of insulin therapy in subjects with either type 1 diabetes mellitus or type 2 diabetes mellitus is to match as closely as possible normal physiologic insulin secretion to control fasting and postprandial plasma glucose. As illustrated in FIG. 2, a basal titration adjustment device 250 comprises one or more processors 274 and a memory 192/290. The memory stores instructions that, when executed by the one or more processors, perform a method. In the method, a first data set 228 is obtained. The first data set 228 comprises glucose measurements 230 of the subject from one or more glucose sensors 102. FIG. 2 illustrates. Each such glucose measurement 230 is timestamped with a glucose measurement timestamp 232 to represent when the respective measurement was made.

In some embodiments, the glucose measurements 230 are autonomously measured. The FREESTYLE LIBRE CGM by ABBOTT ("LIBRE") is an example of a glucose sensor that may be used as a glucose sensor 102 in order to make autonomous glucose measurements of a subject. The LIBRE allows calibration-free glucose measurements with an on-skin coin-sized sensor, which can send up to eight hours of data to a reader device (e.g., the data collection device 200 and/or the basal titration adjustment device 250) via near field communications, when brought close together. The LIBRE can be worn for fourteen days in all daily life activities. Referring to block 410, in some embodiments, the glucose measurements are taken from the subject at an interval rate of 5 minutes or less, 3 minutes or less, or 1 minute or less. In some embodiments, the glucose measurements are taken from the subject at an interval rate of 5 minutes or less, 3 minutes or less, or 1 minute or less, over a time period of a day or more, two days or more, a week or more, or two weeks or more. In some embodiments, the glucose measurements are autonomously taken (e.g., without human effort, without human intervention, etc.). In some embodiments, the glucose measurements are manually taken (e.g., with manual human effort, with human intervention, etc.).

The basal titration adjustment device 250 accesses and/or stores a first data structure 210 that includes the prescribed insulin regimen 212 including a basal insulin medicament dosage regimen 214, wherein the basal insulin medicament dosage regimen specifies the amount of long acting insulin medicament dosage 216, an insulin state indicator 211, wherein the insulin state indicator 211 can indicate a short-acting-insulin-influence state, wherein the glucose measurements within the primary time window may be influenced by a short acting insulin medicament, and an only-long-acting-insulin-influence state, wherein the glucose measurements within the primary time window can be influenced by a long acting insulin medicament, but the glucose measurements cannot be influenced by a short acting insulin medicament.

In some embodiments, the long acting insulin medicament specified by the basal insulin medicament dosage regimen 214 consists of a single insulin medicament having a duration of action that is between 12 and 24 hours or a mixture of insulin medicaments that collectively have a duration of action that is between 12 and 24 hours. Examples of such long acting insulin medicaments include, but are not limited to Insulin Degludec (developed by NOVO NORDISK under the brand name Tresiba), NPH (Schmid, 2007, "New options in insulin therapy. J Pediatria (Rio J). 83(Suppl 5): S146-S155), Glargine (LANTUS, Mar. 2, 2007, insulin glargine [rDNA origin] injection, [prescribing information], Bridgewater, N.J.: Sanofi-Aventis), and Determir (Plank et al., 2005, "A double-blind, randomized, dose-response study investigating the pharmacodynamic and pharmacokinetic properties of the long-acting insulin analog detemir," Diabetes Care 28:1107-1112).

In some embodiments, the prescribed regimen may also comprise a bolus insulin medicament dosage regimen specifying the amount of short acting insulin medicament dosage. The short acting insulin medicament specified by the bolus insulin medicament dosage regimen comprises a single insulin medicament having a duration of action that is between three to eight hours or a mixture of insulin medicaments that collectively have a duration of action that is between three to eight hours. Examples of such short acting insulin medicaments include, but are not limited, to Lispro (HUMALOG, May 18, 2001, insulin lispro [rDNA origin] injection, [prescribing information], Indianapolis, Ind.: Eli Lilly and Company), Aspart (NOVOLOG, July 2011, insulin aspart [rDNA origin] injection, [prescribing information], Princeton, N.J., NOVO NORDISK Inc., July, 2011), Glulisine (Helms Kelley, 2009, "Insulin glulisine: an evaluation of its pharmacodynamic properties and clinical application," Ann Pharmacother 43:658-668), and Regular (Gerich, 2002, "Novel insulins: expanding options in diabetes management," Am J Med. 113:308-316).

Block 420. Referring to block 410 of FIG. 4A, the method continues with the process step (b) of obtaining a titration glucose level 246 based on small glucose measurements and the state of the insulin state indicator 211.

Block 422. Referring to block 422 of FIG. 4A, the method continues with (i) obtaining a primary time window 233 within the time course defining the period of time comprising the glucose measurements 236 in the first data set to be used for identifying the titration glucose level.

Block 424. Referring to block 424 of FIG. 4A, the method continues with (ii) identifying a titration subset of small glucose measurements 240, 269, 273, identified as a subset of small glucose measurements within the primary time window 233.

Block 426. Referring to block 426 of FIG. 4A, the method continues with (iii) obtaining the titration glucose level 246 computed as a measure of central tendency 244, 268, 274 of the titration subset of small glucose measurements 240, 269, 273, wherein the measure of central tendency represents a measure of small glucose measurements for the primary time window.

Block 428. Referring to block 428 of FIG. 4A, the method continues with (iv) associating the titration glucose level 246 with the measure of central tendency 244, 268, 274, and thereby completing the process step (b) of obtaining the titration glucose level.

Block 440. Referring to block 440 of FIG. 4A, the method continues with the process step (C) of adjusting or maintaining the long acting insulin medicament dosage 216 based upon the obtained titration glucose level 246.

Block 404. Block 404 illustrates the end of the process.

Figure 4A:
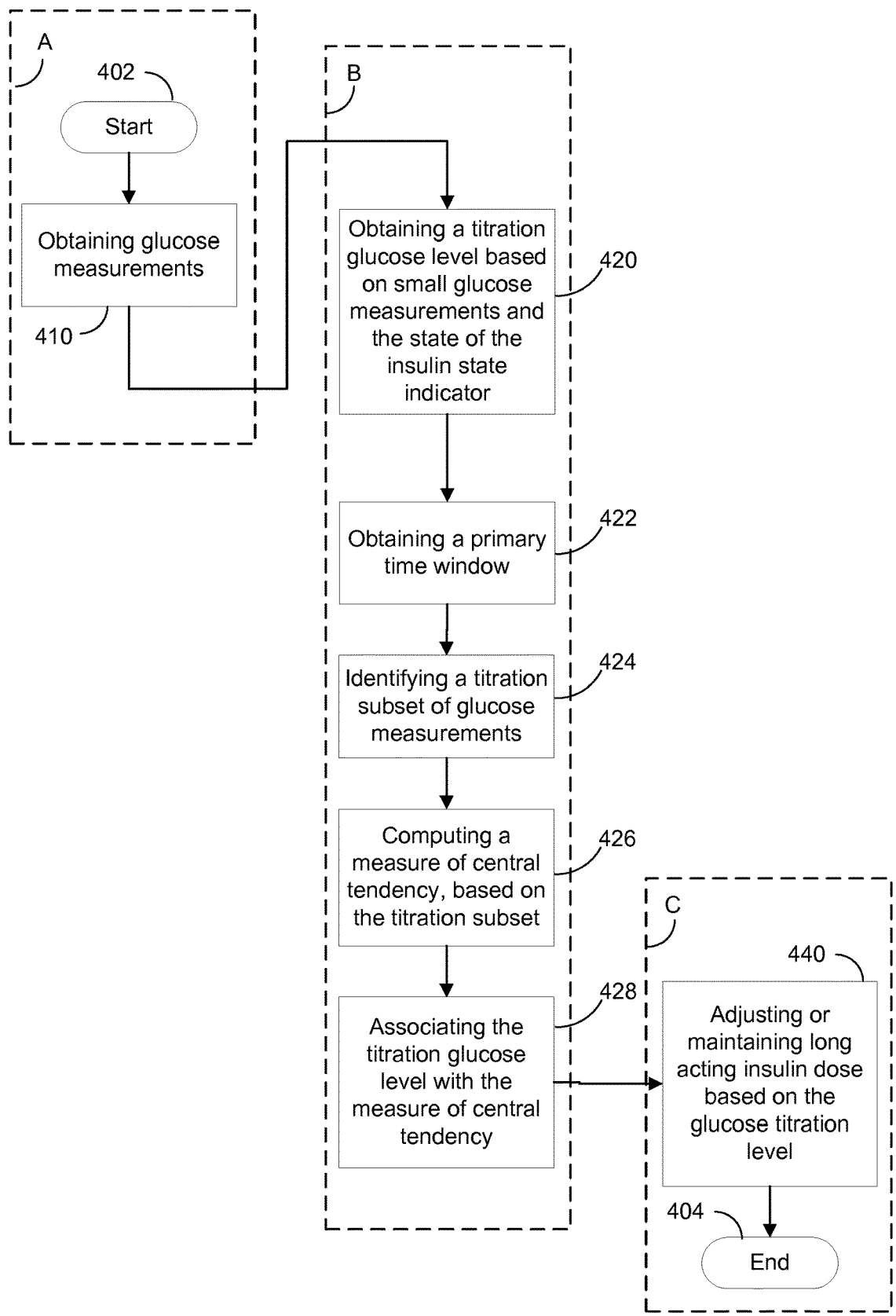
FIGS. 4A, 4B, 4C, and 4D collectively provide a flow chart of processes and features of a basal titration adjustment device for autonomously adjusting a long acting insulin medicament dosage in a prescribed insulin regimen in accordance with various embodiments of the present disclosure.

As appears from FIG. 4A the method can be divided into the overall steps: step A wherein the glucose measurements are obtained, step B wherein the titration glucose level is obtained, and step C wherein the long acting insulin is adjusted based on the glucose titration level.

Figure 4B:
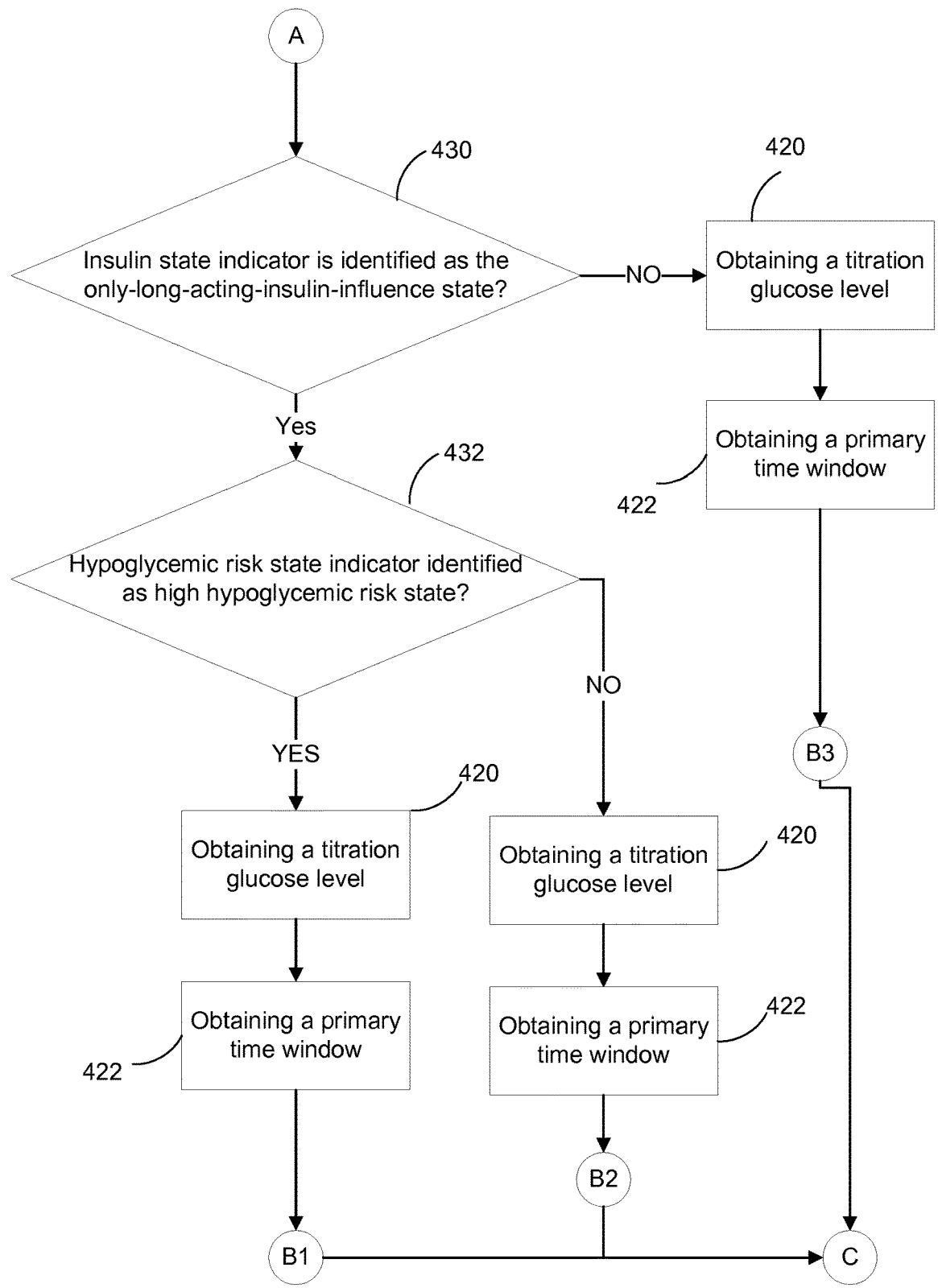
Figure 4C:
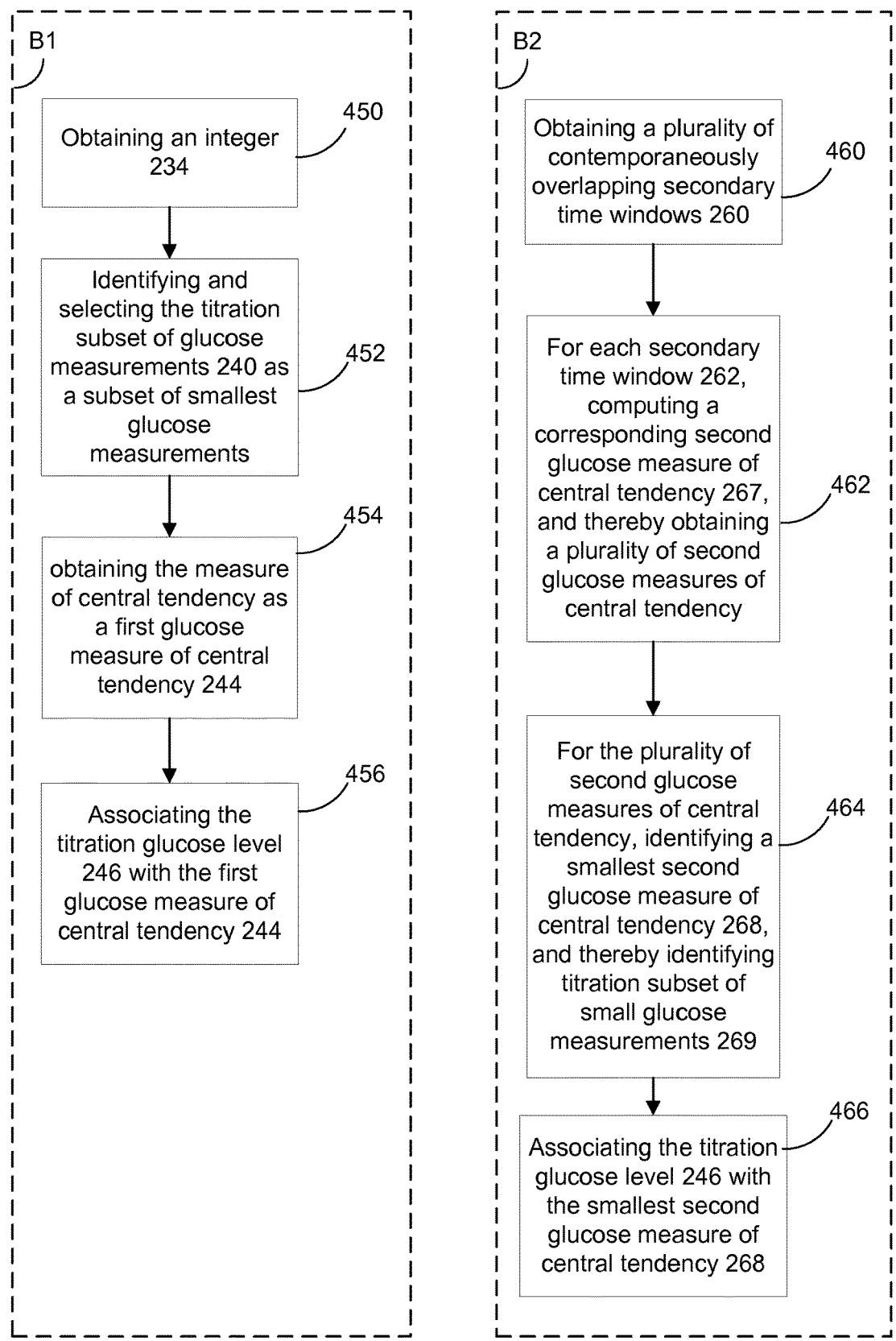
Figure 4D:
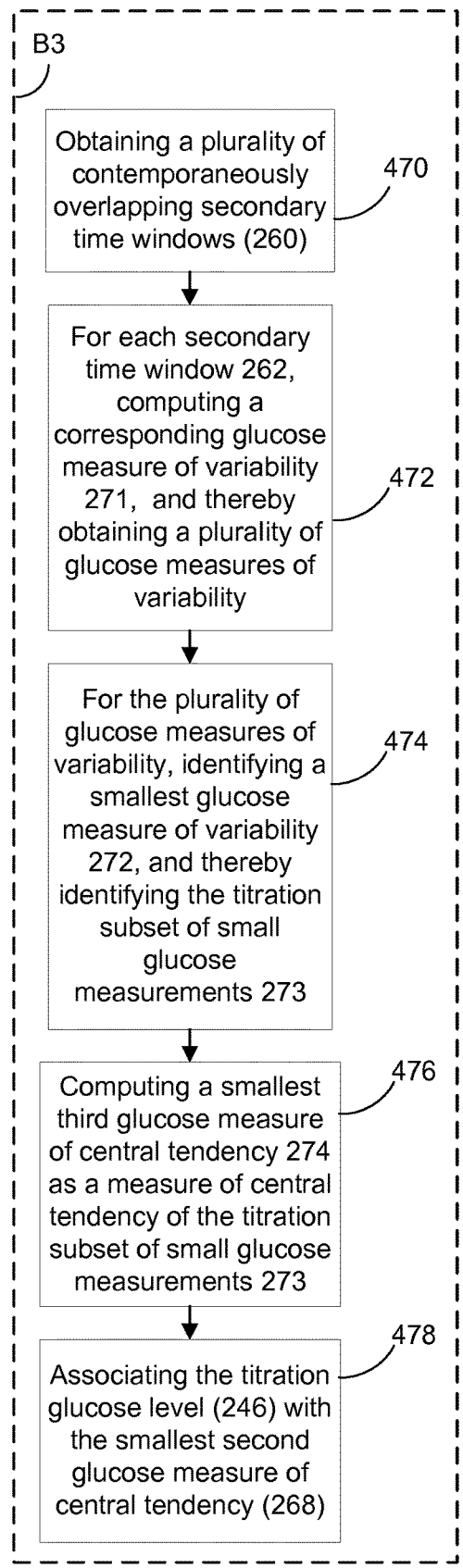

Referring to FIG. 4B, in some embodiments according to the disclosure the obtaining the titration glucose level 246, in step B, further comprises, based on the status of the insulin state indicator, selecting one of the following evaluation modes: a first evaluation mode illustrated by subprocess B1, a second evaluation mode illustrated by subprocess B2 and a third evaluation mode illustrated by subprocess B3.

Block 450. Referring to block 450 of FIG. 4C, the method can continue in a first evaluation mode with the subprocess B1, wherein the method further comprises, for the primary time window (i) obtaining an integer 234 defining the number of glucose measurements to be selected for the titration subset of small glucose measurements 240.

Block 452. Referring to block 452 of FIG. 4C, the method continues with (ii) identifying and selecting the titration subset of small glucose measurements 240 as a subset of smallest glucose measurements, by identifying and selecting the smallest glucose measurements within the primary time window 233, and ensuring that the number of measurements within the titration subset of small glucose measurements 240 equals the obtained integer 234.

Block 454. Referring to block 454 of FIG. 4C, the method continues with (iii) obtaining a first glucose measure of central tendency 244, and computed as a measure of central tendency of the glucose measurements within the titration subset of small glucose measurements 240.

Block 456. Referring to block 456 of FIG. 4C, the method continues with associating the titration glucose level 246 with the first glucose measure of central tendency 244, whereby the titration glucose level 246 can be fed into the method step C as illustrated on FIG. 4B.

Figure 6A:
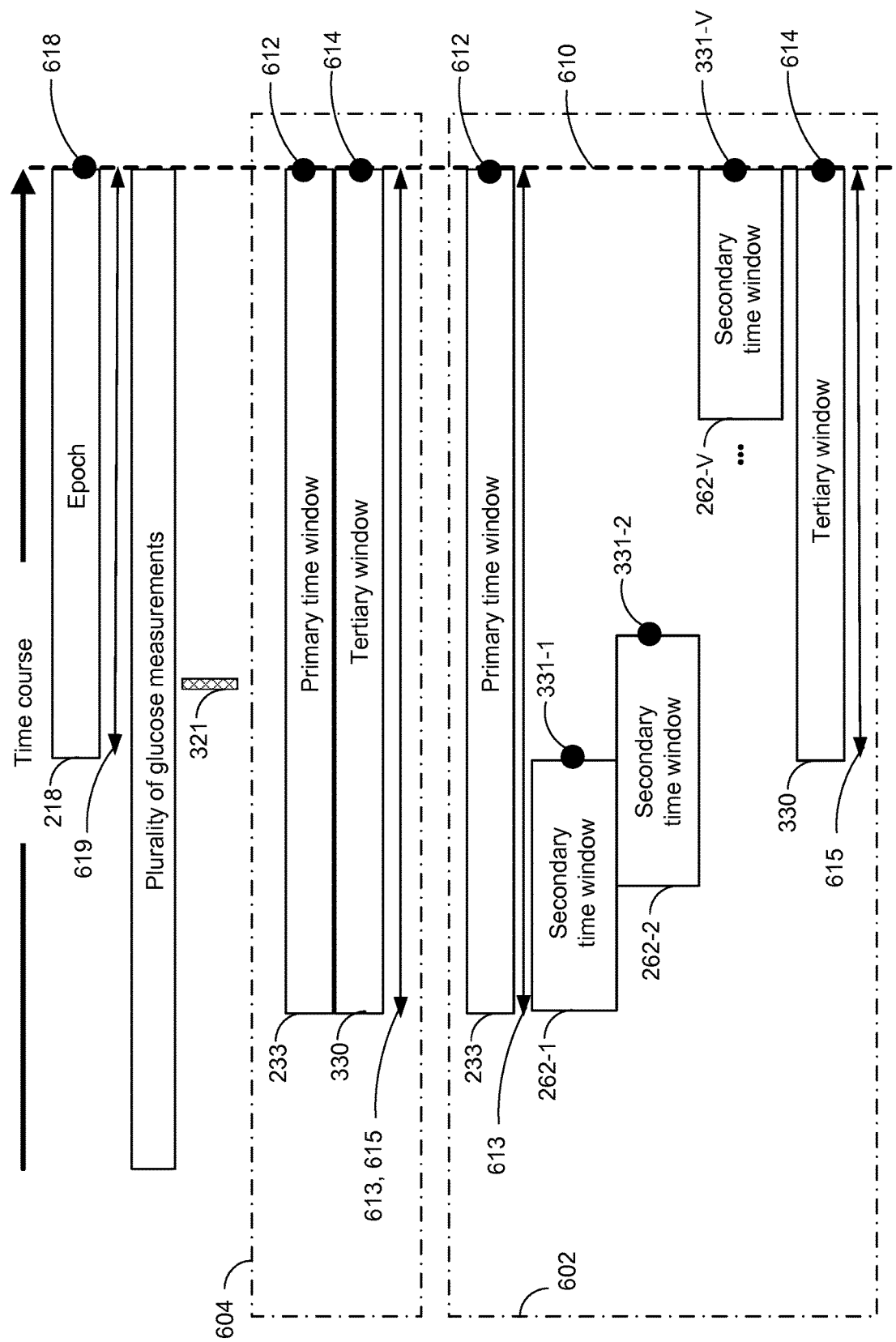
FIG. 6A illustrates the temporal relationship between a primary time window, secondary time windows, a tertiary time window, an epoch and time course wherein the plurality of glucose measurements have been obtained in accordance with embodiments of the present disclosure.
Figure 6B:
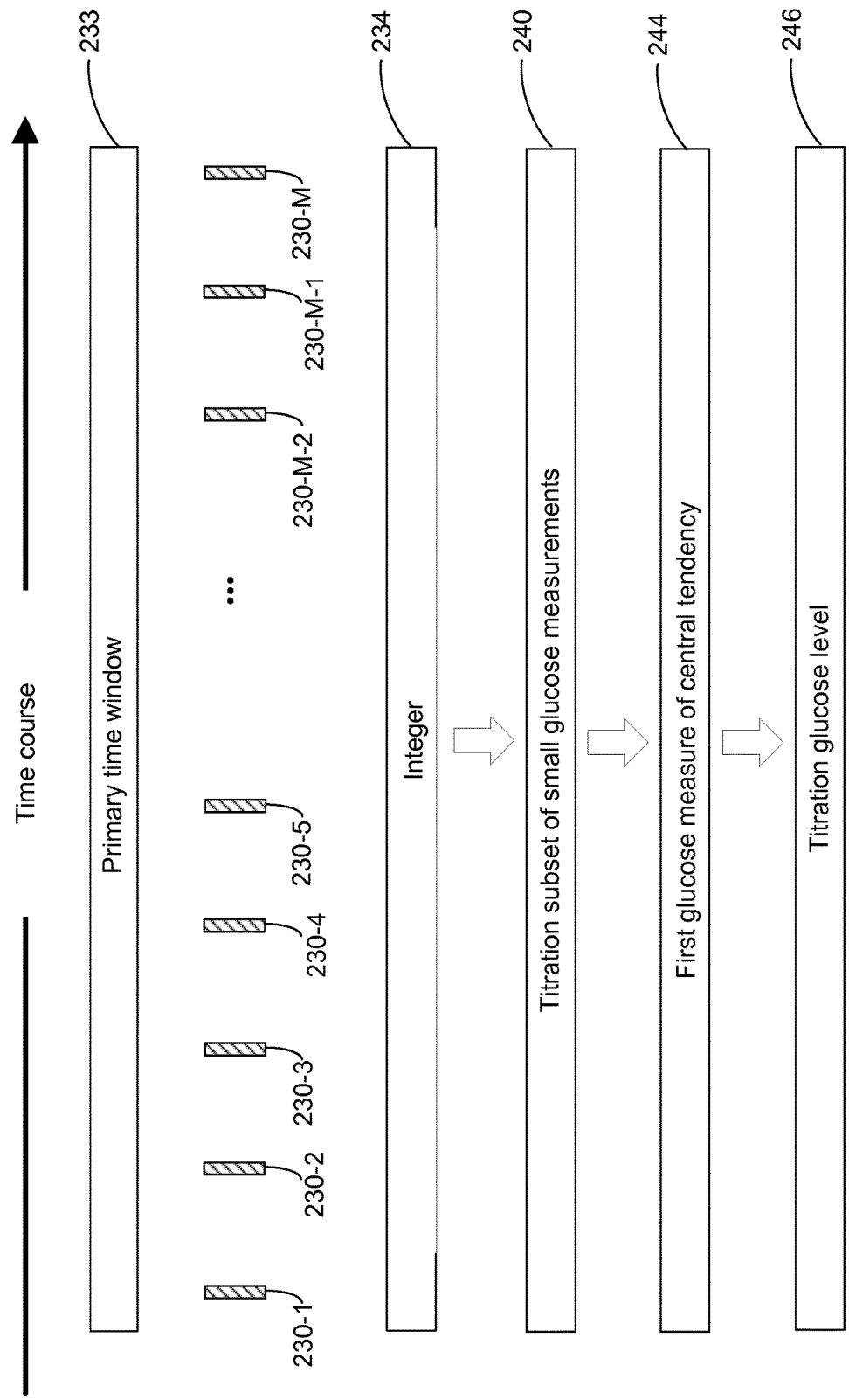
FIG. 6B illustrates the steps of identifying a titration subset of smallest glucose measurements within a primary time window, and how to obtain the corresponding glucose titration level in accordance with an embodiment of the present disclosure. The illustrated method is particularly suitable, when glucose levels are not influenced by short acting insulin.

The process of obtaining the titration glucose level according to the first evaluation mode is also schematically illustrated in FIG. 6B. An integer 234 is obtained, the titration subset of small glucose measurements 240 is obtained, the first glucose measure of central tendency can be evaluated, and the titration glucose level 246 is obtained.

Block 460. Referring to block 460 of FIG. 4C, the method can continue in a second evaluation mode with the subprocess B2, wherein the method further comprises, for the primary time window 233, obtaining a plurality of contemporaneously overlapping secondary time windows 260 within the primary time window 233, wherein each secondary time window 262 comprises a subset of overlapping glucose measurements 264 being a subset of the glucose measurements 236 in the primary time window 233

Block 462. Referring to block 462 of FIG. 4C, the method continues with, for each secondary time window 262 within the plurality of secondary time windows 260, computing a corresponding second glucose measure of central tendency 267, and thereby obtaining a plurality of second glucose measures of central tendency, wherein each respective second glucose measure of central tendency 267 is computed as a measure of central tendency of the glucose measurements within the corresponding secondary time window 262. Hereby is obtaining a moving period of a measure of central tendency across the glucose measurements in the primary time window.

Block 464. Referring to block 464 of FIG. 4C, the method continues with, for the plurality of second glucose measures of central tendency, identifying a smallest second glucose measure of central tendency 268 as the smallest second glucose measure of central tendency within the plurality of second glucose measures of central tendency, whereby the titration subset of small glucose measurements 269 is identified as the subset comprising the glucose measurements within the secondary time window 262 corresponding to the smallest second glucose measure of central tendency 268.

Block 466. Referring to block 466 of FIG. 4C, the method continues with associating the titration glucose level 246 with the smallest second glucose measure of central tendency 268, whereby the titration glucose level 246 can be fed into the method step C as illustrated on FIG. 4B.

The process of obtaining the titration glucose level according to the second evaluation mode is also schematically illustrated in FIG. 6C. A plurality of secondary time windows is obtained and a second glucose measure of central tendency 267 is associated with each of the secondary time windows, and thereby creating a plurality of second glucose measures of central tendency. Next, the smallest second glucose measure of central tendency, in the illustrated example the second glucose measure of central tendency 267-2, is identified as a smallest second glucose measure of central tendency 268 among the plurality of second glucose measures of central tendency, and the corresponding secondary time window 262-2 is identified as the titration subset of small glucose measurements 269, the smallest second glucose measure of central tendency 268 can be associated with the titration glucose level 246, whereby the titration glucose level is obtained, and can be used for adjusting the dose of the long acting insulin medicament.

Block 470. Referring to block 470 of FIG. 4D, the method can continue in a third evaluation mode with the subprocess B3, wherein the method further comprises, for the primary time window 233, obtaining a plurality of contemporaneously overlapping secondary time windows 260 within the primary time window 233, wherein each secondary time window 262 comprises a subset of overlapping glucose measurements 264 being a subset of the glucose measurements 236 in the primary time window 233.

Block 472. Referring to block 472 of FIG. 4D, the method continues with for each secondary time window 262 within the plurality of secondary time windows 260, computing a corresponding glucose measure of variability 271, and thereby obtaining a plurality of glucose measures of variability, wherein each respective glucose measure of variability 271 is computed as a measure of variability of the glucose measurements within the corresponding secondary time window 262, and thereby obtaining a moving period of a measure of variability across the glucose measurements in the primary time window.

Block 474. Referring to block 474 of FIG. 4D, the method continues with, for the plurality of glucose measures of variability, identifying a smallest glucose measure of variability 272, as the smallest glucose measure of variability within the plurality of glucose measures of variability, whereby the titration subset of small glucose measurements 273 is identified as the subset comprising the glucose measurements within the secondary time window 262 corresponding to the smallest glucose measure of variability 272.

Block 476. Referring to block 476 of FIG. 4D, the method continues with computing a smallest third glucose measure of central tendency 274 as a measure of central tendency of the titration subset of small glucose measurements 273.

Block 478. Referring to block 478 of FIG. 4D, the method continues with associating the titration glucose level 246 with the smallest third glucose measure of central tendency 274.

Figure 6D:
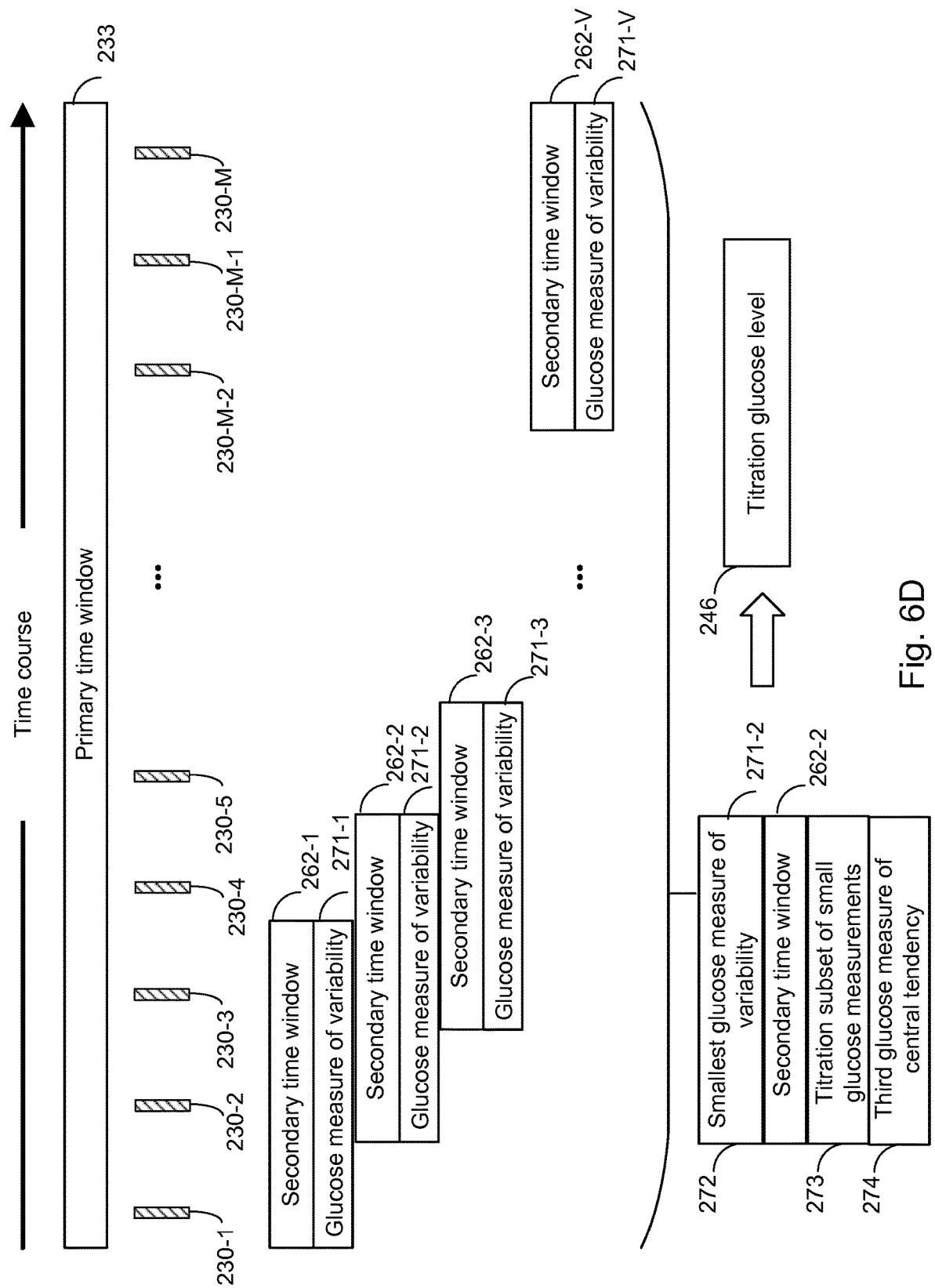
FIG. 6D illustrates the steps of identifying a titration subset of small glucose measurements within a primary time window, and the step of obtaining the corresponding glucose titration level in accordance with another embodiment of the present disclosure. The illustrated method is particularly suitable, when glucose levels can be influenced by short acting insulin.

The process of obtaining the titration glucose level according to the third evaluation mode is also schematically illustrated in FIG. 6D. A plurality of secondary time windows is obtained and a glucose measure of variability 271 is associated with each of the secondary time windows, and thereby creating a plurality of glucose measures of variability. Next, the smallest glucose measure of variability, in the illustrated example it is the secondary time window 262-2, is identified as a smallest glucose measure of variability 272 among the plurality of glucose measures of variability, and the corresponding secondary time window 262-2 is identified as the titration subset of small glucose measurements 273, a third glucose measure of central tendency 274 is evaluated based on the titration subset of small glucose measurements 273 and associated with the titration glucose level 246, whereby the titration glucose level is obtained, and can be used for adjusting the dose of the long acting insulin medicament.

Block 430. Referring to block 430 of FIG. 4C, in some embodiments according to the present disclosure the method further comprises, in response to identifying the state of the insulin state indicator 211, selecting the first or the second evaluation mode, upon the occurrence that the state of the insulin state indicator is identified as the only-long-acting-insulin-influence state, and thereby using a preferred method for obtaining the titration glucose level 246, which is preferred for titration with a long acting insulin medicament, when it is ensured that no short acting insulin medicament influences the glucose measurements 236.

Block 430. Referring to block 430 of FIG. 4C, in some embodiments according to the present disclosure the method further comprises, in response to identifying the state of the insulin state indicator 310, selecting the third evaluation mode, upon the occurrence that the state of the insulin state indicator is identified as the a short-acting-insulin-influence state, and thereby using a preferred method for obtaining the titration glucose level 246, which is preferred for titration with a long acting insulin medicament, when it is identified that short acting insulin medicament influences the glucose measurements 236.

Block 432. Referring to block 432 of FIG. 4C, in some embodiments according to the present disclosure the first data structure further comprises a hypoglycemic risk state indicator, wherein the hypoglycemic risk state indicator can indicate a high hypoglycemic risk state, wherein the subject may have a high hypoglycemic risk or wherein a high variability across the plurality of glucose measurements can be observed, and a non-high hypoglycemic risk state, wherein the subject may have a non-high hypoglycemic risk or wherein a low variability across the plurality of glucose measurements can be observed, and wherein the method further comprises: in response to identifying the state of the hypoglycemic risk state indicator, selecting the first evaluation mode, upon the occurrence that the state of the hypoglycemic risk state indicator is identified as the high hypoglycemic risk state, and thereby using a method for obtaining the titration glucose level 246 which may be beneficial in situation with low glucose values and noise.

Block 432. Referring to block 432 of FIG. 4C, in some embodiments according to the present disclosure the first data structure further comprises a hypoglycemic risk state indicator, wherein the hypoglycemic risk state indicator can indicate a high hypoglycemic risk state, wherein the subject may have a high hypoglycemic risk or wherein a high variability across the plurality of glucose measurements can be observed, and a non-high hypoglycemic risk state, wherein the subject may have a non-high hypoglycemic risk or wherein a low variability across the plurality of glucose measurements can be observed, and wherein the method further comprises: in response to identifying the state of the hypoglycemic risk state indicator, selecting the second evaluation mode, upon the occurrence that the state of the hypoglycemic risk state indicator is identified as the non-high hypoglycemic risk state, and thereby using a method for obtaining the titration glucose level 246 which may be beneficial under these circumstances.

In some embodiments of the present disclosure, the measure of variability 271 is the variance. For instance, in some embodiments a moving measure of variability is a moving period of variance $\sigma_k^2$ across the glucose measurements, where:

$$\sigma_k^2 = \left( \frac{1}{M} \sum_{i=k-M+1}^{k} (G_i - \overline{G}) \right)^2$$

and where, $G_i$ is the $i^{th}$ glucose measurement in the portion k of the plurality of glucose measurements considered, M is a number of glucose measurements in the plurality of glucose measurements and represents a contiguous predetermined time span, i.e., the secondary time window, $\overline{G}$ is the mean of the M glucose measurements selected from the plurality of glucose measurements of the first data set 228, and k is within the first time window.

In some embodiments of the present disclosure the measure of central tendency 244, 268, 274 is the mean value. For instance, in some embodiments a moving measure of central tendency is a moving mean or moving average $\mu_k$ across the glucose measurements, where:

$$\mu_k = \frac{1}{M} \sum_{i=k-M+1}^{k} G_i$$

and where, $G_i$ is the $i^{th}$ glucose measurement in the portion k of the plurality of glucose measurements considered, M is a number of glucose measurements in the plurality of glucose measurements and represents a contiguous predetermined time span, i.e., the secondary time window, and k is within the first time period.

In some embodiments of the present disclosure the method is repeated on a recurring basis. For example, whether and how much to adjust the dose of a long-acting insulin medicament can be requested on a daily basis, which means that the titration glucose level is evaluated on a daily basis.

In some embodiments of the present disclosure, the method further comprises obtaining a second data set 320 from one or more insulin pens 104 used by the subject to apply the prescribed insulin regimen, as illustrated in FIGS. 3A through 3D, the second data set comprises a plurality of insulin medicament records over the time course, each insulin medicament record 321 in the plurality of medicament records comprises: (i) a respective insulin medicament injection event 322 representing an insulin medicament injection into the subject using a respective insulin pen in the one or more insulin pens 104 and (ii) a corresponding electronic timestamp 323 that is automatically generated by the respective insulin pen upon occurrence of the respective insulin medicament injection event. For the first glucose measures of central tendency 244 in the first evaluation mode, the first glucose measure of central tendency is associated with a tertiary time window 330 representing an evaluation period, wherein a most recent end point 614 of the tertiary time window is synchronized with a most recent end point 612 of the primary time window 233, and wherein the primary and the tertiary windows are of the same length, as illustrated on FIG. 6A in the marked area 604. Alternatively, for the plurality of second glucose measures of central tendency in the second evaluation mode, each respective second glucose measure of central tendency 267 is associated with a time indicator 331 representing the time of evaluation of the respective second glucose measure of central tendency, and thereby obtaining a plurality of time indicators defining a tertiary time window 330 representing an evaluation period, wherein a most recent end point 614 of the tertiary time window is synchronized with a most recent end point 612 of the primary time window, and wherein the length 615 of the tertiary time window 330 is smaller than the length 613 of the primary time window 233, as illustrated on FIG. 6A in the marked area 602. Alternatively, for the plurality of glucose measures of variability in the third evaluation mode, each respective glucose measure of variability 267 is associated with a time indicator 331 representing the time of evaluation of the respective glucose measure of variability, and thereby obtaining a plurality of time indicators defining a tertiary time window 330 representing an evaluation period, wherein a most recent end point 614 of the tertiary time window is synchronized with a most recent end point (612) of the primary time window, and wherein the length 615 of the tertiary time window 330 is smaller than the length 613 of the primary time window 233. This also illustrated on FIG. 6A in the marked area 604. The method continues by associating the titration glucose level 246 with the tertiary time window 330, as illustrated on FIGS. 6E and 6F, and applying a first characterization 335 to the tertiary time window 330 (not illustrated), wherein the first characterization 335 is one of basal regimen adherent and basal regimen nonadherent, the tertiary time window 330 is deemed basal regimen adherent when the second data set 320 includes one or more medicament records that establish, on a temporal and quantitative basis, adherence with the prescribed basal insulin medicament dosage regimen 212 during the respective tertiary time window 330, and the tertiary time window is deemed basal regimen nonadherent when the second data set 320 fails to include one or more medicament records that establish, on a temporal and quantitative basis, adherence with the prescribed basal insulin medicament dosage regimen 212 during the tertiary time window 330. Hereafter the method may continue with adjusting the long acting insulin medicament dosage 216 in the basal insulin medicament dosage regimen 214 for the subject based upon a titration glucose level 244 represented by a tertiary time window 330 that is deemed basal regimen adherent and by excluding a titration glucose level 244 represented by a tertiary time window 330 that is deemed basal regimen nonadherent.

Figure 2A:
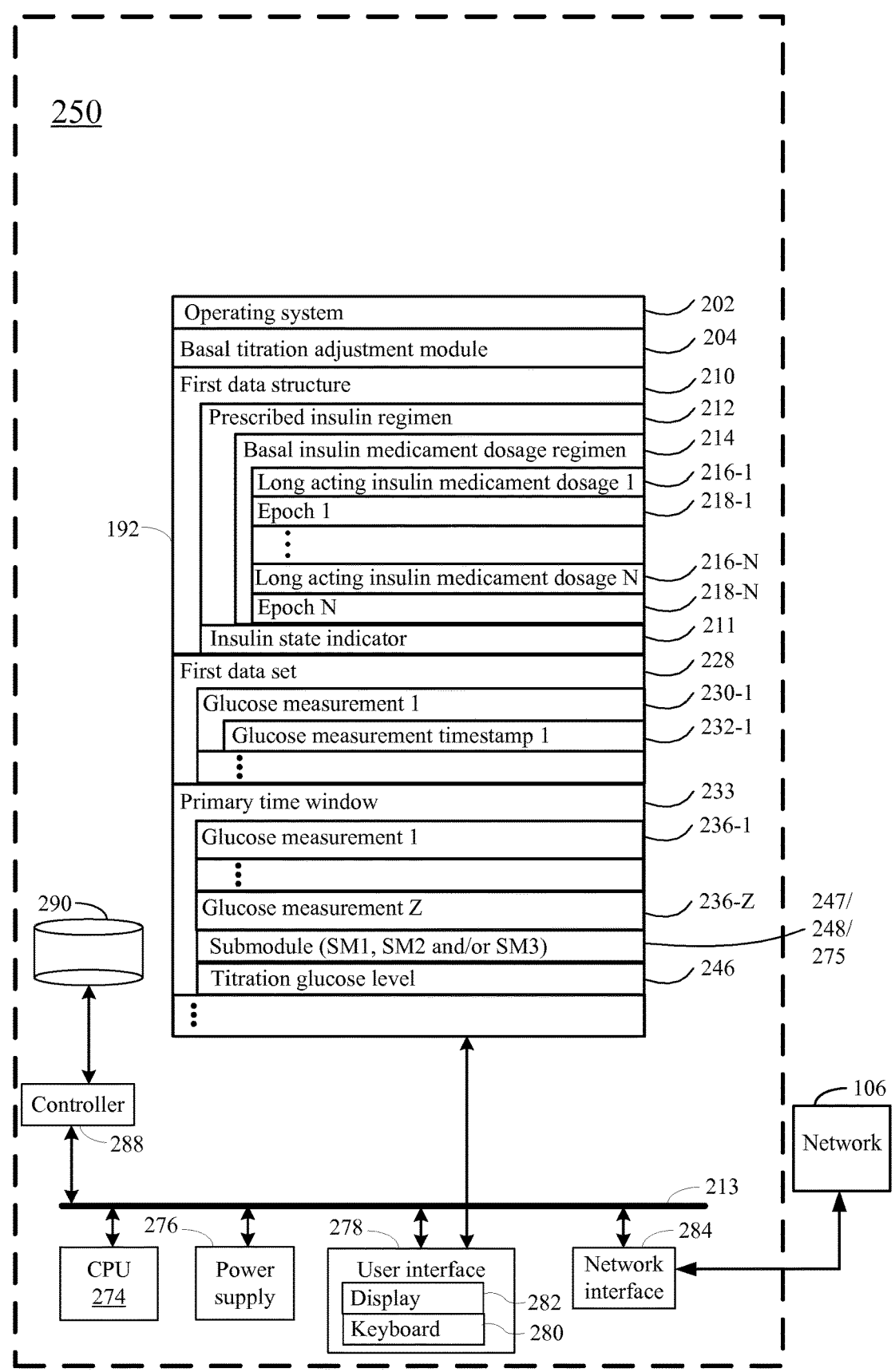
FIGS. 2A, 2B, 2C and 2D collectively illustrate a basal titration adjustment device for autonomously adjusting a long acting insulin medicament dosage in a prescribed insulin regimen in accordance with an embodiment of the present disclosure.
Figure 2B:
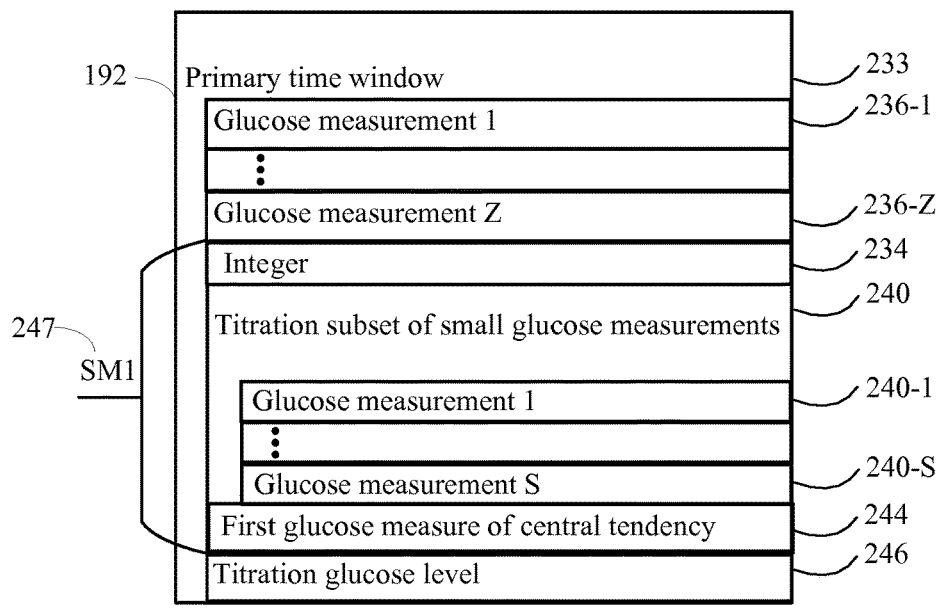
Figure 2C:
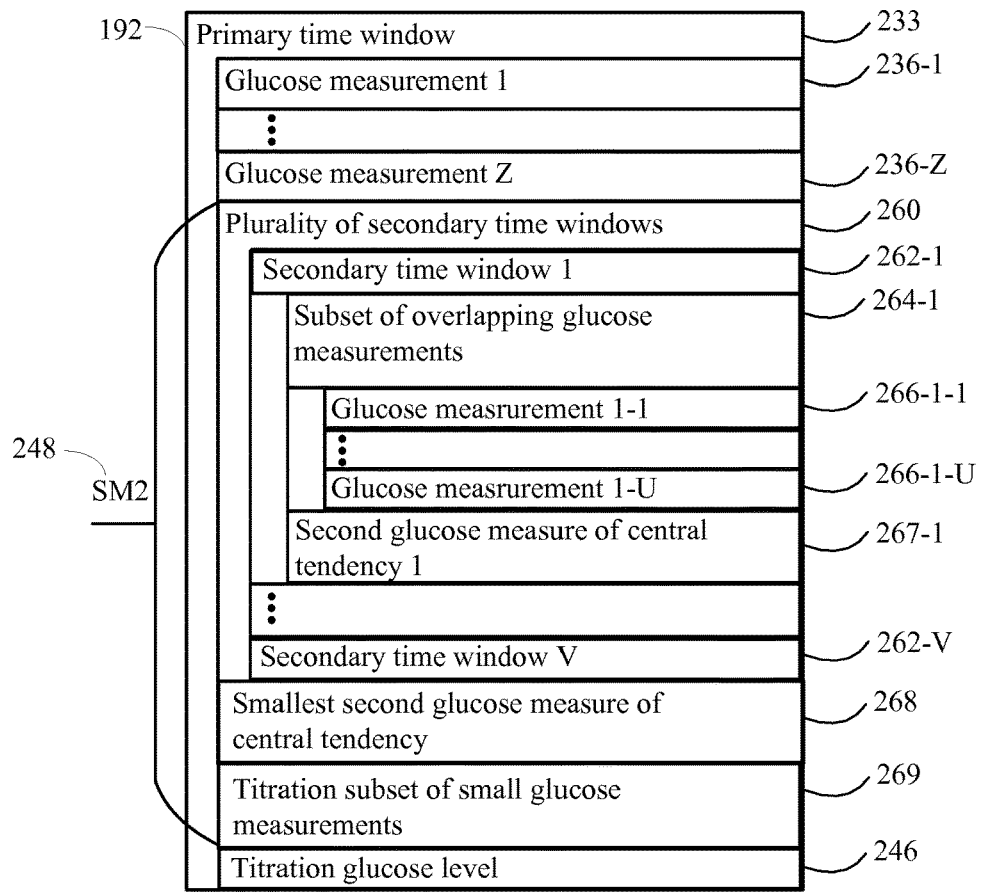
Figure 2D:
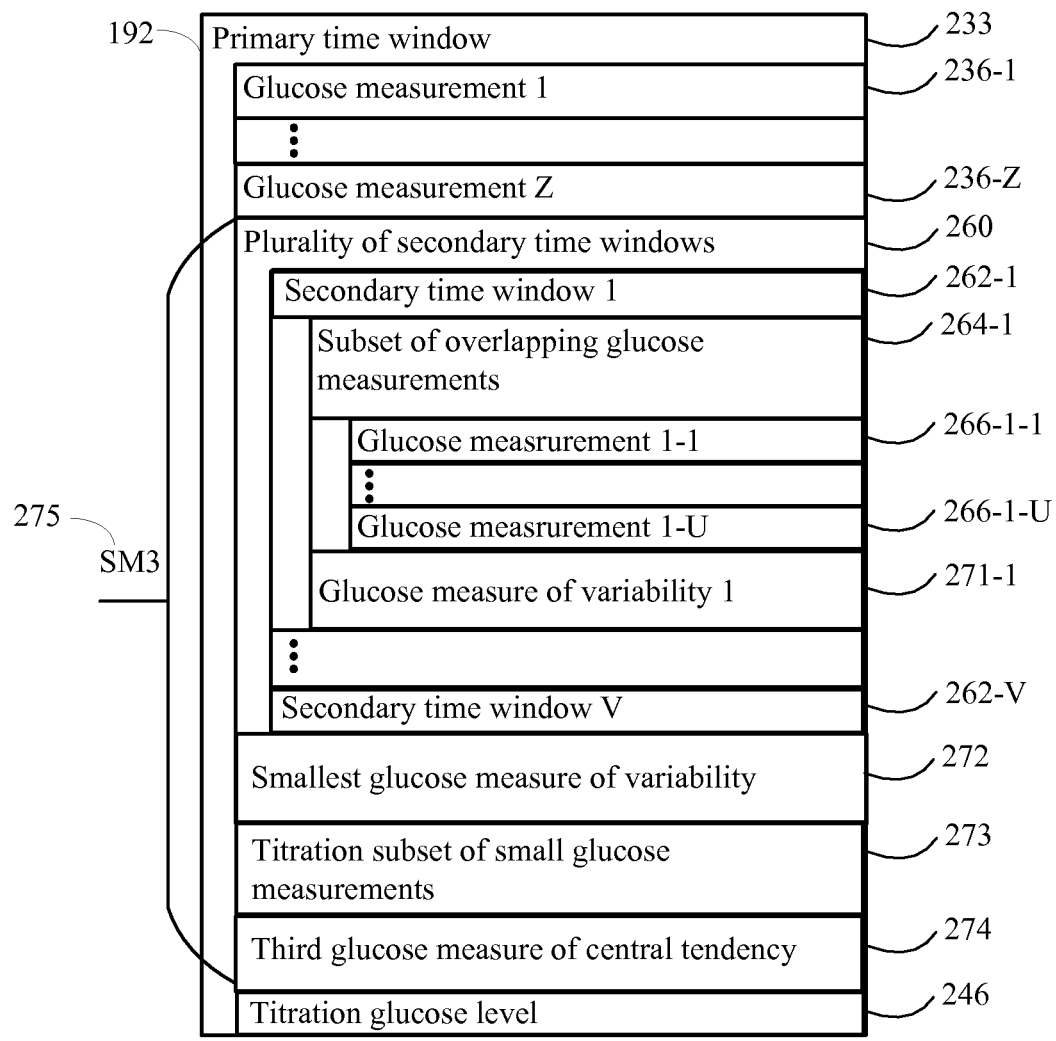
Figure 3A:
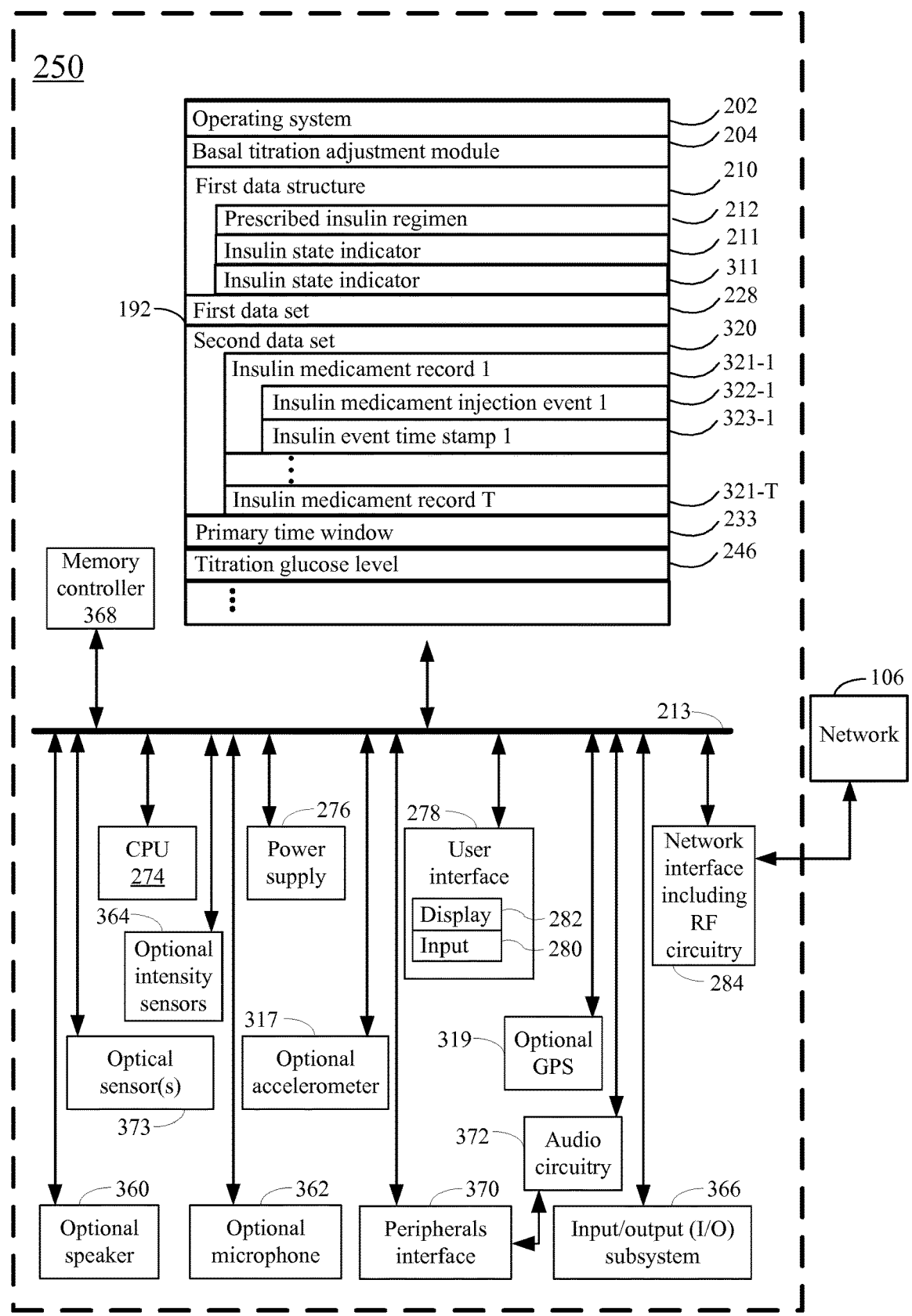
FIGS. 3A, 3B, 3C and 3D collectively illustrate a basal titration adjustment device for autonomously adjusting a long acting insulin medicament dosage in a prescribed insulin regimen in accordance with another embodiment of the present disclosure.
Figure 3B:
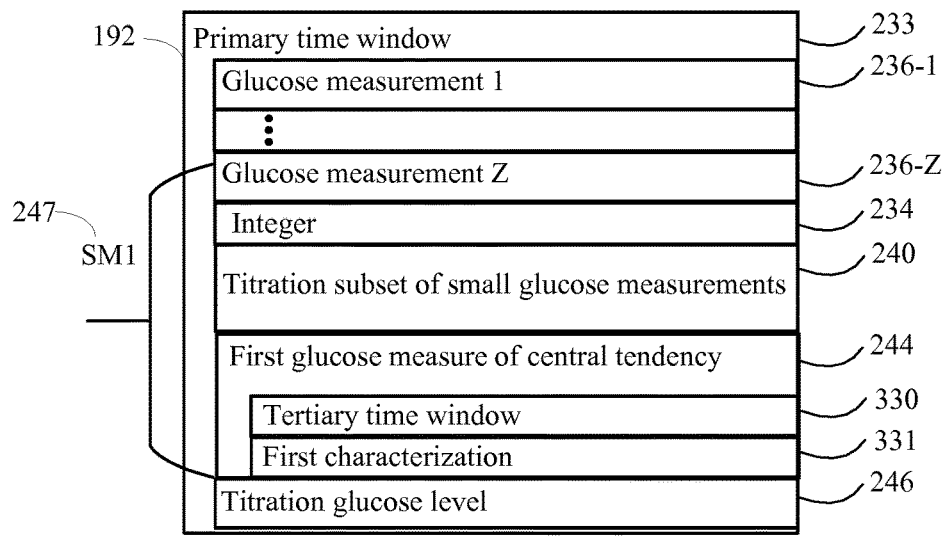
Figure 3C:
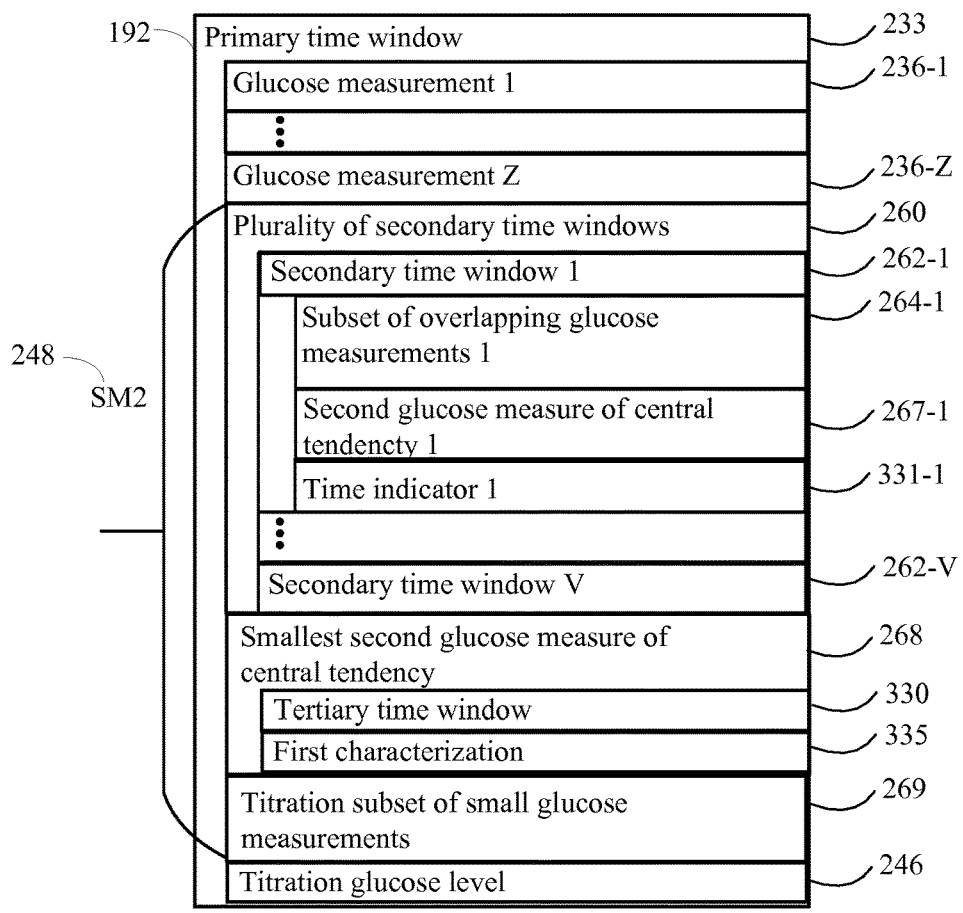
Figure 3D:
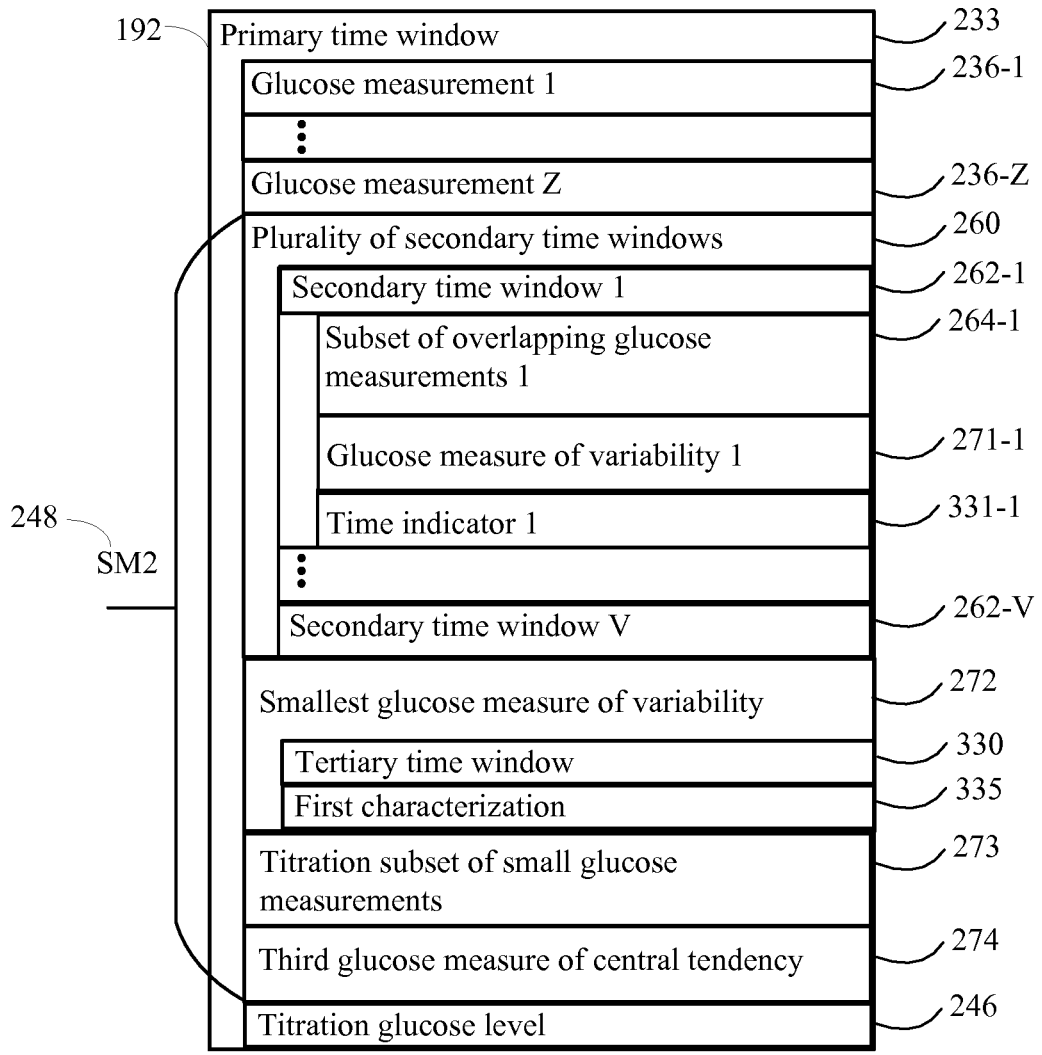

As illustrated on FIG. 2A and FIG. 6A, in some embodiments the first data structure 210 comprises a plurality of consecutive epochs, wherein each respective epoch 218 is associated with a basal insulin medicament dosage 216, indicating when the basal insulin medicament is to be injected within the respective epoch 218, and how much of the basal insulin medicament is to be injected. Thereby the first data structure 210 provides a temporal and quantitative basis for the first characterization. In some embodiments the length 615 of the tertiary window 330 is longer than or the same as the length 619 of each of the epochs 218. In some embodiments the end point 614 of the tertiary time window is synchronized with an end point 618 of a current epoch, wherein the current epoch is the most recent completed epoch within the plurality of epochs.

Figure 6E:
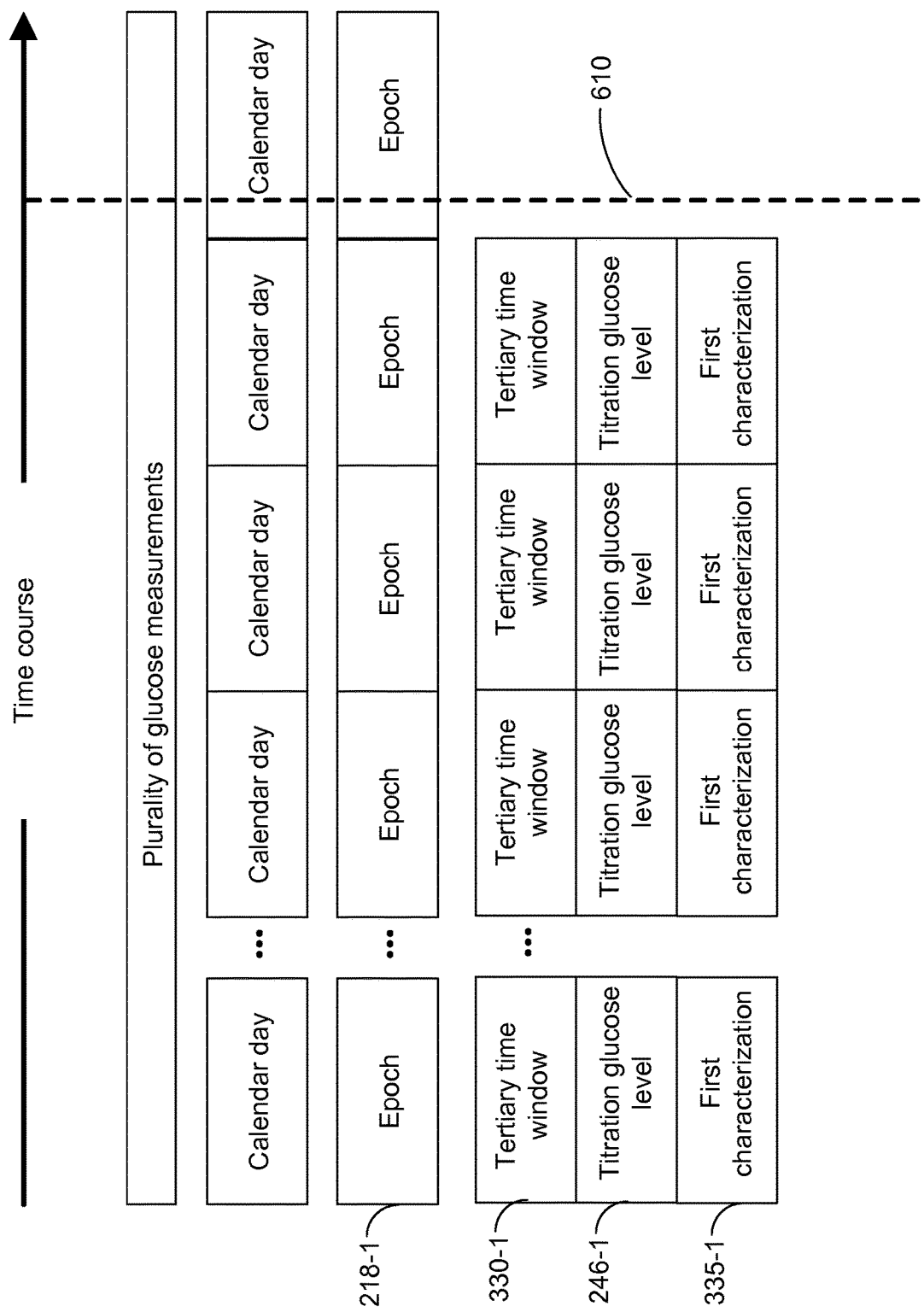
FIGS. 6E and 6F collectively illustrate that the relation between tertiary windows and a present time 610, where a user requests an evaluation of the titration glucose level. The figures also illustrate the temporal alignment of tertiary windows, epochs and calendar units, e.g., a calendar day.
Figure 6F:
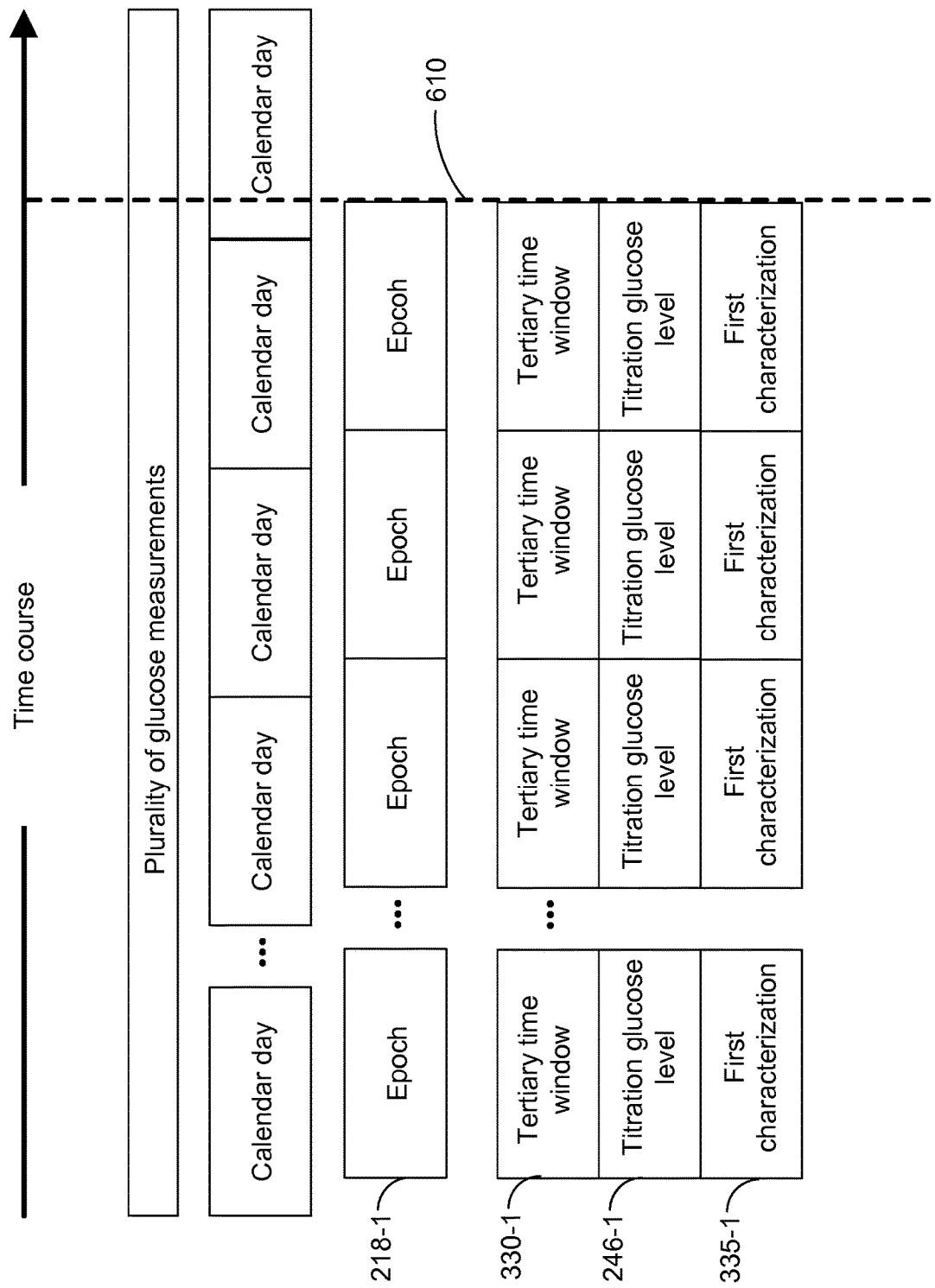

As illustrated on FIGS. 6E and 6F, in some embodiments each respective epoch 218 of the plurality of epochs is associated with a tertiary time window 330, and thereby obtaining a plurality of tertiary time windows, wherein each tertiary time window represents an evaluation period, wherein each tertiary window is aligned with the respective epoch on a temporal bases, and wherein each tertiary time window 330 is associated with a titration glucose level 246.

In some embodiments the first data structure comprises a specification of temporal and quantitative basis for administration of the long acting insulin medicament, for each of the epochs 218 within the plurality of epochs. In some embodiments the quantitative basis for the long acting insulin medicament is a function of the titration glucose level. In some embodiments the temporal basis is specified as one injection for each epoch 218 within the plurality of epochs. In some embodiments each epoch 218 in the plurality of epochs is a calendar day or a calendar week, as illustrated in FIGS. 6E and 6F.

In some embodiments successive measurements in the plurality of glucose measurements are autonomously taken from the subject at an interval rate of 5 minutes or less, 3 minutes or less, or 1 minute or less. In some embodiments the device further comprises a wireless receiver 284, and wherein the first data set is obtained wirelessly from a glucose sensor 102 affixed to the subject and/or the second data set is obtained wirelessly from the one or more insulin pens 104.

In some embodiments, the first data structure further comprises a hypoglycemic risk state indicator 311, wherein the hypoglycemic risk state indicator 311 can indicate a high hypoglycemic risk state, wherein the subject may have a high hypoglycemic risk or wherein a high variability across the plurality of glucose measurements can be observed, and a non-high hypoglycemic risk state, wherein the subject may have a non-high hypoglycemic risk or wherein a low variability across the plurality of glucose measurements can be observed, and wherein the method further comprises. Referring to Block 432 FIG. 4B, in response to identifying the state of the hypoglycemic risk state indicator, the method further comprises selecting the first evaluation mode, upon the occurrence that the state of the hypoglycemic risk state indicator is identified as the high hypoglycemic risk state, and thereby using a method for obtaining the titration glucose level 246 which is more beneficial in case of low glucose values and noise.

In some embodiments, the secondary time window is 50 minutes to 70 minutes, 60 minutes to 120 minutes, 120 minutes to 180 minutes or 180 minutes to 300 minutes. In some embodiments, successive measurements in the plurality of glucose measurements are autonomously taken from the subject at an interval rate of 4 minutes to 6 minutes, and wherein the secondary time window is 50 minutes to 70 minutes. In some embodiments successive measurements in the plurality of glucose measurements are autonomously taken from the subject at an interval rate of 40 minutes to 80 minutes, and wherein the secondary time window is 180 minutes to 310 minutes.

A flow diagram of the subprocesses B1, B2 and B2 applying a first, second and third evaluation mode, respectively, has been illustrated on FIG. 4B through 4D, and FIG. 7A through FIG. 7F further illustrates by example how the titration subset of small glucose measurements is obtained in order to obtain the titration glucose level.

Figure 7A:
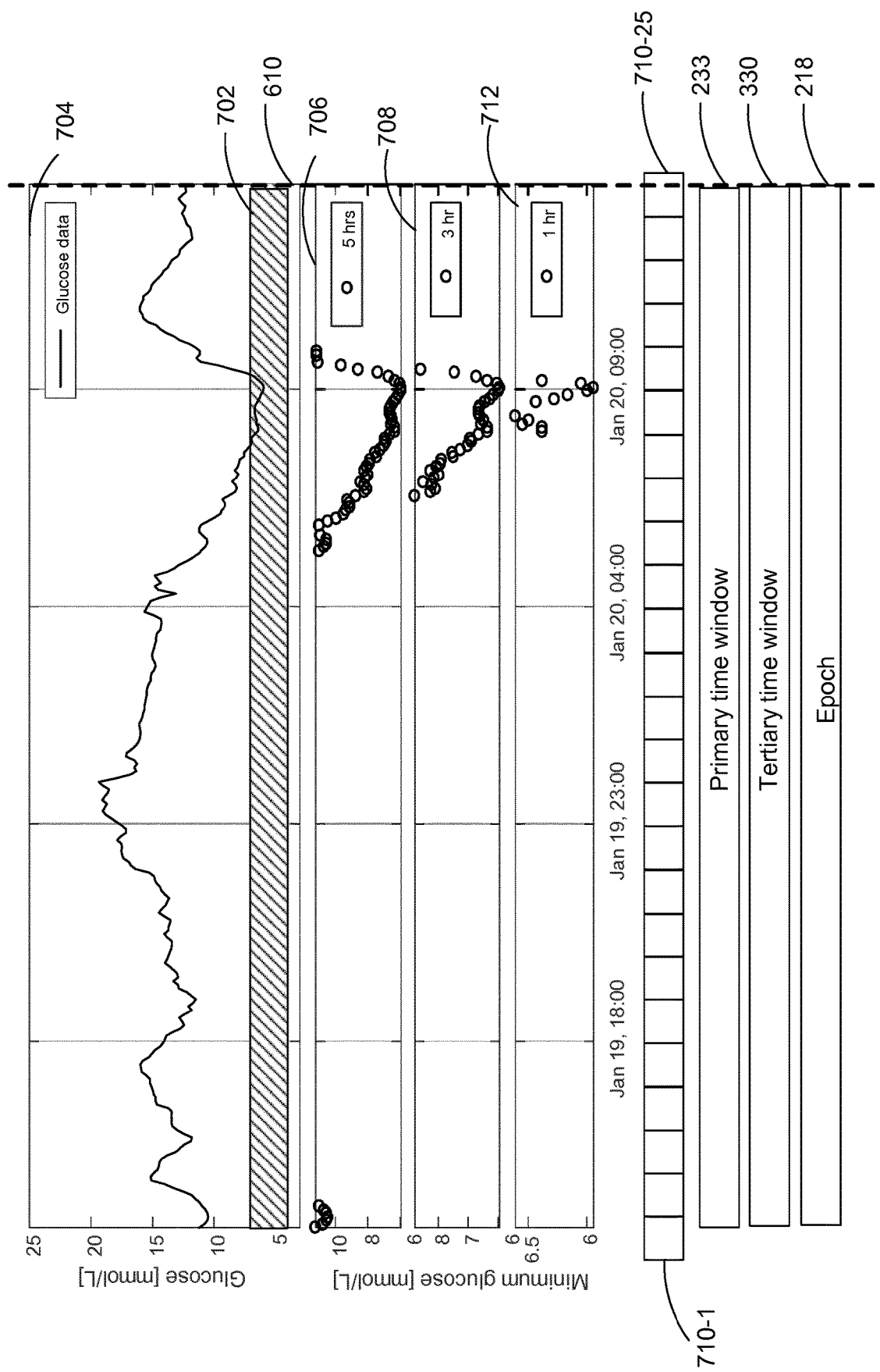
FIGS. 7A, 7B, 7C, 7D, 7E and 7F collectively illustrate examples of identifying a titration subset of small glucose measurements according embodiment of the present disclosure.
Figure 7B:
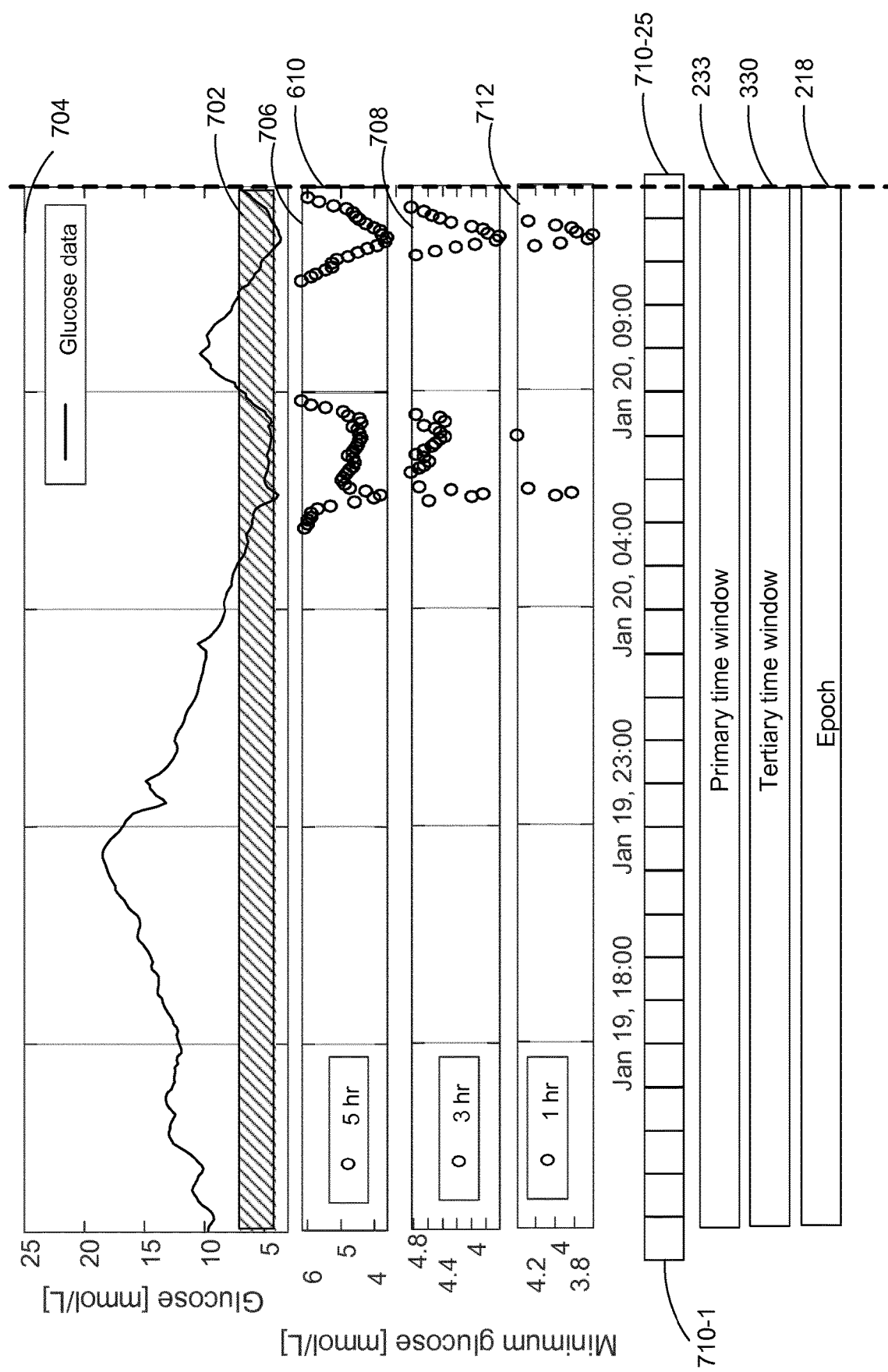
Figure 7C:
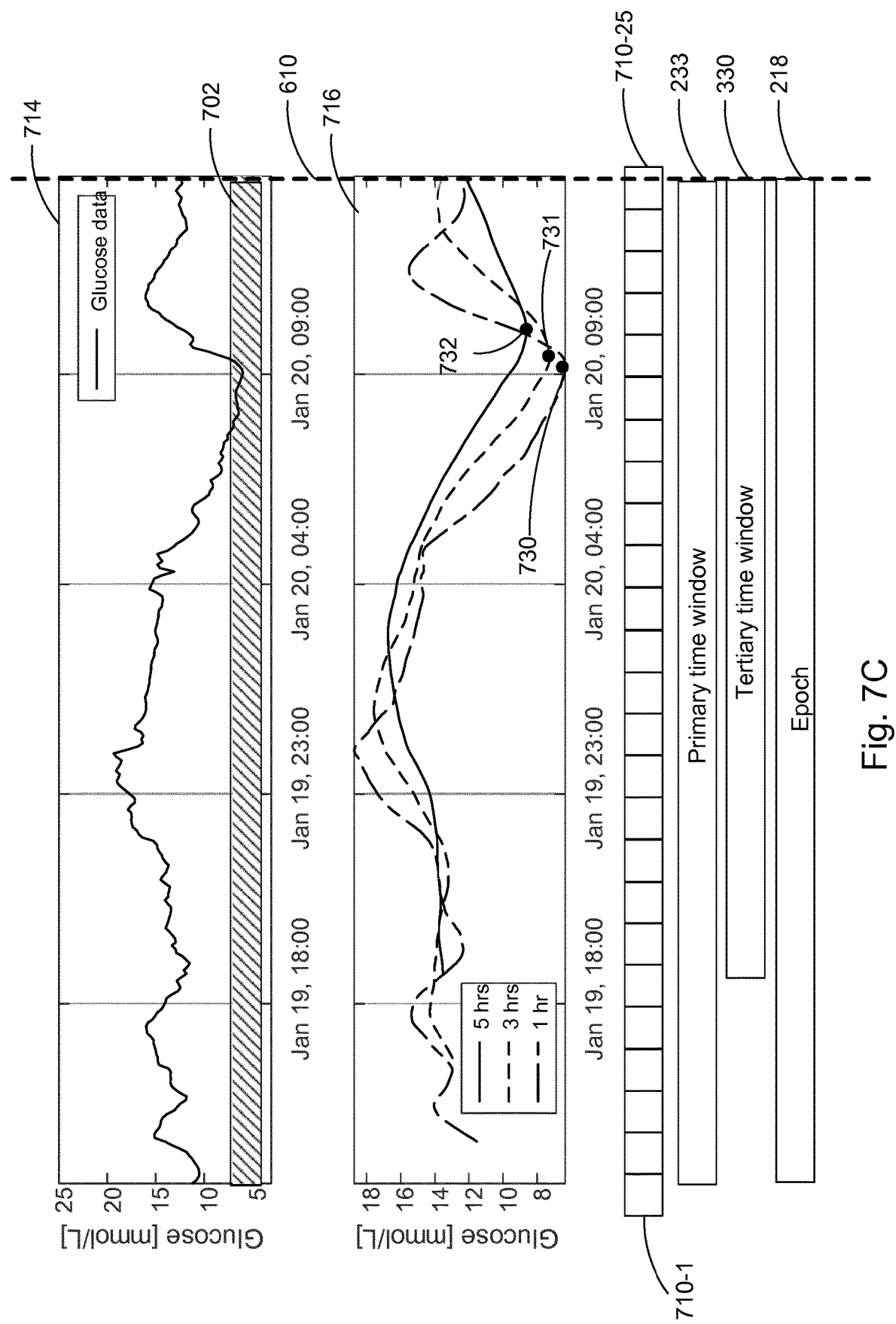
Figure 7D:
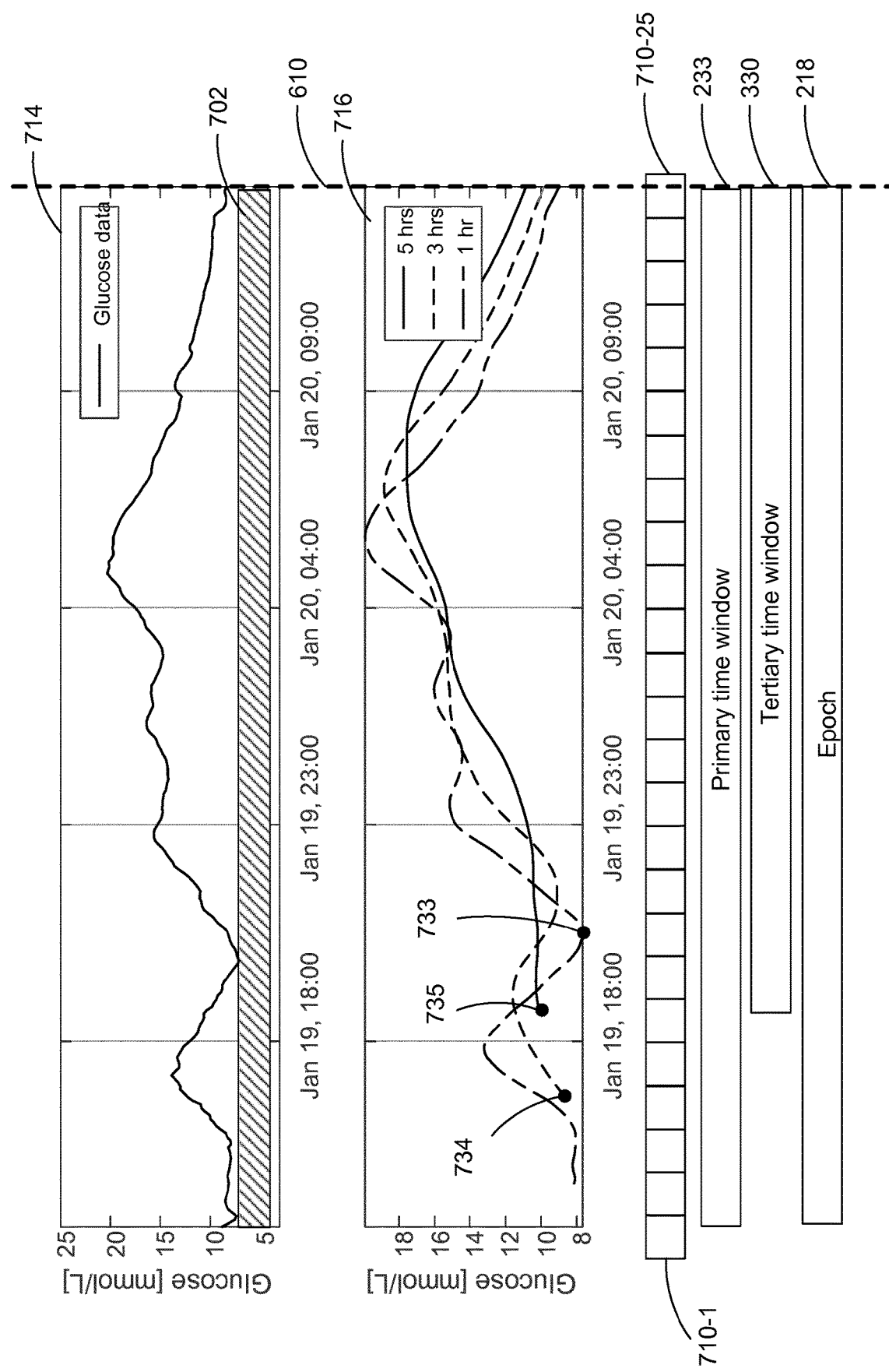
Figure 7E:
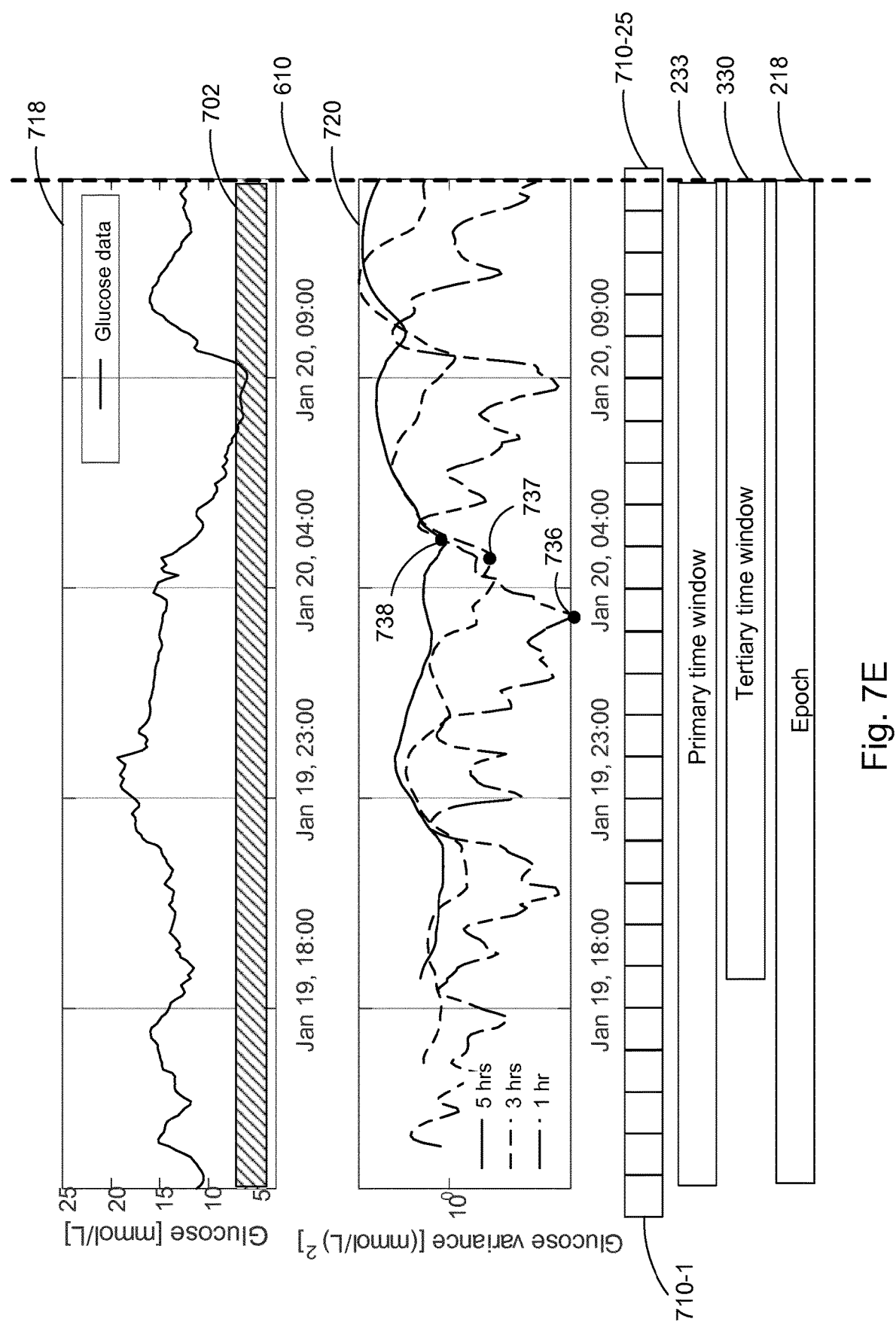

FIGS. 7A, 7C and 7E illustrate a first case, where a patient is only on basal insulin and therefore the low glucose values can only be caused by basal insulin injections or endogenous insulin or other natural causes. In the second case, illustrated in FIGS. 7B, 7D and 7F, the patient is on multiple daily injections (MDI) treatment which involves injections with fast acting insulin, and small glucose values are therefore not necessarily related to the basal insulin injections or endogenous insulin production, but could also be caused by the fast acting insulin used to account for the carbohydrates ingested during a meal or to correct for a high glucose level after a meal (correction bolus). The examples of FIG. 7A through 7F illustrate glucose data obtained during a time course of 24 hours, and calendar hours is illustrated by rectangles 710. The primary time window 710, the tertiary time window 330, the epoch 218 and the request time 610, where a user requests the calculation of a titration glucose level, is also indicated on the figures. The patterned rectangle 702 indicates the upper and lower boundaries defining a desired range for the blood glucose level.

Referring to FIGS. 7A and 7B, the top panel 704 illustrates the glucose level as a function of time obtained from the plurality of glucose measurements within the time course. The second panel from the top 706, the third panel from the top 708 and the fourth panel from the top 712, respectively, shows the lowest glucose values corresponding to 5 hours, 3 hours, and 1 hours sampling, wherein the sampling rate has been 1 sample or measurement per 5 minutes, i.e., 12 measurements per hour. Therefore 5 hours sampling corresponds to 60 measurements, and the second panel from the top shows the 60 smallest or lowest measurements, 3 hours sampling corresponds to 36 measurements and the third panel from the top shows the 36 smallest measurements, and 1 hour corresponds to 12 measurements and the fourth panel from the top (the bottom panel) shows the 12 smallest measurements. Each of the sets containing a number of smallest glucose measurements can be used as the titration subset of small glucose measurements 269, and can be used to evaluate the titration glucose level 246. The integer 234 used to define the number of measurements in the titration subset of small glucose measurements is here obtained as a product of the sampling rate and the time window, e.g., 12 measurements per hour for 1 hour is 12 measurements. The integer could also be specified as a nearest integer of a fraction of the total number of measurements within the primary time window. For the glucose data illustrated in FIG. 7A the patient is on basal insulin only, hence low glucose values only relate to endogenous insulin and long acting insulin. Here the lowest average is found at around 9:00 on January 20. For the glucose data illustrated in FIG. 7B the patient takes a correction bolus after dinner which causes glucose to decrease at around 20:00. Here the lowest average is found at around 20:00 on January 19.

Referring to FIGS. 7C and 7D, the top panel 714 illustrates the glucose level as a function of time obtained from the plurality of glucose measurements within the time course. The second panel 716 shows the running average glucose with different window sizes of 5 hours, 3 hours and 1 hour, respectively. The lowest evaluated average can be used as the titration glucose level. The illustrated tertiary window 330 corresponds to the running average using a 5 hours window (secondary time window is 5 hours). For the glucose data illustrated in FIG. 7C the patient is on basal insulin only, hence low glucose values only relate to endogenous insulin and long acting insulin. Here the smallest average for the 1 hour window 730 is found at around 9:00 on January 20. The smallest average for the 3 hour window 731 is found at around 9:30. The smallest average for the 5 hour window 732 is found around 10:00. For the glucose data illustrated in FIG. 7D the patient takes a correction bolus after dinner which causes glucose to decrease at around 20:30. Here the smallest average for the 1 hour window 733 is found at around 20:30 on January 19. The smallest average for the 3 hour window 734 is found at around 17:00 (beginning of tertiary period for 3 hour window). The smallest average for the 5 hour window 735 is found at around 19:00 (beginning of tertiary period 330 for the 5 hour window).

Figure 7F:
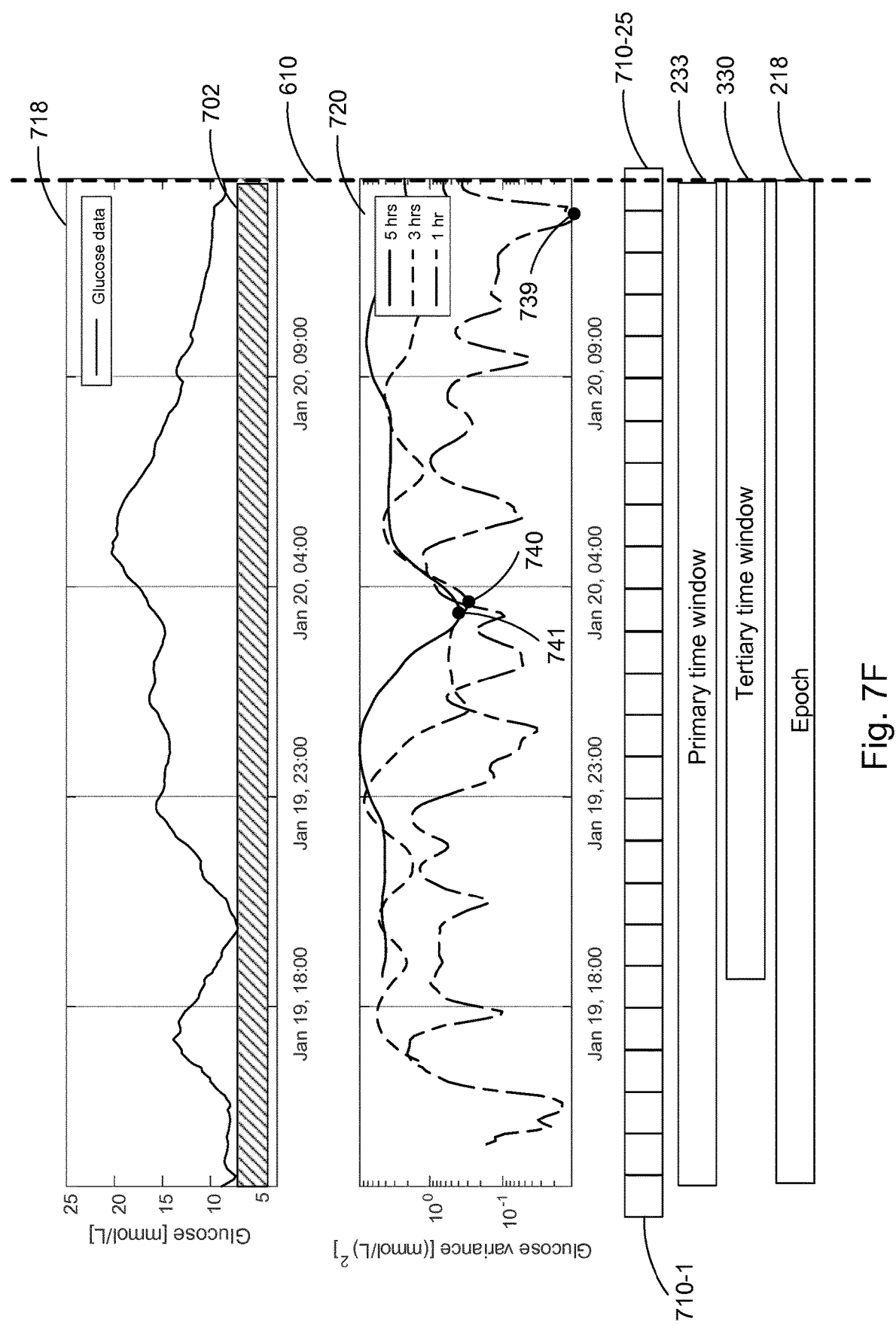

Referring to FIGS. 7E and 7F, the top panel 718 illustrates the glucose level as a function of time obtained from the plurality of glucose measurements within the time course. The second panel 720 shows the running variance of the glucose measurements with different window sizes of 5 hours, 3 hours and 1 hour, respectively. The smallest evaluated variance can be used to identify the titration subset of small glucose values, which can be used to evaluate the titration glucose level. The illustrated tertiary window 330 corresponds to the running average using a 5 hours window (secondary time window is 5 hours). For the glucose data illustrated in FIG. 7E the patient is on basal insulin only, hence low glucose values only relate to endogenous insulin and long acting insulin. In this case we are interested in the lowest glucose value rather than low variance since we know that basal insulin or endogenous insulin is causing the lowest values. The lowest running variance for the 1 hour window 736 is around 3:30. For the 3 hours window, the smallest running variance for the 3 hour window 737 is found around 4:45. For the 5 hours window, the lowest running variance for the 5 hour window 738 is found around 5:15. For the glucose data illustrated in FIG. 7F the patient is on basal and bolus insulin. The patient takes a correction bolus after dinner which causes glucose to decrease at around 20:00. In this case we are not interested in the lowest glucose value since it is caused by a bolus and not the basal insulin. The lowest running variance for the 1 hour window 739 is around 13:00. For the 3 hours window, the smallest running variance for the 3 hour window 740 is found around 03:20. The 3 hour window also has a dip at around 01:00 which is almost as low as the dip around 03:20. For the 5 hours window, the lowest running variance for the 5 hour window 741 is found around 03:40.

TABLE 1

Time detection of minimum values for running average of glucose measurements and running variance for glucose measurements.

|  | Minimum for 1 hour window | Minimum for 3 hour window | Minimum for 5 hour window |
|---|---|---|---|
| FIG. 7C (running average of glucose) | 09:00 | 09:30 | 10:00 |
| FIG. 7D (running average of glucose) | 20:30 | 17:00 | 19:00 |
| FIG. 7E (running variance of glucose) | 03:30 | 04:45 | 05:15 |
| FIG. 7F (running variance of glucose) | 13:00 | 03:20 | 03:40 |

Comparing FIG. 7C where running average is used with FIG. 7E, where running variance is used, the smallest variance was found at around 4:00 depending on the time window, whereas the smallest average is found between 9 and 10 also depending on the time window. In this case we are interested in the lowest value rather than low variance since we know that basal insulin or endogenous insulin is causing the lowest values.

Comparing FIG. 7D where running average is used with FIG. 7F, where running variance is used, the smallest variance was found at around 3:30 in the night (with frame size of 3 or 5 hours, the timing actually depends on the frame size), whereas the smallest running average is found around 17:00 and 19-20:30, also depending on the window or frame size. In this case we are not interested in the lowest glucose value since it is caused by a bolus and not the basal insulin.

Prior dose guidance algorithms for long acting insulin base their calculations on fasting glucose levels, where the glucose measurement for example has been tagged as a fasting glucose measurement. In the embodiment disclosed on FIGS. 7E and 7F we use a third evaluation mode to determine periods of fasting periods based on periods of low variance in glucose. The argumentation for identifying a titration glucose level in this way, is that glucose variance is typically higher during periods of external glucose entering the system than during fasting. This approach is created with MDI treatment in mind, where the algorithm can utilize information or identify that glucose levels are influenced e.g. by external short acting insulin. Therefore, a different approach is presented according to the embodiment disclosed in FIGS. 7A and 7B where we use a second evaluation mode, where a titration glucose level for dose guidance algorithms for long acting insulin is determined using low glucose values. The definition titration glucose level is used to emphasize that this is not necessarily a fasting glucose value, rather the glucose titration level to base dose calculations on is low glucose values. Instead of using periods of low variance in glucose, we use the information that the glucose is not influenced by short acting insulin, and we use periods of low average glucose within a specific time window. For example, we use a running average window of 3 hours and choose the window with the lowest value as the titration glucose level. This is useful in long acting insulin treatment since we are certain that there is no fast acting insulin causing the lowest values; all lowered glucose values are due to the long acting insulin or physiological changes.

We detect titration glucose level by selecting the lowest average of glucose levels during a predefined time interval (i.e. if the time predefined interval is 60 minutes and frequency of measurements is 5 minutes, choose the lowest of 288 12 consecutive measurements).

This approach calculates a moving average (MA) of N consecutive measurements, $$MA_{period,i} = \frac{1}{N} \sum_{k=i-(N-1)}^{i} G_k$$

where G is a glucose measurement, the subscript i is the sample at a specific point in time, N is the number of samples in each average, and the titration glucose level of a period is determined by $FG=\min(MA_{period})$ As opposed to methods that assume fasting occurs at predefined times, this approach mitigates people with irregular daily routines (shift workers etc.) and people whose daily routines deviate from normal practice (e.g. not having breakfast), see FIG. 7A. The frequency of continuous glucose measurements can vary, and can span for example from a near continuous signal and up to 1 hour.

Example 1: First Evaluation Mode—Subset of Lowest Measurements

This method is similar to the running average in that it targets low glucose levels. Therefore it is relevant in basal insulin treatment. This method is more sensitive to low values and noise than the moving average, which might be beneficial in scenarios of e.g. patients with high hyporisk and high glucose variability. As previously mentioned examples of an embodiment can be seen in FIGS. 7A and 7B.

Example 2: Second Evaluation Mode—Running or Moving Average

In basal insulin titration, typically fasting glucose levels from the past three days are used to determine a next dose size. In this embodiment we use DexCom G5 as an example. The CGM outputs glucose levels every 5 minutes, which represent the average glucose levels of the past 5 minutes. We detect TGL by selecting the lowest average glucose level over the past 0-24, 24-48 and 48-72 hours to obtain TGL of the past three days. For each 24 hour long time interval, a window of 60 minutes, or 12 consecutive CGM measurements, runs through the glucose data and average of each window is calculated.

This approach calculates a moving average (MA) of 12 consecutive measurements of 5 minute intervals using the following equation, $$MA_{0\text{-}24h,i} = \frac{1}{12} \sum_{k=i-11}^{i} G_k$$

where G is a glucose measurement and the subscript i refers to the current sample, and the fasting glucose of time interval 0-24 hours is determined by $$FG_{0\text{-}24h} = \min(MA_{0\text{-}24h})$$

As previously mentioned, two examples of results are shown in FIGS. 7C and 7D for time frames of 1, 3 and 5 hours.

In the first case, a patient is only on basal insulin and therefore the low glucose values can only be caused by basal insulin injections or endogenous insulin (or other natural causes). In the second case the patient is on MDI treatment and therefore low glucose values are not necessarily related to the basal injection or endogenous production, but could also be caused by a meal or correction bolus.

Example 3: Third Evaluation Mode—Moving Variance

Dose guidance algorithms for MDI treatment including long and fast acting insulin base their calculations on fasting glucose as well as pre-prandial glucose levels. For the purpose of determining periods of fasting to be used as a titration glucose level we detect periods of low variance in glucose. We do this because glucose variance is typically higher during periods of external glucose entering the system than during fasting. This method is similar to the moving average except that instead of calculating average in a time frame we calculate variance within the time frame. As previously mentioned example of embodiments can be seen in FIGS. 7E and 7F.

LISTS OF EMBODIMENTS

In a first list of embodiments is provided a basal titration adjustment device, adapted for adjusting a long acting insulin regimen, wherein the device is adapted for obtaining a titration glucose level based on small glucose measurements and the state of an insulin state indicator.

1. A basal titration adjustment device 250 for autonomously adjusting a long acting insulin medicament dosage in a prescribed insulin regimen for a subject, wherein the device comprises one or more processors 274 and a memory 192/290, the memory comprising:
   a first data structure 210 that includes the prescribed insulin regimen 212 including a basal insulin medicament dosage regimen 214, wherein the basal insulin medicament dosage regimen specifies the long acting insulin medicament dosage 216, an insulin state indicator 211, wherein the insulin state indicator 211 can indicate a short-acting-insulin-influence state, wherein the glucose measurements within the primary time window may be influenced by a short acting insulin medicament, and an only-long-acting-insulin-influence state, wherein the glucose measurements within the primary time window can be influenced by a long acting insulin medicament, but the measurements cannot be influenced by a short acting insulin medicament, and instructions that, when executed by the one or more processors, perform a method of:
   (A) obtaining, a first data set 228, the first data set comprising a plurality of glucose measurements of the subject taken over a time course and, for each respective glucose measurement 230 in the plurality of glucose measurements, a corresponding timestamp 232 representing when in the time course the respective glucose measurement was made;
   (B) obtaining a titration glucose level 246 based on small glucose measurements and the state of the insulin state indicator 211 by:
   (i) obtaining a primary time window 233 within the time course defining the period of time comprising the glucose measurements 236 in the first data set to be used for identifying the titration glucose level,
   (ii) identifying a titration subset of small glucose measurements 240, 269, 273, identified as a subset of small glucose measurements within the primary time window 233,
   (iii) obtaining the titration glucose level 246 computed as a measure of central tendency 244, 268, 274 of the titration subset of small glucose measurements 240, 269, 273, wherein the measure of central tendency represents a measure of small glucose measurements for the primary time window, and
   (iv) associating the titration glucose level 246 with the measure of central tendency 244, 268, 274;
   (C) adjusting or maintaining the long acting insulin medicament dosage 216 based upon the obtained titration glucose level 246.

2. The device of embodiment 1, wherein the obtaining the titration glucose level 246, in step B, further comprises:
   based on the status of the insulin state indicator, selecting one of the following evaluation modes:
   (B1) for the primary time window in a first evaluation mode, (i) obtaining an integer 234 defining the number of glucose measurements to be selected for the titration subset of small glucose measurements 240, (ii) identifying and selecting the titration subset of small glucose measurements 240 as a subset of smallest glucose measurements, by identifying and selecting the smallest glucose measurements within the primary time window 233, and ensuring that the number of measurements within the titration subset of small glucose measurements 240 equals the obtained integer 234, (iii) obtaining the measure of central tendency as a first glucose measure of central tendency 244, and computed as a measure of central tendency of the glucose measurements within the subset of small glucose measurements 240, and associating the titration glucose level 246 with the first glucose measure of central tendency 244,
   (B2) for the primary time window 233 in a second evaluation mode, obtaining a plurality of contemporaneously overlapping secondary time windows 260 within the primary time window 233, wherein each secondary time window 262 comprises a subset of overlapping glucose measurements 264 being a subset of the glucose measurements 236 in the primary time window 233, for each secondary time window 262 within the plurality of secondary time windows 260, computing a corresponding second glucose measure of central tendency 267, and thereby obtaining a plurality of second glucose measures of central tendency, wherein each respective second glucose measure of central tendency 267 is computed as a measure of central tendency of the glucose measurements within the corresponding secondary time window 262, and thereby obtaining a moving period of a measure of central tendency across the glucose measurements in the primary time window, for the plurality of second glucose measures of central tendency, identifying a smallest second glucose measure of central tendency 268 as the smallest second glucose measure of central tendency within the plurality of second glucose measures of central tendency, whereby the titration subset of small glucose measurements 269 is identified as the subset comprising the glucose measurements within the secondary time window 262 corresponding to the smallest second glucose measure of central tendency 268, and associating the titration glucose level 246 with the smallest second glucose measure of central tendency 268, or (B3) for the primary time window 233 in a third evaluation mode, obtaining a plurality of contemporaneously overlapping secondary time windows 260 within the primary time window 233, wherein each secondary time window 262 comprises a subset of overlapping glucose measurements 264 being a subset of the glucose measurements 236 in the primary time window 233, for each secondary time window 262 within the plurality of secondary time windows 260, computing a corresponding glucose measure of variability 271, and thereby obtaining a plurality of glucose measures of variability, wherein each respective glucose measure of variability 271 is computed as a measure of variability of the glucose measurements within the corresponding secondary time window 262, and thereby obtaining a moving period of a measure of variability across the glucose measurements in the primary time window, for the plurality of glucose measures of variability, identifying a smallest glucose measure of variability 272 as the smallest glucose measure of variability within the plurality of glucose measures of variability, whereby the titration subset of small glucose measurements 273 is identified as the subset comprising the glucose measurements within the secondary time window 262 corresponding to the smallest glucose measure of variability 272, and computing a smallest third glucose measure of central tendency 274 as a measure of central tendency of the titration subset of small glucose measurements 273, and associating the titration glucose level 246 with the smallest third glucose measure of central tendency 274.

3. The device of any of the embodiments 1 or 2, wherein the method further comprises:

in response to identifying the state of the insulin state indicator 211, selecting the first or the second evaluation mode, upon the occurrence that the state of the insulin state indicator is identified as the only-long-acting-insulin-influence state, and thereby using a preferred method for obtaining the titration glucose level 246, which is preferred for titration with a long acting insulin medicament, when it is ensured that no short acting insulin medicament influences the glucose measurements 236.

4. The device of any of embodiments 1 or 2, wherein the method further comprises:

in response to identifying the state of the insulin state indicator 310, selecting the third evaluation mode, upon the occurrence that the state of the insulin state indicator is identified as the a short-acting-insulin-influence state, and thereby using a preferred method for obtaining the titration glucose level 246, which is preferred for titration with a long acting insulin medicament, when it is identified that short acting insulin medicament may influence the glucose measurements 236.

5. The device of any one of the embodiments 2-4, wherein the measure of variability 271 is the variance.

6. The device of any one of the previous embodiments, wherein the measure of central tendency 244, 268, 274 is the mean value.

7. The device of any one of the previous embodiments, wherein the method is repeated on a recurring basis.

8. The device of any one of the embodiments 2-7, wherein the method further comprises:

obtaining a second data set 320 from one or more insulin pens 104 used by the subject to apply the prescribed insulin regimen, the second data set comprising a plurality of insulin medicament records over the time course, each insulin medicament record 321 in the plurality of medicament records comprising: (i) a respective insulin medicament injection event 322 representing an insulin medicament injection into the subject using a respective insulin pen in the one or more insulin pens 104 and (ii) a corresponding electronic timestamp 323 that is automatically generated by the respective insulin pen upon occurrence of the respective insulin medicament injection event;

for the first glucose measures of central tendency 244 in the first evaluation mode, associating the first glucose measure of central tendency with a tertiary time window 330 representing an evaluation period, wherein a most recent end point 614 of the tertiary time window is synchronized with a most recent end point 612 of the primary time window 233, and wherein the primary and the tertiary windows are of the same length, for the plurality of second glucose measures of central tendency in the second evaluation mode, associating each respective second glucose measure of central tendency 267 with a time indicator 331 representing the time of evaluation of the respective second glucose measure of central tendency, and thereby obtaining a plurality of time indicators defining a tertiary time window 330 representing an evaluation period, wherein a most recent end point 614 of the tertiary time window is synchronized with a most recent end point 612 of the primary time window, and wherein the length 615 of the tertiary time window 330 is smaller than the length 613 of the primary time window 233, or for the plurality of glucose measures of variability in the third evaluation mode, associating each respective glucose measure of variability 267 with a time indicator 331 representing the time of evaluation of the respective glucose measure of variability, and thereby obtaining a plurality of time indicators defining a tertiary time window 330 representing an evaluation period, wherein a most recent end point 614 of the tertiary time window is synchronized with a most recent end point 612 of the primary time window, and wherein the length 615 of the tertiary time window 330 is smaller than the length 613 of the primary time window 233; and associating the titration glucose level 246 with the tertiary time window 330;

applying a first characterization 335 to the tertiary time window 330, wherein the first characterization 335 is one of basal regimen adherent and basal regimen nonadherent, the tertiary time window 330 is deemed basal regimen adherent when the second data set 320 includes one or more medicament records that establish, on a temporal and quantitative basis, adherence with the prescribed basal insulin medicament dosage regimen 212 during the respective tertiary time window 330, and the tertiary time window is deemed basal regimen nonadherent when the second data set 320 fails to include one or more medicament records that establish, on a temporal and quantitative basis, adherence with the prescribed basal insulin medicament dosage regimen 212 during the tertiary time window 330; and wherein the adjusting the long acting insulin medicament dosage 216 in the basal insulin medicament dosage regimen 214 for the subject is based upon a titration glucose level 244 that is represented by a tertiary time window 330 that is deemed basal regimen adherent and by excluding a titration glucose level 244 that is represented by a tertiary time window 330 that is deemed basal regimen nonadherent.

9. The device according to any of the previous embodiments, wherein the first data structure comprises, a plurality of consecutive epochs, wherein each respective epoch 218 is associated with a basal insulin medicament dosage 216, indicating when the basal insulin medicament is to be injected within the respective epoch 218, and how much of the basal insulin medicament is to be injected, and thereby providing a temporal and quantitative basis for the first characterization.

10. The device according to embodiments 8 and 9, wherein the length 615 of the tertiary window 330 is longer than or the same as the length 619 of each of the epochs 218.

11. The device of any of the embodiments 8-10, wherein the end point 614 of the tertiary time window is synchronized with an end point 618 of a current epoch, wherein the current epoch is the most recent completed epoch within the plurality of epochs.

12. The device of embodiment 9, wherein each respective epoch 218 of the plurality of epochs is associated with a tertiary time window 330, and thereby obtaining a plurality of tertiary time windows, wherein each tertiary time window represents an evaluation period, wherein each tertiary window is aligned with the respective epoch on a temporal bases, and wherein each tertiary time window 330 is associated with a titration glucose level 246.

13. The device of any of the previous embodiments, wherein the first data structure comprises a specification of temporal and quantitative basis for administration of the long acting insulin medicament, for each of the epochs 218 within the plurality of epochs.

14. The device of any of embodiments 8-13, wherein the quantitative basis for the long acting insulin medicament is a function of the titration glucose level.

15. The device of any of embodiments 9-14, wherein the temporal basis is specified as one injection for each epoch 218 within the plurality of epochs.

16. The device of any of the embodiments 9-15, wherein each epoch 218 in the plurality of epochs is a calendar day or a calendar week.

17. The device of any of the previous embodiments, wherein successive measurements in the plurality of glucose measurements are autonomously taken from the subject at an interval rate of 5 minutes or less, 3 minutes or less, or 1 minute or less.

18. The device of any of the previous embodiments, wherein the device further comprises a wireless receiver 284, and wherein the first data set is obtained wirelessly from a glucose sensor 102 affixed to the subject and/or the second data set is obtained wirelessly from the one or more insulin pens 104.

19. The device of any of the previous embodiments, wherein the first data structure further comprises a hypoglycemic risk state indicator, wherein the hypoglycemic risk state indicator can indicate a high hypoglycemic risk state, wherein the subject may have a high hypoglycemic risk or wherein a high variability across the plurality of glucose measurements can be observed, and a non-high hypoglycemic risk state, wherein the subject may have a non-high hypoglycemic risk or wherein a low variability across the plurality of glucose measurements can be observed, and wherein the method further comprises:

in response to identifying the state of the hypoglycemic risk state indicator, selecting the first evaluation mode, upon the occurrence that the state of the hypoglycemic risk state indicator is identified as the high hypoglycemic risk state, and thereby using a method for obtaining the titration glucose level 246 which is more sensitive to low glucose values and noise.

20. The device of any of the embodiments 2-19, wherein the secondary time window is 50 minutes to 70 minutes, 60 minutes to 120 minutes, 120 minutes to 180 minutes, 180 minutes to 300 minutes, or 300-500 minutes.

21. The device of any of the embodiments 2-20, wherein successive measurements in the plurality of glucose measurements are autonomously taken from the subject at an interval rate of 4 minutes to 6 minutes.

22. The device of any of embodiments 2-19, wherein successive measurements in the plurality of glucose measurements are autonomously taken from the subject at an interval rate of 4 minutes to 6 minutes, and wherein the secondary time window is 50 minutes to 70 minutes.

23. The device of any of embodiments 2-19, wherein successive measurements in the plurality of glucose measurements are autonomously taken from the subject at an interval rate of 4 minutes to 6 minutes, and wherein the secondary time window is 180 minutes to 300 minutes.

24. The device of any of embodiments 2-19, wherein successive measurements in the plurality of glucose measurements are autonomously taken from the subject at an interval rate of 40 minutes to 80 minutes, and wherein the secondary time window is 180 minutes to 310 minutes.

25. The device of any one of the previous embodiments, wherein the method further comprises:

obtaining a second data set (320) from one or more insulin pens (104) used by the subject to apply the prescribed insulin regimen, the second data set comprising a plurality of insulin medicament records over the time course, each insulin medicament record (321) in the plurality of medicament records comprising: (i) a respective insulin medicament injection event (322) representing an insulin medicament injection into the subject using a respective insulin pen in the one or more insulin pens (104) and (ii) a corresponding electronic timestamp (323) that is automatically generated by the respective insulin pen upon occurrence of the respective insulin medicament injection event, (iii) the type of insulin medicament indicating whether the injected insulin medicament is a short acting insulin medicament type or a long acting insulin medicament type.

26. The device of any of the previous embodiments, wherein the prescribed insulin regimen further comprises a bolus insulin medicament dosage regimen, wherein the bolus insulin medicament dosage regimen specifies the [amount of] short acting insulin dosage.

27. The device according to any of the embodiments 25-26, wherein the prescribed insulin regimen 212 further comprises a duration of action for the short acting insulin medicament, wherein the duration of action of a medicament specifies the duration that a measurable medicament effect persist, and thereby influences the glucose level.

28. The device according to any of embodiments 25-27, wherein the prescribed insulin regimen 212 comprises a duration of action for the long acting insulin medicament, wherein the duration of action of a medicament specifies the duration that a measurable medicament effect persist, and thereby influences the glucose level.

29. The device of any of the embodiments 25-27, wherein the insulin state indicator 211 indicates the short-acting-insulin-influence state based on the second data set and the duration of action for the short acting insulin medicament.

30. The device of any of the embodiments 25-29, wherein the insulin state indicator 211 indicates the only-long-acting-insulin-influence state based on the second data set and the duration of action for the short acting insulin medicament.

31. The device of any of the embodiments 25-30, wherein the insulin state indicator 211 indicates the only-long-acting-insulin-influence state further based on the duration of action for the long acting insulin medicament.

32. The device of any of the previous embodiments, wherein the titration glucose level 246 is associated with the first glucose measure of central tendency 244 by assigning the value of the first measure of central tendency to the titration glucose level.

33. The device of any of the previous embodiments, wherein the measurements in the plurality of glucose measurements are autonomously obtained by a continuous glucose monitor.

34. The device according to any of the previous embodiments, wherein the titration glucose level 246 is the glucose level used as input to an algorithm for maintaining or adjusting the long acting insulin medicament dosage 216.

35. The device according to any of the previous embodiments, wherein the glucose measurements 236 in the first data set to be used for identifying the titration glucose level, comprises the titration subset of small glucose measurements 240, 269, 273.

36. The device according to any of the previous embodiments, wherein the glucose measurements comprised in the titration subset of small glucose measurements 240, 269, 273 have values smaller than a lower percentile of the glucose measurements 236, wherein the lower percentile ranges from the $0.1^{th}$ percentile to the 50th percentile, wherein a $P^{th}$ percentile is defined as the lowest glucose measurement that is greater than P % of the glucose measurements 236 in the first data set to be used for identifying the titration subset 240, 269, 273 within the primary time window 233.

(iii) obtaining the titration glucose level 246 computed as a measure of central tendency 244, 268, 274 of the titration subset of small glucose measurements 240, 269, 273, wherein the measure of central tendency represents a measure of small glucose measurements for the primary time window, and (iv) associating the titration glucose level 246 with the measure of central tendency 244, 268, 274;

37. The device of any of the previous embodiments, wherein the obtaining the titration glucose level 246, in step B, further comprises:

verifying that the values of the glucose measurements comprised in the titration subset of small glucose measurements 240, 269, 273 are smaller than the lower percentile of the glucose measurements 236.

38. The device of any of the embodiments 36-37, wherein the lower percentile is the $5^{th}$ percentile, wherein a $5^{th}$ percentile is defined as the lowest glucose measurement that is greater than 5% of the glucose measurements 236 in the first data set to be used for identifying the titration subset 240, 269, 273.

39. A method for autonomously adjusting a long acting insulin medicament dosage in a prescribed insulin regimen for a subject, at a computer comprising one or more processors and a memory:

the memory storing:

a first data structure 210 that includes the prescribed insulin regimen 212 including a basal insulin medicament dosage regimen 214, wherein the basal insulin medicament dosage regimen specifies the amount of long acting insulin medicament dosage 216, an insulin state indicator 211, wherein the insulin state indicator 211 can indicate a short-acting-insulin-influence state, wherein the glucose measurements within the primary time window may be influenced by a short acting insulin medicament, and an only-long-acting-insulin-influence state, wherein the glucose measurements within the primary time window can be influenced by a long acting insulin medicament, but the measurements cannot be influenced by a short acting insulin medicament, and the memory further storing instructions that, when executed by the one or more processors, perform a method of:

(A) obtaining, a first data set 228, the first data set comprising a plurality of glucose measurements of the subject taken over a time course and, for each respective glucose measurement 230 in the plurality of glucose measurements, a corresponding timestamp 232 representing when in the time course the respective glucose measurement was made;

(B) obtaining a titration glucose level 246 based on small glucose measurements and the state of the insulin state indicator 211 by:

(i) obtaining a primary time window 233 within the time course defining the period of time comprising the glucose measurements 236 in the first data set to be used for identifying the titration glucose level, (ii) identifying a titration subset of small glucose measurements 240, 269, 273, identified as a subset of small glucose measurements within the primary time window (233), (iii) obtaining the titration glucose level 246 computed as a measure of central tendency 244, 268, 274 of the titration subset of small glucose measurements 240, 269, 273, wherein the measure of central tendency represents a measure of small glucose measurements for the primary time window, and (iv) associating the titration glucose level 246 with the measure of central tendency 244, 268, 274;

(C) adjusting or maintaining the long acting insulin medicament dosage 216 based upon the obtained titration glucose level 246.

40. A computer program comprising instructions that, when executed by a computer having one or more processors and a memory, perform the method of embodiment 39.

41. A computer-readable data carrier having stored thereon the computer program according to embodiment 39.

In a second list of embodiments is provided a basal titration adjustment device, adapted for adjusting a long acting insulin regimen, wherein the device is adapted for obtaining a titration glucose level based on small glucose measurements.

1. A basal titration adjustment device 250 for autonomously adjusting a long acting insulin medicament dosage in a prescribed insulin regimen for a subject, wherein the device comprises one or more processors 274 and a memory 192/290, the memory comprising:

a first data structure 210 that includes the prescribed insulin regimen 212 including a basal insulin medicament dosage regimen 214, wherein the basal insulin medicament dosage regimen specifies the amount of long acting insulin medicament dosage 216, and instructions that, when executed by the one or more processors, perform a method of:

(A) obtaining, a first data set 228, the first data set comprising a plurality of glucose measurements of the subject taken over a time course and, for each respective glucose measurement 230 in the plurality of glucose measurements, a corresponding timestamp 232 representing when in the time course the respective glucose measurement was made;

(B) obtaining a titration glucose level 246 by:

(i) obtaining a primary time window 233 within the time course defining the period of time comprising the glucose measurements 236 in the first data set to be used for identifying the titration glucose level, (ii) identifying a titration subset of small glucose measurements 240, 269, 273, identified as a subset of small glucose measurements within the primary time window 233, (iii) obtaining the titration glucose level 246 computed as a measure of central tendency 244, 268, 274 of the titration subset of small glucose measurements 240, 269, 273, wherein the measure of central tendency represents a measure of small glucose measurements for the primary time window, and (iv) associating the titration glucose level 246 with the measure of central tendency 244, 268, 274;

(C) adjusting or maintaining the long acting insulin medicament dosage 216 based upon the obtained titration glucose level 246.

2. The device of embodiment 1, wherein the obtaining the titration glucose level (246), in step B, further comprises:

selecting one of the following evaluation modes:

(B1) for the primary time window in a first evaluation mode, (i) obtaining an integer 234 defining the number of glucose measurements to be selected for the subset of glucose measurements 240, (ii) identifying and selecting the titration subset of small glucose measurements 240 as a subset of smallest glucose measurements, by identifying and selecting the smallest glucose measurements within the primary time window 233, and ensuring that the number of measurements within the titration subset of small glucose measurements 240 equals the obtained integer 234, (iii) obtaining the measure of central tendency as a first glucose measure of central tendency 244, and computed as a measure of central tendency of the glucose measurements within the subset of small glucose measurements 240, and associating the titration glucose level 246 with the first glucose measure of central tendency 244, (B2) for the primary time window 233 in a second evaluation mode, obtaining a plurality of contemporaneously overlapping secondary time windows 260 within the primary time window (233), wherein each secondary time window 262 comprises a subset of overlapping glucose measurements 264 being a subset of the glucose measurements 236 in the primary time window 233, for each secondary time window 262 within the plurality of secondary time windows 260, computing a corresponding second glucose measure of central tendency 267, and thereby obtaining a plurality of second glucose measures of central tendency, wherein each respective second glucose measure of central tendency 267 is computed as a measure of central tendency of the glucose measurements within the corresponding secondary time window 262, and thereby obtaining a moving period of a measure of central tendency across the glucose measurements in the primary time window, for the plurality of second glucose measures of central tendency, identifying a smallest second glucose measure of central tendency 268 as the smallest second glucose measure of central tendency within the plurality of second glucose measures of central tendency, whereby the titration subset of small glucose measurements 269 is identified as the subset comprising the glucose measurements within the secondary time window 262 corresponding to the smallest second glucose measure of central tendency 268, and associating the titration glucose level 246 with the smallest second glucose measure of central tendency 268, or (B3) for the primary time window 233 in a third evaluation mode, obtaining a plurality of contemporaneously overlapping secondary time windows 260 within the primary time window 233, wherein each secondary time window 262 comprises a subset of overlapping glucose measurements 264 being a subset of the glucose measurements (236) in the primary time window 233, for each secondary time window 262 within the plurality of secondary time windows 260, computing a corresponding glucose measure of variability 271, and thereby obtaining a plurality of glucose measures of variability, wherein each respective glucose measure of variability 272 is computed as a measure of variability of the glucose measurements within the corresponding secondary time window 262, and thereby obtaining a moving period of a measure of variability across the glucose measurements in the primary time window, for the plurality of glucose measures of variability, identifying a smallest glucose measure of variability 272 as the smallest glucose measure of variability within the plurality of glucose measures of variability, whereby the titration subset of small glucose measurements 273 is identified as the subset comprising the glucose measurements within the secondary time window 262 corresponding to the smallest glucose measure of variability 272, and computing a smallest third glucose measure of central tendency 274 as a measure of central tendency of the titration subset of small glucose measurements 273, and associating the titration glucose level 246 with the smallest third glucose measure of central tendency 274.

In a third list of embodiments is provided a basal titration adjustment device, adapted for adjusting a long acting insulin regimen, wherein the device is adapted for obtaining a titration glucose level based on small glucose measurements.

1. A basal titration adjustment device 250 for autonomously adjusting a long acting insulin medicament dosage in a prescribed basal insulin regimen for a subject, wherein the device comprises one or more processors 274 and a memory 192/290, the memory comprising:

a prescribed insulin regimen 212 including a basal insulin medicament dosage regimen 214, wherein the basal insulin medicament dosage regimen specifies the amount of long acting insulin medicament dosage 216, and instructions that, when executed by the one or more processors, perform a method of:

(A) obtaining, a first data set 228, the first data set comprising a plurality of glucose measurements of the subject taken over a time course and, for each respective glucose measurement 230 in the plurality of glucose measurements, a corresponding timestamp 232 representing when in the time course the respective glucose measurement was made;

(B) obtaining a titration glucose level 246 being the glucose level used as input to an algorithm for maintaining or adjusting the long acting insulin medicament dosage, wherein the titration glucose level is based on a titration subset of small glucose measurements, by:

(i) obtaining a primary time window 233 within the time course defining the period of time comprising the glucose measurements 236 in the first data set to be used for identifying the titration subset of small glucose measurements 240, 269, 273 and for obtaining the titration glucose level for the primary time window 233, wherein each of the glucose measurements 236 has a timestamp 232 within the primary time window 233, (ii) identifying the titration subset of small glucose measurements 240, 269, 273, identified as a subset of small glucose measurements within the primary time window 233, (iii) obtaining the titration glucose level 246, computed as a measure of central tendency 244, 268, 274 of the titration subset of small glucose measurements 240, 269, 273, wherein the measure of central tendency represents a measure of small glucose measurements for the primary time window, and (iv) associating the titration glucose level 246 with the measure of central tendency 244, 268, 274, by assigning the value of measure of central tendency to the titration glucose level;

(C) adjusting or maintaining the long acting insulin medicament dosage 216 based upon the obtained titration glucose level 246.

2. The device of embodiment 1, wherein the obtaining the titration glucose level (246), in step B, further comprises: selecting one of the following evaluation modes:

(B1) for the primary time window in a first evaluation mode, (i) obtaining an integer 234 defining the number of glucose measurements to be selected for the subset of glucose measurements 240, (ii) identifying and selecting the titration subset of small glucose measurements 240 as a subset of smallest glucose measurements, by identifying and selecting the smallest glucose measurements within the primary time window 233, and ensuring that the number of measurements within the titration subset of small glucose measurements 240 equals the obtained integer 234, (iii) obtaining the measure of central tendency as a first glucose measure of central tendency 244, and computed as a measure of central tendency of the glucose measurements within the subset of small glucose measurements 240, and associating the titration glucose level 246 with the first glucose measure of central tendency 244.

3. The device of embodiment 1, wherein the obtaining the titration glucose level (246), in step B, further comprises:

(B2) for the primary time window 233 in a second evaluation mode, obtaining a plurality of contemporaneously overlapping secondary time windows 260 within the primary time window (233), wherein each secondary time window 262 comprises a subset of overlapping glucose measurements 264 being a subset of the glucose measurements 236 in the primary time window 233, for each secondary time window 262 within the plurality of secondary time windows 260, computing a corresponding second glucose measure of central tendency 267, and thereby obtaining a plurality of second glucose measures of central tendency, wherein each respective second glucose measure of central tendency 267 is computed as a measure of central tendency of the glucose measurements within the corresponding secondary time window 262, and thereby obtaining a moving period of a measure of central tendency across the glucose measurements in the primary time window, for the plurality of second glucose measures of central tendency, identifying a smallest second glucose measure of central tendency 268 as the smallest second glucose measure of central tendency within the plurality of second glucose measures of central tendency, whereby the titration subset of small glucose measurements 269 is identified as the subset comprising the glucose measurements within the secondary time window 262 corresponding to the smallest second glucose measure of central tendency 268, and associating the titration glucose level 246 with the smallest second glucose measure of central tendency 268.

4. The device of embodiment 1, wherein the obtaining the titration glucose level (246), in step B, further comprises:

obtaining a percentage defining a titration percentile defining the number of glucose measurements to be selected for the titration subset of small glucose measurements, (ii) identifying and selecting the titration subset of small glucose measurements as a subset of smallest glucose measurements, by identifying and selecting the glucose measurements defined by the titration percentile of the glucose measurements (236), wherein the titration percentile ranges from the $0.1^{th}$ percentile to the $50^{th}$ percentile, and is smaller than or equal to the lower percentile, and wherein a $P^{th}$ percentile is defined as the lowest glucose measurement that is greater than P % of the glucose measurements (236) in the first data set to be used for identifying the titration subset within the primary time window (233), (iii) obtaining the measure of central tendency as a fourth glucose measure of central tendency, and computed as a measure of central tendency of the glucose measurements within the subset of small glucose measurements (240), and associating the titration glucose level (246) with the fourth glucose measure of central tendency (244), by assigning the value of the fourth measure of central tendency to the titration glucose level.

5. The device of any of the previous embodiments, wherein the measurements in the plurality of glucose measurements are autonomously obtained by a continuous glucose monitor from the subject In a fourth list of embodiments is provided a basal titration adjustment device, adapted for adjusting a long acting insulin regimen, wherein the device is adapted for obtaining a titration glucose level based on small glucose measurements.

1. A basal titration adjustment device 250 for autonomously adjusting a long acting insulin medicament dosage in a prescribed insulin regimen for a subject, wherein the device comprises one or more processors 274 and a memory 192/290, the memory comprising:

a prescribed insulin regimen 212 including a basal insulin medicament dosage regimen 214, wherein the basal insulin medicament dosage regimen specifies the amount of long acting insulin medicament dosage 216, and instructions that, when executed by the one or more processors, perform a method of:

(A) obtaining, a first data set 228, the first data set comprising a plurality of glucose measurements of the subject taken over a time course and, for each respective glucose measurement 230 in the plurality of glucose measurements, a corresponding timestamp 232 representing when in the time course the respective glucose measurement was made;

(B) obtaining a titration glucose level 246 being the glucose level used as input to an algorithm for maintaining or adjusting the long acting insulin medicament dosage, wherein the titration glucose level is based on a titration subset of small glucose measurements, by:

(i) obtaining a primary time window 233 within the time course defining the period of time comprising the glucose measurements 236 in the first data set to be used for identifying the titration subset of small glucose measurements 240, 269, 273 and for obtaining the titration glucose level for the primary time window 233, wherein each of the glucose measurements 236 has a timestamp 232 within the primary time window 233, (ii) identifying the titration subset of small glucose measurements 240, 269, 273, identified as a subset of small glucose measurements within the primary time window 233, (iii) obtaining the titration glucose level 246, computed as a measure of central tendency 244, 268, 274 of the titration subset of small glucose measurements 240, 269, 273, wherein the measure of central tendency represents a measure of small glucose measurements for the primary time window, and (iv) associating the titration glucose level 246 with the measure of central tendency 244, 268, 274, by assigning the value of measure of central tendency to the titration glucose level;

(C) adjusting or maintaining the long acting insulin medicament dosage 216 based upon the obtained titration glucose level 246.

2. The device of embodiment 1, wherein the obtaining the titration glucose level (246), in step B, further comprises:

selecting one of the following evaluation modes:

(B1) for the primary time window in a first evaluation mode, (i) obtaining an integer 234 defining the number of glucose measurements to be selected for the subset of glucose measurements 240, (ii) identifying and selecting the titration subset of small glucose measurements 240 as a subset of smallest glucose measurements, by identifying and selecting the smallest glucose measurements within the primary time window 233, and ensuring that the number of measurements within the titration subset of small glucose measurements 240 equals the obtained integer 234, (iii) obtaining the measure of central tendency as a first glucose measure of central tendency 244, and computed as a measure of central tendency of the glucose measurements within the subset of small glucose measurements 240, and associating the titration glucose level 246 with the first glucose measure of central tendency 244.

3. The device of embodiment 1, wherein the obtaining the titration glucose level (246), in step B, further comprises:

(B2) for the primary time window 233 in a second evaluation mode, obtaining a plurality of contemporaneously overlapping secondary time windows 260 within the primary time window (233), wherein each secondary time window 262 comprises a subset of overlapping glucose measurements 264 being a subset of the glucose measurements 236 in the primary time window 233, for each secondary time window 262 within the plurality of secondary time windows 260, computing a corresponding second glucose measure of central tendency 267, and thereby obtaining a plurality of second glucose measures of central tendency, wherein each respective second glucose measure of central tendency 267 is computed as a measure of central tendency of the glucose measurements within the corresponding secondary time window 262, and thereby obtaining a moving period of a measure of central tendency across the glucose measurements in the primary time window, for the plurality of second glucose measures of central tendency, identifying a smallest second glucose measure of central tendency 268 as the smallest second glucose measure of central tendency within the plurality of second glucose measures of central tendency, whereby the titration subset of small glucose measurements 269 is identified as the subset comprising the glucose measurements within the secondary time window 262 corresponding to the smallest second glucose measure of central tendency 268, and associating the titration glucose level 246 with the smallest second glucose measure of central tendency 268.

4. The device according to any of the embodiments 1-3, wherein the prescribed insulin regimen 212 further comprises a duration of action for the short acting insulin medicament, wherein the duration of action of a medicament specifies the duration that a measurable medicament effect persist, and thereby influences the glucose level.

5. The device according to any of embodiments 1-4, wherein the prescribed insulin regimen 212 comprises a duration of action for the long acting insulin medicament, wherein the duration of action of a medicament specifies the duration that a measurable medicament effect persist, and thereby influences the glucose level.

6. The device of any one of the embodiments 1-5, wherein the method further comprises:

obtaining a second data set 320 from one or more insulin pens 104 used by the subject to apply the prescribed insulin regimen, the second data set comprising a plurality of insulin medicament records over the time course, each insulin medicament record 321 in the plurality of medicament records comprising: (i) a respective insulin medicament injection event 322 representing an insulin medicament injection into the subject using a respective insulin pen in the one or more insulin pens 104 and (ii) a corresponding electronic timestamp 323 that is automatically generated by the respective insulin pen upon occurrence of the respective insulin medicament injection event, (iii) the type of insulin medicament indicating whether the injected insulin medicament is a short acting insulin medicament type or a long acting insulin medicament type, wherein the method further comprises (i) using the second data set and the duration of action to obtain the glucose measurements within the primary time window 233 that are not influenced by the short acting insulin, wherein the titration subset of small glucose measurements are identified within the glucose measurements within the primary time window 233 that are not influenced by the short acting insulin.

7. The device of any of the previous embodiments, wherein the measurements in the plurality of glucose measurements are autonomously obtained by a continuous glucose monitor from the subject

REFERENCES CITED AND ALTERNATIVE EMBODIMENTS

All references cited herein are incorporated herein by reference in their entirety and for all purposes to the same extent as if each individual publication or patent or patent application was specifically and individually indicated to be incorporated by reference in its entirety for all purposes.

The present invention can be implemented as a computer program product that comprises a computer program mechanism embedded in a nontransitory computer readable storage medium. For instance, the computer program product could contain the program modules shown in any combination of FIG. 1, 2, or 3 and/or described in FIG. 4. These program modules can be stored on a CD-ROM, DVD, magnetic disk storage product, or any other non-transitory computer readable data or program storage product.

Many modifications and variations of this invention can be made without departing from its spirit and scope, as will be apparent to those skilled in the art. The specific embodiments described herein are offered by way of example only. The embodiments were chosen and described in order to best explain the principles of the invention and its practical applications, to thereby enable others skilled in the art to best utilize the invention and various embodiments with various modifications as are suited to the particular use contemplated. The invention is to be limited only by the terms of the appended claims, along with the full scope of equivalents to which such claims are entitled.

The invention claimed is:

1. A device for adjusting a long acting insulin medicament dosage in a prescribed insulin regimen for a subject, wherein the device comprises one or more processors and a memory, the memory comprising:

a first data structure that includes the prescribed insulin regimen including a basal insulin medicament dosage regimen, wherein the basal insulin medicament dosage regimen specifies the amount of long acting insulin medicament dosage, and instructions that, when executed by the one or more processors, perform a method of:

(A) obtaining, a first data set, the first data set comprising a plurality of glucose measurements of the subject taken over a time course and, for each respective glucose measurement in the plurality of glucose measurements, a corresponding timestamp representing when in the time course the respective glucose measurement was made;

(B) obtaining a titration glucose level based on small glucose measurements and the state of the insulin state indicator by:
  (i) obtaining a primary time window within the time course defining the period of time comprising the glucose measurements in the first data set to be used for identifying the titration glucose level,
  (ii) identifying a titration subset of small glucose measurements, identified as a subset of small glucose measurements within the primary time window,
  (iii) obtaining the titration glucose level computed as a measure of central tendency of the titration subset of small glucose measurements, wherein the measure of central tendency represents a measure of small glucose measurements for the primary time window,
  (iv) associating the titration glucose level with the measure of central tendency;

(C) adjusting or maintaining the long acting insulin medicament dosage based upon the obtained titration glucose level, and wherein the first data structure further comprises an insulin state indicator, wherein the insulin state indicator can indicate a short-acting-insulin-influence state, wherein the glucose measurements within the primary time window may be influenced by a short acting insulin medicament, and an only-long-acting-insulin-influence state, wherein the glucose measurements within the primary time window can be influenced by a long acting insulin medicament, but the measurements cannot be influenced by a short acting insulin medicament.

2. The device of claim 1, wherein the obtaining the titration glucose level, in step B, further comprises:

based on the status of the insulin state indicator, selecting one of the following evaluation modes:

(B1) for the primary time window in a first evaluation mode,
  (i) obtaining an integer defining the number of glucose measurements to be selected for the titration subset of small glucose measurements,
  (ii) identifying and selecting the titration subset of small glucose measurements as a subset of smallest glucose measurements, by identifying and selecting the smallest glucose measurements within the primary time window, and ensuring that the number of measurements within the titration subset of small glucose measurements equals the obtained integer, (iii) obtaining the measure of central tendency as a first glucose measure of central tendency, and computed as a measure of central tendency of the glucose measurements within the subset of small glucose measurements, and associating the titration glucose level with the first glucose measure of central tendency, (B2) for the primary time window in a second evaluation mode, obtaining a plurality of contemporaneously overlapping secondary time windows within the primary time window, wherein each secondary time window comprises a subset of overlapping glucose measurements being a subset of the glucose measurements in the primary time window, for each secondary time window within the plurality of secondary time windows, computing a corresponding second glucose measure of central tendency, and thereby obtaining a plurality of second glucose measures of central tendency, wherein each respective second glucose measure of central tendency is computed as a measure of central tendency of the glucose measurements within the corresponding secondary time window, for the plurality of second glucose measures of central tendency, identifying a smallest second glucose measure of central tendency as the smallest second glucose measure of central tendency within the plurality of second glucose measures of central tendency, whereby the titration subset of small glucose measurements is identified as the subset comprising the glucose measurements within the secondary time window corresponding to the smallest second glucose measure of central tendency, and associating the titration glucose level with the smallest second glucose measure of central tendency, or (B3) for the primary time window in a third evaluation mode, obtaining a plurality of contemporaneously overlapping secondary time windows within the primary time window, wherein each secondary time window comprises a subset of overlapping glucose measurements being a subset of the glucose measurements in the primary time window, for each secondary time window within the plurality of secondary time windows, computing a corresponding glucose measure of variability, and thereby obtaining a plurality of glucose measures of variability, wherein each respective glucose measure of variability is computed as a measure of variability of the glucose measurements within the corresponding secondary time window, for the plurality of glucose measures of variability, identifying a smallest glucose measure of variability as the smallest glucose measure of variability within the plurality of glucose measures of variability, whereby the titration subset of small glucose measurements is identified as the subset comprising the glucose measurements within the secondary time window corresponding to the smallest glucose measure of variability, and computing a smallest third glucose measure of central tendency as a measure of central tendency of the titration subset of small glucose measurements, and associating the titration glucose level with the smallest third glucose measure of central tendency.

3. The device of claim 2, wherein the secondary time window is 50 minutes to 70 minutes, 60 minutes to 120 minutes, 120 minutes to 180 minutes, or 180 minutes to 300 minutes.

4. The device of claim 2, wherein successive measurements in the plurality of glucose measurements are autonomously taken from the subject at an interval rate of 4 minutes to 6 minutes, and wherein the secondary time window is 180 minutes to 300 minutes.

5. The device of claim 1, wherein the method further comprises:

in response to identifying the state of the insulin state indicator, selecting the first or the second evaluation mode, upon the occurrence that the state of the insulin state indicator is identified as the only-long-acting-insulin-influence state, and thereby using a preferred method for obtaining the titration glucose level, which is preferred for titration with a long acting insulin medicament, when it is ensured that no short acting insulin medicament influences the glucose measurements.

6. The device of claim 1, wherein the method further comprises:

in response to identifying the state of the insulin state indicator, selecting the third evaluation mode, upon the occurrence that the state of the insulin state indicator is identified as the a short-acting-insulin-influence state, and thereby using a preferred method for obtaining the titration glucose level, which is preferred for titration with a long acting insulin medicament, when it is identified that short acting insulin medicament may influence the glucose measurements.

7. The device of claim 1, wherein the method further comprises:

obtaining a second data set from one or more insulin pens used by the subject to apply the prescribed insulin regimen, the second data set comprising a plurality of insulin medicament records over the time course, each insulin medicament record in the plurality of medicament records comprising:

(i) a respective insulin medicament injection event representing an insulin medicament injection into the subject using a respective insulin pen in the one or more insulin pens, (ii) a corresponding electronic timestamp that is automatically generated by the respective insulin pen upon occurrence of the respective insulin medicament injection event, and (iii) the type of insulin medicament indicating whether the injected insulin medicament is a short acting insulin medicament type or a long acting insulin medicament type.

8. The device according to claim 7, wherein the prescribed insulin regimen further comprises a duration of action for the short acting insulin medicament, wherein the duration of action of a medicament specifies the duration that a measurable medicament effect persist, and thereby influences the glucose level.

9. The device according to claim 7, wherein the prescribed insulin regimen comprises a duration of action for the long acting insulin medicament, wherein the duration of action of a medicament specifies the duration that a measurable medicament effect persist, and thereby influences the glucose level.

10. The device of claim 7, wherein the insulin state indicator indicates the short-acting-insulin-influence state based on the second data set and the duration of action for the short acting insulin medicament.

11. The device of claim 7, wherein the insulin state indicator indicates the only-long-acting-insulin-influence state based on the second data set and the duration of action for the short acting insulin medicament.

12. The device of claim 1, wherein the prescribed insulin regimen further comprises a bolus insulin medicament dosage regimen, wherein the bolus insulin medicament dosage regimen specifies the short acting insulin dosage.

13. The device of claim 1, wherein the first data structure further comprises a hypoglycemic risk state indicator, wherein the hypoglycemic risk state indicator can indicate a high hypoglycemic risk state, wherein the subject may have a high hypoglycemic risk or wherein a high variability across the plurality of glucose measurements can be observed, and a non-high hypoglycemic risk state, wherein the subject may have a non-high hypoglycemic risk or wherein a low variability across the plurality of glucose measurements can be observed, and wherein the method further comprises:
  in response to identifying the state of the hypoglycemic risk state indicator,
  selecting the first evaluation mode, upon the occurrence that the state of the hypoglycemic risk state indicator is identified as the high hypoglycemic risk state, and thereby using a method for obtaining the titration glucose level which is more sensitive to low glucose values and noise.

14. A method for autonomously adjusting a long acting insulin medicament dosage in a prescribed insulin regimen for a subject, at a computer comprising one or more processors and a memory:
  the memory storing:
  a first data structure that includes the prescribed insulin regimen including a basal insulin medicament dosage regimen, wherein the basal insulin medicament dosage regimen specifies the amount of long acting insulin medicament dosage, and the memory further storing instructions that, when executed by the one or more processors, perform a method of:

(A) obtaining, a first data set, the first data set comprising a plurality of glucose measurements of the subject taken over a time course and, for each respective glucose measurement in the plurality of glucose measurements, a corresponding timestamp representing when in the time course the respective glucose measurement was made;

(B) obtaining a titration glucose level based on small glucose measurements and the state of the insulin state indicator by:
  (i) obtaining a primary time window within the time course defining the period of time comprising the glucose measurements in the first data set to be used for identifying the titration glucose level,
  (ii) identifying a titration subset of small glucose measurements, identified as a subset of small glucose measurements within the primary time window,
  (iii) obtaining the titration glucose level computed as a measure of central tendency of the titration subset of small glucose measurements, wherein the measure of central tendency represents a measure of small glucose measurements for the primary time window,
  (iv) associating the titration glucose level with the measure of central tendency;

(C) adjusting or maintaining the long acting insulin medicament dosage based upon the obtained titration glucose level, and wherein an insulin state indicator, wherein the insulin state indicator can indicate a short-acting-insulin-influence state, wherein the glucose measurements within the primary time window may be influenced by a short acting insulin medicament, and an only-long-acting-insulin-influence state, wherein the glucose measurements within the primary time window can be influenced by a long acting insulin medicament, but the measurements cannot be influenced by a short acting insulin medicament.

15. A computer program comprising instructions that, when executed by a computer having one or more processors and a memory, perform the method of claim 14.

* * * * *

UNITED STATES PATENT AND TRADEMARK OFFICE
CERTIFICATE OF CORRECTION

PATENT NO. : 11,298,461 B2
APPLICATION NO. : 16/622326
DATED : April 12, 2022
INVENTOR(S) : Tinna Bjoerk Aradottir et al.

Page 1 of 1

It is certified that error appears in the above-identified patent and that said Letters Patent is hereby corrected as shown below:

In the Claims

At Column 54, Claim number 6, Line number 28, please replace with the following:
"as a short-acting-insulin-influence state, and"

Signed and Sealed this
Eighteenth Day of October, 2022

Katherine Kelly Vidal
*Director of the United States Patent and Trademark Office*